United States Patent [19]
Croteau et al.

[11] Patent Number: 6,008,043
[45] Date of Patent: Dec. 28, 1999

[54] **ISOLATION AND BACTERIAL EXPRESSION OF A SESQUITERPENE SYNTHASE CDNA CLONE FROM PEPPERMINT(*MENTHA χ PIPERITA, L.*) THAT PRODUCES THE APHID ALARM PHEROMONE (E)-β-FARNESENE**

[75] Inventors: Rodney Bruce Croteau, Pullman; Mark Raymond Wildung, Colfax, both of Wash.; John E. Crock, Moscow, Id.

[73] Assignee: Washington State University Research Foundation, Pullman, Wash.

[21] Appl. No.: 09/166,460

[22] Filed: Oct. 5, 1998

Related U.S. Application Data

[60] Provisional application No. 60/061,144, Oct. 6, 1997.
[51] Int. Cl.$^6$ .............................. C12N 5/00; C12N 15/63; C12N 15/52
[52] U.S. Cl. .................... 435/325; 435/320.1; 435/69.1; 435/6; 435/183; 536/23.1; 536/23.2
[58] Field of Search ..................................... 435/325, 183, 435/320.1, 41, 69.1, 6; 530/350, 23.1, 23.2

[56] References Cited

PUBLICATIONS

Salin, F., Pauly, G., Charon, J. and Gleizes, M., *J. Plant Phys.*, 146, pp. 203–209 (1995).
Gershenzon, J., McCaskill, D., Rajaonarivony, J.I.M., Mihaliak, C., Karp, F. and Croteau, R. *Anal. Biochem,* 200, pp. 130–138 (1992).
Logemann, J., Schell, J. and Willmitzer, L., *Anal. Biochem,* 163 pp. 16–20, (1987).

*Primary Examiner*—Ponnathapura Achutamurthy
*Assistant Examiner*—Richard Hutson
*Attorney, Agent, or Firm*—Christensen, O'Connor, Johnson & Kindness PLLC

[57] ABSTRACT

A cDNA encoding (E)-β-farnesene synthase from peppermint (*Mentha piperita*) has been isolated and sequenced, and the corresponding amino acid sequence has been determined. Accordingly, an isolated DNA sequence (SEQ ID NO:1) is provided which codes for the expression of (E)-β-farnesene synthase (SEQ ID NO:2), from peppermint (*Mentha piperita*). In other aspects, replicable recombinant cloning vehicles are provided which code for (E)-β-farnesene synthase, or for a base sequence sufficiently complementary to at least a portion of (E)-β-farnesene synthase DNA or RNA to enable hybridization therewith. In yet other aspects, modified host cells are provided that have been transformed, transfected, infected and/or injected with a recombinant cloning vehicle and/or DNA sequence encoding (E)-β-farnesene synthase. Thus, systems and methods are provided for the recombinant expression of the aforementioned recombinant (E)-β-farnesene synthase that may be used to facilitate its production, isolation and purification in significant amounts. Recombinant (E)-β-farnesene synthase may be used to obtain expression or enhanced expression of (E)-β-farnesene synthase in plants in order to enhance the production of (E)-β-farnesene, or may be otherwise employed for the regulation or expression of (E)-β-farnesene synthase, or the production of its product.

5 Claims, 9 Drawing Sheets

γ-TERPINENE

TERPINOLENE

LIMONENE

GENERAL DISPHOSPHATE

E-OCIMENE

Z-OCIMENE

MYRCENE

SABINENE

ISOLATION AND BACTERIAL EXPRESSION OF A SESQUITERPENE SYNTHASE CDNA CLONE FROM PEPPERMINT(*MENTHA* χ *PIPERITA, L.*) THAT PRODUCES THE APHID ALARM PHEROMONE (E)-β-FARNESENE

This application claims benefit of U.S. provisional application Ser. No. 60/061,144 filed Oct. 6, 1997.

This invention was supported in part by NIH grant number GM-31354 DOE grant number DE-FG03-96E20212 and by Hatch Project grant number 0268 from the Agricultural Research Center, Washington State University. The government has certain rights in the invention. This application claims benefit of priority from U.S. Provisional Patent Application Ser. No. 60/061,144, filed Oct. 6th, 1997.

FIELD OF THE INVENTION

The present invention relates to nucleic acid sequences which code for (E)-β-farnesene synthases, such as the (E)-β-farnesene synthase from *Mentha piperita*, and to vectors containing the sequences, host cells containing the sequences and methods of producing recombinant (E)-β-farnesene synthases and their mutants.

BACKGROUND OF THE INVENTION (E)-β-farnesene (FIG. 1) is an acyclic sesquiterpene olefin that occurs in a wide range of both plant and animal taxa. Over 600 papers have been published on the occurrence of this natural product and its deployment as an important courier in chemical communication. The olefin is found in the essential oil of hundreds of species of both gymnosperms, such as *Torreya taxifolia* (Florida torreya) (Shu, C. K., Lawrence, B. M. and Croom, E. M., Jr. (1995) *J. Essent. Oil Res.* 7, 71–72) and *Larix leptolepis* (larch) (Nabeta, K., Ara, Y., Aoki, Y. and Miyake, M. (1990) *J. Nat. Prod.* 53, 1241–1248), and angiosperms, such as *Robinia pseudoacacia* (black locust) (Kamden, D. P., Gruber, K., Barkman, L. and Gage, D. A. (1994) *J. Essent. Oil Res.* 6, 199–200), *Medicago sativa* (alfalfa) (Kamm, J. A. and Buttery, R. G. (1983) *Entomol. Exp. Appl.* 33, 129–134), *Chamomilla recutita* (chamomile) (Matos, P. J. A., Machiado, M. I. L., Alencar, J. W. and Craveiro, A. A. (1993) *J. Essent. Oil Res.* 5, 337–339), *Vitis vinifera* (grapes) (Buchbauer, G., Jirovetz, L., Wasicky, M. and Nikiforov, A. (1994) *J. Essent. Oil Res.* 6, 311–314), *Cannabis sativa* (hemp) (Lemberkovics, E., Veszki, P., Verzar-Petri, G. and Trka, A. (1981) *Sci. Pharm.* 49, 401–408), *Zea mays* (corn) (Turlings, T. C. J., Tumlinson, J. H., Heath, R. R., Proveaux, A. T. and Doolittle, R. E. (1991) *J. Chem. Ecol.* 17, 2235–2251), *Piper nigrum* (black pepper), *Daucus carota* (carrot), and *Mentha x piperita* (peppermint) (Lawrence, B. M. (1972) *Ann. Acad. Bras. Cienc.* 44, (suppl.), 191–197).

While socially dominant male mice produce both α-farnesene and (E)-β-farnesene in their urine as pheromones (Novotny, M., Harvey, S. and Jemiolo, B. (1990) *Experientia* 46, 109–113), it is in the insects and plants that the use of (E)-β-farnesene as a semiochemical is most extensive. (E)-β-Farnesene is emitted by the Dufour's gland of andrenid bees (Fernandes, A., Duffield, R. M., Wheeler, J. W. and LaBerge, W. E. (1981) *J. Chem. Ecol.* 7, 453–460) and by several genera of ants (Ali, M. F., Morgan, E. D., Attygalle, A. B. and Billen, J. P. J. (1987) *Z. Naturforsch.* 42, 955–960; Jackson, B. D., Morgan, E. D. and Billen, J. P. J. (1990) *Naturwiss.* 77, 187–188; Ollet, D. G., Morgan, E. D., Attygalle, A. B. and Billen, J. P. J. (1987) *Z. Naturforsch.* 42, 141–146), where it serves both as a defensive allomone and as a trail pheromone. This sesquiterpene is synthesized de novo in the osmetrial glands of larval Papilio (Lepidoptera:Papilionidae) as an allomone (Honda, K. (1990) *Insect Biochem.* 20, 245–250), and it functions as a feeding stimulant to the sand fly *Lutzomyia longipalpis* (Diptera:Psychodidae), an important vector of the blood disease leishmaniasis (Tesh, R. B., Guzman, H. and Wilson, M. (1992) *J. Med. Entomol.* 29, 226–231). Several species of predatory carabid beetles use E-β-farnesene as a prey-finding kairomone (Kielty, J. P., Allen-Williams, L. J., Underwood, N. and Eastwood, E. A. (1996) *J. Insect Behav.* 9, 237–250). When released by corn, this olefin is also a kairomonal oviposition stimulant to the European corn borer (Ostrinia) (Binder, B. F., Robbins, J. C. and Wilson, R. L. (1995) *J. Chem. Ecol.* 21, 1315–1327). (E)-β-farnesene is the major component of pollen odor in Lupinus and stimulates pollination behavior in bumblebees (Dobson, H. E. M., Groth, I. and Bergstroem, G. (1996) *Am. J. Bot.* 83, 877–885). Feeding by larval lepidopterans, such as Heliothis or Spodoptera (Noctuidae), increases the amount of (E)-β-farnesene released by corn; the volatile olefin is then detected as a synomone by the parasitic wasp *Cotesia marginiventris* (Hymenoptera:Braconidae) for locating the lepidopteran hosts (Turlings, T. C. J., Tumlinson, J. H., Heath, R. R., Proveaux, A. T. and Doolittle, R. E. (1991) *J. Chem. Ecol.* 17, 2235–2251). Circumstantial evidence also suggests the lepidopteran induced production and emission of (E)-β-farnesene from corn serves as a synomone for *Cotesia kariyai* (Takabayashi, J., Takahashi, S., Dicke, M. and Posthumus, M. A. (1995) *J. Chem. Ecol.* 21, 273–287) and from cotton leaves as a synomone for *C. marginiventris* (Pare, P. W. and Tumlinson, J. H. (1997) *Nature* 385, 30–31; Loughrin, J. H., Manukian, A., Heath, R. R., Turlings, T. C. J. and Turnlinson, J. H. (1994) *Proc. Natl. Acad. Sci. USA* 91, 11836–11840).

Perhaps of greatest significance in plant-insect interactions is the use of E-β-farnesene by most aphid species as an alarm pheromone (Bowers, W. S., Nault, L. R., Webb, R. E. and Dutky, S. R. (1972) *Science* 177, 1121–1122; Edwards, L. J., Siddall, J. B., Dunham, L. L., Uden, P. and Kislow, C. J. (1973) *Nature* 241, 126–127). Aphids exposed to (E)-β-farnesene become agitated and disperse from their host plant (Wohlers, P. (1981) *Z Angew. Entomol.* 92, 329–336). Alate aphids are usually more sensitive than are apterae species and will often not colonize a host displaying (E)-β-farnesene. Ants that defend aphids are sensitive to host-emitted (E)-β-farnesene and, when exposed, will display aggressive behavior (Nault, L. R. and Montgomery, M. E. (1976) *Science* 192, 1349–1351). (E)-β-farnesene also mimics the action of juvenile hormone III in some insects (Mauchamp, B. and Pickett, J. J. (1987) *Agronomie* 7, 523–529), may play a role in control of aphid morphological types, and is acutely toxic to aphids at a dose of 100 ng/aphid (van Oosten, A. M., Gut, J., Harrewijn, P. and Piron, P. G. M. (1990) *Acta Phytopathol Entomol. Hung.* 25, 331–342). (E)-β-farnesene vapor is also toxic to whiteflies (Klijnstra, K. W., Corts, K. A. and van Oosten, A. M. (1992) *Meded. Fac. Landbouwwet* 57, 485–491).

Efforts to control aphid behavior by topical application of (E)-β-farnesene to crops have met with little success, due to volatility and rapid oxidative inactivation in air (Dawson, G. W., Griffiths, D. C., Pickett, J. A., Plumb, R. T., Woodcock, C. M. and Zhang, Z. N. (1988) *Pest. Sci.* 22, 17–30). Derivatives of (E)-β-farnesene with reduced volatility, or increased stability, have shown promise in reducing aphid-transmitted viruses, such as barley mosaic virus (Dawson, G. W., Griffiths, D. C., Pickett, J. A., Plumb, R. T., Woodcock, C. M. and Zhang, Z. N. (1988) *Pest. Sci.* 22, 17–30), potato virus Y (Gibson, R. W., Pickett, J. A., Dawson, G. W., Rice, A. D. and Stribley, M. F. (1984) *Ann. Appl. Entomol.* 104, 203–209), and beet mosaic virus (Gibson, R. W., Pickett, J. A., Dawson, G. W., Rice, A. D. and Stribley, M. F. (1984) *Ann. Appl. Entomol.* 104, 203–209). The wild potato *Solanum berthaultii*, which produces (E)-β-farnesene in type A trichomes, is more repellent to the green peach aphid than are commercial varieties of *S. tuberosum* that produce lower levels of the olefin (Gibson, R. W. and Pickett, J. A. (1983) *Nature* 302, 608–609; Ave, D. A., Gregory, P. and Tingey, W. M. (1987) *Entomol. Exp. App.* 44, 131–138). In alfalfa, repellency to the blue alfalfa aphid and the pea aphid is correlated with the leaf content of (E)-β-farnesene, but not with the amount of the co-occurring sesquiterpene caryophyllene (Mostafavi, R., Henning, J. A., Gardea-Torresday, J. and Ray, I. M. (1996) *J. Chem. Ecol.* 22, 1629–1638).

For plants that produce (E)-β-farnesene, breeding for increased production has met with some success (Mostafavi, R., Henning, J. A., Gardea-Torresday, J. and Ray, I. M. (1996) *J. Chem. Ecol.* 22, 1629–1638), but has been limited by genetic variation in these species. (E)-β-farnesene synthase has been purified from maritime pine (*Pinus pinaster*) and characterized (Salin, F., Pauly, G., Charon, J. and Gleizes, M. (1995) *J. Plant Phys.* 146, 203–209), but the gene has not yet been isolated from any source. A cDNA clone for (E)-β-farnesene synthase would, by transgenic manipulation, provide a valuable addition to the arsenal of natural compounds active in host plant resistance. The substrate for (E)-β-farnesene synthase is farnesyl diphosphate, a ubiquitous isoprenoid intermediate involved in cytoplasmic phytosterol biosynthesis. Sesquiterpene synthases lack plastidial targeting sequences and are localized to the cytoplasm (Chappell, J. (1995) *Annu. Rev. Plant Physiol. Plant Mol. Biol.* 46, 521–547). Therefore, even in plants that do not normally produce sesquiterpenes, a recombinant (E)-β-farnesene synthase would be directed to the cytoplasm where substrate is supplied by the mevalonate pathway and where production of (E)-β-farnesene should result.

SUMMARY OF THE INVENTION

In accordance with the foregoing, a cDNA encoding (E)-β-farnesene synthase from peppermint (*Mentha piperita*) has been isolated and sequenced, and the corresponding amino acid sequence has been deduced. Accordingly, the present invention relates to isolated DNA sequences which code for the expression of (E)-β-farnesene synthase, such as the sequence designated SEQ ID NO:1 which encodes an (E)-β-farnesene synthase protein (SEQ ID NO:2) from peppermint (*Mentha piperita*). Additionally, the present invention relates to isolated, recombinant (E)-β-farnesene synthase proteins from peppermint (*Mentha piperita*). In other aspects, the present invention is directed to replicable recombinant cloning vehicles comprising a nucleic acid sequence, e.g., a DNA sequence which codes for an (E)-β-farnesene synthase, or for a base sequence sufficiently complementary to at least a portion of DNA or RNA encoding (E)-β-farnesene synthase to enable hybridization therewith (e.g., antisense RNA or fragments of DNA complementary to a portion of DNA or RNA molecules encoding (E)-β-farnesene synthase which are useful as polymerase chain reaction primers or as probes for (E)-β-farnesene synthase or related genes). In yet other aspects of the invention, modified host cells are provided that have been transformed, transfected, infected and/or injected with a recombinant cloning vehicle and/or DNA sequence of the invention. Thus, the present invention provides for the recombinant expression of (E)-β-farnesene synthase, and the inventive concepts may be used to facilitate the production, isolation and purification of significant quantities of recombinant (E)-β-farnesene synthase (or of its primary enzyme products) for subsequent use, to obtain expression or enhanced expression of (E)-β-farnesene synthase in plants, microorganisms or animals, or may be otherwise employed in an environment where the regulation or expression of (E)-β-farnesene synthase is desired for the production of this synthase, or its enzyme product, or derivatives thereof

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENT

Figure 1:
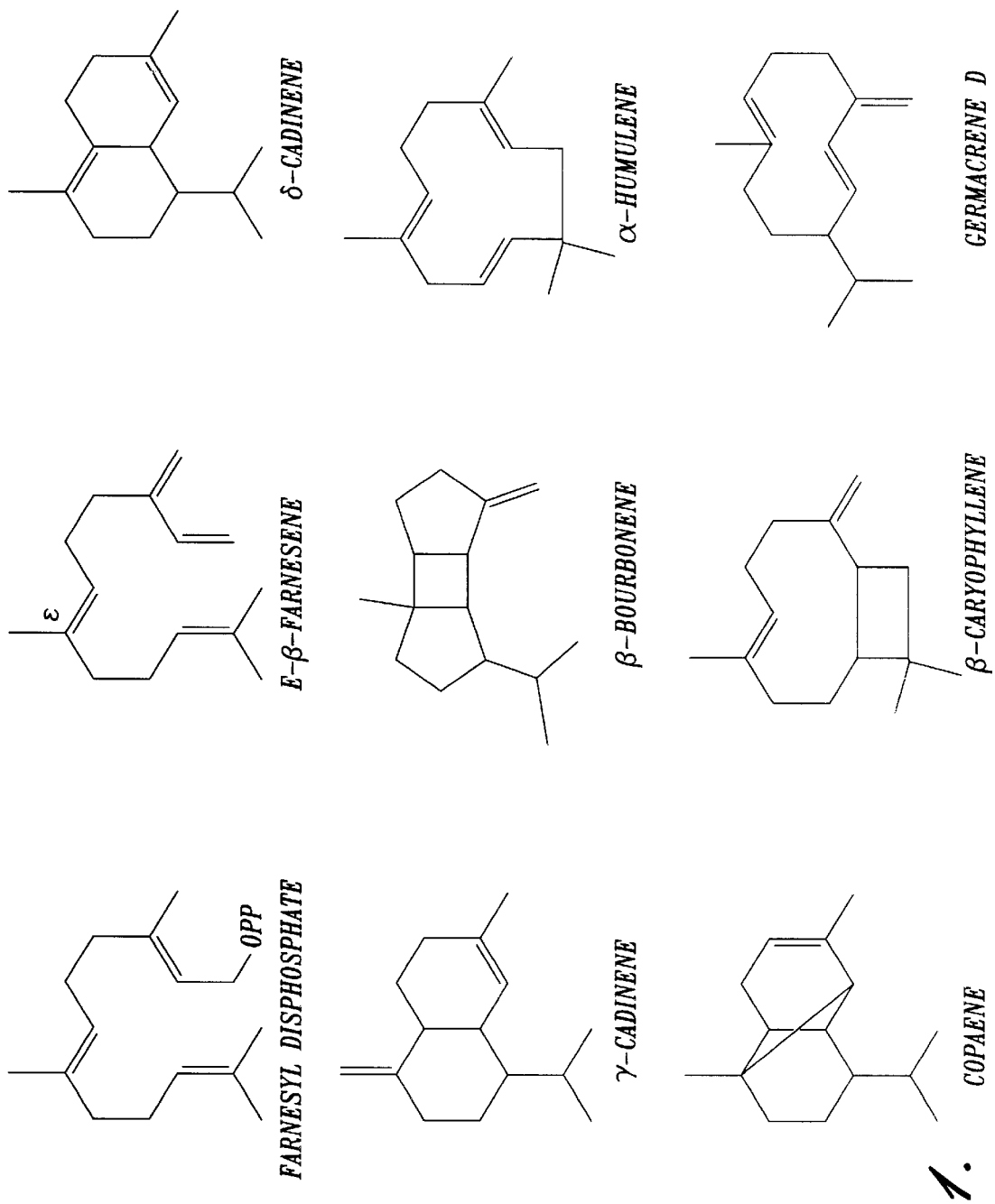
FIG. 1. The sesquiterpene synthase substrate, farnesyl diphosphate, and sesquiterpene olefins found in peppermint essential oil.

As used herein, the terms "amino acid" and "amino acids" refer to all naturally occurring L-α-amino acids or their residues. The amino acids are identified by either the single-letter or three-letter designations:

| Asp | D | aspartic acid | Ile | I | isoleucine |
|-----|---|---------------|-----|---|------------|
| Thr | T | threonine     | Leu | L | leucine    |
| Ser | S | serine        | Tyr | Y | tyrosine   |
| Glu | E | glutamic acid | Phe | F | phenylalanine |
| Pro | P | proline       | His | H | histidine  |

| Gly | G | glycine | Lys | K | lysine |
| Ala | A | alanine | Arg | R | arginine |
| Cys | C | cysteine | Trp | W | tryptophan |
| Val | V | valine | Gln | Q | glutamine |
| Met | M | methionine | Asn | N | asparagine |

As used herein, the term "nucleotide" means a monomeric unit of DNA or RNA containing a sugar moiety (pentose), a phosphate and a nitrogenous heterocyclic base. The base is linked to the sugar moiety via the glycosidic carbon (1' carbon of pentose) and that combination of base and sugar is called a nucleoside. The base characterizes the nucleotide with the four bases of DNA being adenine ("A"), guanine ("G"), cytosine ("C") and thymine ("T"). Inosine ("I") is a synthetic base that can be used to substitute for any of the four, naturally-occurring bases (A, C, G or T). The four RNA bases are A,G,C and uracil ("U"). The nucleotide sequences described herein comprise a linear array of nucleotides connected by phosphodiester bonds between the 3' and 5' carbons of adjacent pentoses.

"Oligonucleotide" refers to short length single or double stranded sequences of deoxyribonucleotides linked via phosphodiester bonds. The oligonucleotides are chemically synthesized by known methods and purified, for example, on polyacrylamide gels.

The term "(E)-β-farnesene synthase" refers to an enzyme that is capable of converting farnesyl diphosphate to (E)-β-farnesene.

The term "essential oil plant," or "essential oil plants," refers to a group of plant species that produce high levels of monoterpenoid and/or sesquiterpenoid and/or diterpenoid oils, and/or high levels of monoterpenoid and/or sesquiterpenoid and/or diterpenoid resins. The foregoing oils and/or resins account for greater than about 0.005% of the fresh weight of an essential oil plant that produces them. The essential oils and/or resins are more fully described, for example, in E. Guenther, The Essential Oils, Vols. I–VI, R. E. Krieger Publishing Co., Huntington N.Y., 1975, incorporated herein by reference. The essential oil plants include, but are not limited to:

Lamiaceae, including, but not limited to, the following species: Ocimum (basil), Lavandula (Lavender), Origanum (oregano), Mentha (mint), Salvia (sage), Rosmecinus (rosemary), Thymus (thyme), Satureja and Monarda.

Umbelliferae, including, but not limited to, the following species: Carum (caraway), Anethum (dill), feniculum (fennel) and Daucus (carrot).

Asteraceae (Compositae), including, but not limited to, the following species: Artemisia (tarragon, sage brush), Tanacetum (tansy).

Rutaceae (e.g., citrus plants); Rosaceae (e.g., roses); Myrtaceae (e.g., eucalyptus, Melaleuca); the Gramineae (e.g., Cymbopogon (citronella)); Geranaceae (Geranium) and certain conifers including Abies (e.g., Canadian balsam), Cedrus (cedar) and Thuja and Juniperus.

The range of essential oil plants is more fully set forth in E. Guenther, *The Essential Oils*, Vols. I–VI, R.E. Krieger Publishing Co., Huntington N.Y., 1975, which is incorporated herein by reference.

The term "angiosperm" refers to a class of plants that produce seeds that are enclosed in an ovary.

The term "gymnosperm" refers to a class of plants that produce seeds that are not enclosed in an ovary.

Abbreviations used are: bp, base pairs; dpm, disintegrations per minute; DTT, dithiothreitol; EDTA, ethylenediaminetetraacetic acid; FDP, farnesyl diphosphate; GC, gas chromatography; GDP, geranyl diphosphate; GGDP, geranylgeranyl diphosphate; I, identity; IPTG, isopropyl-β-D-thiogalactopyranoside; LB, Luria-Bertani; Mopso, 3-(N-morpholino)-2-hydroxypropane-sulfonic acid; MS, mass spectrometry; PVPP, polyvinylpolypyrrolidone; S, similarity.

The term "percent identity" (%I) means the percentage of amino acids or nucleotides that occupy the same relative position when two amino acid sequences, or two nucleic acid sequences, are aligned side by side.

The term "percent similarity" (%S) is a statistical measure of the degree of relatedness of two compared protein sequences. The percent similarity is calculated by a computer program that assigns a numerical value to each compared pair of amino acids based on chemical similarity (e.g., whether the compared amino acids are acidic, basic, hydrophobic, aromatic, etc.) and/or evolutionary distance as measured by the minimum number of base pair changes that would be required to convert a codon encoding one member of a pair of compared amino acids to a codon encoding the other member of the pair. Calculations are made after a best fit alignment of the two sequences has been made empirically by iterative comparison of all possible alignments. (Henikoff, S. and Henikoff, J. G., *Proc. Nat'l Acad Sci USA* 89: 10915–10919, 1992).

The abbreviation "SSC" refers to a buffer used in nucleic acid hybridization solutions. One liter of the 20× (twenty times concentrate) stock SSC buffer solution (pH 7.0) contains 175.3 g sodium chloride and 88.2 g sodium citrate.

The terms "alteration", "amino acid sequence alteration", "variant" and "amino acid sequence variant" refer to (E)-β-farnesene synthase molecules with some differences in their amino acid sequences as compared to the corresponding, native, i.e., naturally-occurring, (E)-β-farnesene synthases. Ordinarily, the variants will possess at least about 70% homology with the corresponding native (E)-β-farnesene synthases, and preferably, they will be at least about 80% homologous with the corresponding, native (E)-β-farnesene synthases. The amino acid sequence variants of the (E)-β-farnesene synthases falling within this invention possess substitutions, deletions, and/or insertions at certain positions. Sequence variants of (E)-β-farnesene synthases may be used to attain desired enhanced or reduced enzymatic activity, modified regiochemistry or stereochemistry, or altered substrate utilization or product distribution.

Substitutional (E)-β-farnesene synthase variants are those that have at least one amino acid residue in the native (E)-β-farnesene synthase sequence removed and a different amino acid inserted in its place at the same position. The substitutions may be single, where only one amino acid in the molecule has been substituted, or they may be multiple, where two or more amino acids have been substituted in the same molecule. Substantial changes in the activity of the (E)-β-farnesene synthase molecules of the present invention may be obtained by substituting an amino acid with a side chain that is significantly different in charge and/or structure from that of the native amino acid. This type of substitution would be expected to affect the structure of the polypeptide backbone and/or the charge or hydrophobicity of the molecule in the area of the substitution.

Moderate changes in the activity of the (E)-β-farnesene synthase molecules of the present invention would be expected by substituting an amino acid with a side chain that is similar in charge and/or structure to that of the native molecule. This type of substitution, referred to as a conservative substitution, would not be expected to substantially alter either the structure of the polypeptide backbone or the charge or hydrophobicity of the molecule in the area of the substitution.

Insertional (E)-β-farnesene synthase variants are those with one or more amino acids inserted immediately adjacent to an amino acid at a particular position in the native (E)-β-farnesene synthase molecule. Immediately adjacent to an amino acid means connected to either the α-carboxy or α-amino functional group of the amino acid. The insertion may be one or more amino acids. Ordinarily, the insertion will consist of one or two conservative amino acids. Amino acids similar in charge and/or structure to the amino acids adjacent to the site of insertion are defined as conservative. Alternatively, this invention includes insertion of an amino acid with a charge and/or structure that is substantially different from the amino acids adjacent to the site of insertion.

Deletional variants are those where one or more amino acids in the native (E)-β-farnesene synthase molecules have been removed. Ordinarily, deletional variants will have one or two amino acids deleted in a particular region of the (E)-β-farnesene synthase molecule.

The terms "biological activity", "biologically active", "activity" and "active" refer to the ability of the (E)-β-farnesene synthases of the present invention to catalyze the formation of (E)-β-farnesene from farnesyl diphosphate. (E)-β-farnesene synthase activity is measured in an enzyme activity assay, such as the assay described in Example 1 herein. Amino acid sequence variants of the (E)-β-farnesene synthases of the present invention may have desirable altered biological activity including, for example, altered reaction kinetics, substrate utilization, product distribution or other characteristics such as regiochemistry and stereochemistry.

The terms "DNA sequence encoding", "DNA encoding" and "nucleic acid encoding" refer to the order or sequence of deoxyribonucleotides along a strand of deoxyribonucleic acid. The order of these deoxyribonucleotides determines the order of amino acids along the translated polypeptide chain. The DNA sequence thus codes for the amino acid sequence.

The terms "replicable expression vector" and "expression vector" refer to a piece of DNA, usually double-stranded, which may have inserted into it another piece of DNA (the insert DNA) such as, but not limited to, a cDNA molecule. The vector is used to transport the insert DNA into a suitable host cell. The insert DNA may be derived from the host cell, or may be derived from a different cell or organism. Once in the host cell, the vector can replicate independently of or coincidental with the host chromosomal DNA, and several copies of the vector and its inserted DNA may be generated. In addition, the vector contains the necessary elements that permit translating the insert DNA into a polypeptide. Many molecules of the polypeptide encoded by the insert DNA can thus be rapidly synthesized.

The terms "transformed host cell," "transformed" and "transformation" refer to the introduction of DNA into a cell. The cell is termed a "host cell", and it may be a prokaryotic or a eukaryotic cell. Typical prokaryotic host cells include various strains of E. coli. Typical eukaryotic host cells are plant cells, such as maize cells, yeast cells, insect cells or animal cells. The introduced DNA is usually in the form of a vector containing an inserted piece of DNA. The introduced DNA sequence may be from the same species as the host cell or from a different species from the host cell, or it may be a hybrid DNA sequence, containing some foreign DNA and some DNA derived from the host species.

In accordance with the present invention, a cDNA (SEQ ID NO:1) encoding (E)-β-farnesene synthase (SEQ ID NO:2) from peppermint (Mentha piperita) was isolated and sequenced in the following manner. An enriched cDNA library was constructed from peppermint secretory cell clusters consisting of the eight glandular cells subtending the oil droplet. These cell clusters were harvested by leaf surface abrasion and the RNA contained therein was isolated. mRNA was purified by oligo-dT cellulose chromatography, and 5 μg of mRNA was used to construct a XZAPII cDNA library.

Plasmids were excised from the library en mass and used to transform E. coli strain XLOLR. Approximately 150 individual plasmid-bearing strains were grown in 5 ml LB media overnight, and the corresponding plasmids were purified before partial 5'-sequencing. Putative terpenoid synthase genes were identified by sequence comparison using the BLAST program of the GCG Wisconsin Package ver. 8. Bluescript plasmids harboring unique full-length cDNA inserts with high similarity to known plant terpenoid synthases were tested for functional expression following transformation into E. coli XL1-Blue cells. A single extract, from the bacteria containing clone p43, including the cDNA insert set forth in SEQ ID NO:1, produced a sesquiterpene olefin from [1-$^3$H]FDP, and this clone was selected for further study.

A cell-free extract of E. coli XL-1 Blue cells harboring the plasmid p43, including the cDNA insert set forth in SEQ ID NO:1, was prepared and shown to be capable of catalyzing the divalent metal ion-dependent conversion of [1-$^3$H]FDP to labeled sesquiterpene olefins. Control reactions, employing extracts of XL1-Blue cells transformed with pBluescript lacking the insert, evidenced no detectable production of sesquiterpene olefins from [1-$^3$H]FDP, thereby demonstrating that a cDNA clone (SEQ ID NO:1) encoding (E)-β-farnesene synthase (SEQ ID NO:2) had been acquired.

The recombinant (E)-β-farnesene synthase (SEQ ID NO:2) was inactive with the $C_{20}$ substrate analog [1-$^3$H] GGDP, but was able to catalyze the divalent cation-dependent conversion of the $C_{10}$ analog [1-$^3$H]GDP to monoterpene olefins. Control reactions, employing extracts of XL1-Blue cells transformed with pBluescript lacking the insert, evidenced no detectable production of monoterpene olefins from [1-$^3$H]GDP, thereby confirming that the monoterpene synthase activity expressed from the cDNA insert of p43 (SEQ ID NO:1) was a function of the (E)-β-farnesene synthase (SEQ ID NO:2). This is the first report describing the utilization of GDP by a sesquiterpene synthase.

Complete sequencing of the (E)-β-farnesene synthase cDNA (SEQ ID NO:1) contained in p43 revealed an insert size of 1959 bp encoding an open reading frame of 550 amino acids with a deduced molecular weight of 63,829. The deduced amino acid sequence of the (E)-β-farnesene synthase (SEQ ID NO:2) lacks a plastidial targeting peptide. Like all other known terpenoid synthases, (E)-β-farnesene synthase is rich in tryptophan (1.8%) and arginine (5.5%) residues, and bears a DDXXD motif (SEQ ID NO:3) (residues 301–305 of SEQ ID NO:2) which is believed to coordinate the divalent metal ion chelated to the substrate diphosphate group. The enzyme has a deduced isoelectric point at pH 5.16.

The isolation of a cDNA (SEQ ID NO:1) encoding (E)-β-farnesene synthase (SEQ ID NO:2) permits the development of efficient expression systems for this functional enzyme; provides useful tools for examining the developmental regulation of (E)-β-farnesene synthase; permits investigation of the reaction mechanism(s) of this enzyme, and permits the isolation of other (E)-β-farnesene synthases. The isolation of an (E)-β-farnesene synthase cDNA (SEQ ID NO:1) also permits the transformation of a wide range of organisms in order to enhance, enable or otherwise alter, the synthesis of (E)-β-farnesene.

Although the (E)-β-farnesene synthase protein set forth in SEQ ID NO:2 lacks a plastidial targeting sequence, a targeting sequence from another protein can be included in the (E)-β-farnesene synthase amino terminus. Transport sequences well known in the art (See, for example, the following publications, the cited portions of which are incorporated by reference herein: von Heijne et al., *Eur. J. Biochem.*, 180:535–545, 1989; Stryer, *Biochemistry*, W.H. Freeman and Company, New York, N.Y., p. 769 [1988]) may be employed to direct (E)-β-farnesene synthase to other cellular or extracellular locations.

In addition to the native (E)-β-farnesene synthase amino acid sequence of SEQ ID NO:2, sequence variants produced by deletions, substitutions, mutations and/or insertions are intended to be within the scope of the invention except insofar as limited by the prior art. The (E)-β-farnesene synthase amino acid sequence variants of this invention may be constructed by mutating the DNA sequences that encode the wild-type synthases, such as by using techniques commonly referred to as site-directed mutagenesis. Nucleic acid molecules encoding the (E)-β-farnesene synthases of the present invention can be mutated by a variety of PCR techniques well known to one of ordinary skill in the art. (See, for example, the following publications, the cited portions of which are incorporated by reference herein: "PCR Strategies", M. A. Innis, D. H. Gelfand and J. J. Sninsky, eds., 1995, Academic Press, San Diego, Calif. (Chapter 14); "PCR Protocols: A Guide to Methods and Applications", M. A. Innis, D. H. Gelfand, J. J. Sninsky and T. J. White, eds., Academic Press, NY (1990).

By way of non-limiting example, the two primer system utilized in the Transformer Site-Directed Mutagenesis kit from Clontech, may be employed for introducing site-directed mutants into the (E)-β-farnesene synthase genes of the present invention. Following denaturation of the target plasmid in this system, two primers are simultaneously annealed to the plasmid; one of these primers contains the desired site-directed mutation, the other contains a mutation at another point in the plasmid resulting in elimination of a unique restriction site. Second strand synthesis is then carried out, tightly linking these two mutations, and the resulting plasmids are transformed into a mutS strain of *E. coli*. Plasmid DNA is isolated from the transformed bacteria, restricted with the relevant restriction enzyme (thereby linearizing the unmutated plasmids), and then retransformed into *E. coli*. This system allows for generation of mutations directly in an expression plasmid, without the necessity of subcloning or generation of single-stranded phagemids. The tight linkage of the two mutations and the subsequent linearization of unmutated plasmids results in high mutation efficiency and allows minimal screening. Following synthesis of the initial restriction site primer, this method requires the use of only one new primer type per mutation site. Rather than prepare each positional mutant separately, a set of "designed degenerate" oligonucleotide primers can be synthesized in order to introduce all of the desired mutations at a given site simultaneously. Transformants can be screened by sequencing the plasmid DNA through the mutagenized region to identify and sort mutant clones. Each mutant DNA can then be fully sequenced or restricted and analyzed by electrophoresis on Mutation Detection Enhancement gel (J. T. Baker) to confirm that no other alterations in the sequence have occurred (by band shift comparison to the unmutagenized control).

Again, by way of non-limiting example, the two primer system utilized in the QuikChange™ Site-Directed Mutagenesis kit from Stratagene (LaJolla, Calif.), may be employed for introducing site-directed mutants into the (E)-β-farnesene synthase genes of the present invention. Double-stranded plasmid DNA, containing the insert bearing the target mutation site, is denatured and mixed with two oligonucleotides complementary to each of the strands of the plasmid DNA at the target mutation site. The annealed oligonucleotide primers are extended using Pfu DNA polymerase, thereby generating a mutated plasmid containing staggered nicks. After temperature cycling, the unmutated, parental DNA template is digested with restriction enzyme DpnI which cleaves methylated or hemimethylated DNA, but which does not cleave unmethylated DNA. The parental, template DNA is almost always methylated or hemimethylated since most strains of *E. coli*, from which the template DNA is obtained, contain the required methylase activity. The remaining, annealed vector DNA incorporating the desired mutation(s) is transformed into *E. coli*.

The mutated (E)-β-farnesene synthase gene can be cloned into a pET (or other) overexpression vector that can be employed to transform *E. coli* such as strain *E. coli* BL21 (DE3)pLysS, for high level production of the mutant protein, and purification by standard protocols. Examples of plasmid vectors and *E. coli* strains that can be used to express high levels of the (E)-β-farnesene synthase proteins of the present invention are set forth in Sambrook et al, *Molecular Cloning, A Laboratory Manual*, 2nd Edition (1989), Chapter 17. The method of FAB-MS mapping can be employed to rapidly check the fidelity of mutant expression. This technique provides for sequencing segments throughout the whole protein and provides the necessary confidence in the sequence assignment. In a mapping experiment of this type, protein is digested with a protease (the choice will depend on the specific region to be modified since this segment is of prime interest and the remaining map should be identical to the map of unmutagenized protein). The set of cleavage fragments is fractionated by microbore HPLC (reversed phase or ion exchange, again depending on the specific region to be modified) to provide several peptides in each fraction, and the molecular weights of the peptides are determined by FAB-MS. The masses are then compared to the molecular weights of peptides expected from the digestion of the predicted sequence, and the correctness of the sequence quickly ascertained. Since the exemplary mutagenesis techniques set forth herein produce site-directed mutations, sequencing of the altered peptide should not be necessary if the mass spectrograph agrees with prediction. If necessary to verify a changed residue, CAD-tandem MS/MS can be employed to sequence the peptides of the mixture in question, or the target peptide can be purified for subtractive Edman degradation or carboxypeptidase Y digestion depending on the location of the modification.

In the design of a particular site directed mutagenesis experiment, it is generally desirable to first make a non-conservative substitution (e.g., Ala for Cys, His or Glu) and determine if activity is greatly impaired as a consequence. The properties of the mutagenized protein are then examined with particular attention to the kinetic parameters of $K_m$ and $k_{cat}$ as sensitive indicators of altered function, from which changes in binding and/or catalysis per se may be deduced by comparison to the native enzyme. If the residue is by this means demonstrated to be important by activity impairment, or knockout, then conservative substitutions can be made, such as Asp for Glu to alter side chain length, Ser for Cys, or Arg for His. For hydrophobic segments, it is largely size that is usefully altered, although aromatics can also be substituted for alkyl side chains. Changes in the normal product distribution can indicate which step(s) of the reaction sequence have been altered by the mutation. Modification of the hydrophobic pocket can be employed to change binding conformations for substrates and result in altered regiochemistry and/or stereochemistry.

Other site directed mutagenesis techniques may also be employed with the nucleotide sequences of the invention. For example, restriction endonuclease digestion of DNA followed by ligation may be used to generate deletion variants of (E)-β-farnesene synthase, as described in section 15.3 of Sambrook et al. *Molecular Cloning: A Laboratory Manual*, 2nd Ed., Cold Spring Harbor Laboratory Press, New York, N.Y. [1989], incorporated herein by reference. A similar strategy may be used to construct insertion variants, as described in section 15.3 of Sambrook et al., supra.

Oligonucleotide-directed mutagenesis may also be employed for preparing substitution variants of this invention. It may also be used to conveniently prepare the deletion and insertion variants of this invention. This technique is well known in the art as described by Adelman et al. (DNA 2:183 [1983]); Sambrook et al., supra; "Current Protocols in Molecular Biology", 1991, Wiley (N.Y.), F. T. Ausubel, R. Brent, R. E. Kingston, D. D. Moore, J. D. Seidman, J. A. Smith and K. Struhl, eds, incorporated herein by reference.

Generally, oligonucleotides of at least 25 nucleotides in length are used to insert, delete or substitute two or more nucleotides in the (E)-β-farnesene synthase molecule. An optimal oligonucleotide will have 12 to 15 perfectly matched nucleotides on either side of the nucleotides coding for the mutation. To mutagenize wild-type (E)-β-farnesene synthase, the oligonucleotide is annealed to the single-stranded DNA template molecule under suitable hybridization conditions. A DNA polymerizing enzyme, usually the Klenow fragment of *E. coli* DNA polymerase I, is then added. This enzyme uses the oligonucleotide as a primer to complete the synthesis of the mutation-bearing strand of DNA. Thus, a heteroduplex molecule is formed such that one strand of DNA encodes the wild-type synthase inserted in the vector, and the second strand of DNA encodes the mutated form of the synthase inserted into the same vector. This heteroduplex molecule is then transformed into a suitable host cell.

Mutants with more than one amino acid substituted may be generated in one of several ways. If the amino acids are located close together in the polypeptide chain, they may be mutated simultaneously using one oligonucleotide that codes for all of the desired amino acid substitutions. If, however, the amino acids are located some distance from each other (separated by more than ten amino acids, for example) it is more difficult to generate a single oligonucleotide that encodes all of the desired changes. Instead, one of two alternative methods may be employed. In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions. An alternative method involves two or more rounds of mutagenesis to produce the desired mutant. The first round is as described for the single mutants: wild-type (E)-β-farnesene synthase DNA is used for the template, an oligonucleotide encoding the first desired amino acid substitution(s) is annealed to this template, and the heteroduplex DNA molecule is then generated. The second round of mutagenesis utilizes the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and second rounds of mutagenesis. This resultant DNA can be used as a template in a third round of mutagenesis, and so on.

A gene encoding (E)-β-farnesene synthase may be incorporated into any organism (intact plant, animal, microbe, etc.), or cell culture derived therefrom, that produces substrates that can be converted to (E)-β-farnesene. An (E)-β-farnesene synthase gene may be introduced into any organism for a variety of purposes including, but not limited to: production of (E)-β-farnesene synthase, or its product (E)-β-farnesene; enhancement of the rate of production and/or the absolute amount of (E)-β-farnesene; enhancement of protection of plants against pests and pathogens, for example by producing (E)-β-farnesene to act as a pollinator attractant synomone for predators and parasites of plant pests, or as an aphid alarm pheromone. While the nucleic acid molecules of the present invention can be introduced into any organism, the nucleic acid molecules of the present invention will preferably be introduced into a plant species.

Eukaryotic expression systems may be utilized for the production of (E)-β-farnesene synthase since they are capable of carrying out any required posttranslational modifications and of directing the enzyme to the proper cellular compartment. A representative eukaryotic expression system for this purpose uses the recombinant baculovirus, *Autographa californica* nuclear polyhedrosis virus (AcNPV; M. D. Summers and G. E. Smith, *A Manual of Methods for Baculovirus Vectors and Insect Cell Culture Procedures* [1986]; Luckow et al., *Bio-technology*, 6:47–55 [1987]) for expression of the (E)-β-farnesene synthases of the invention. Infection of insect cells (such as cells of the species *Spodoptera frugiperda*) with the recombinant baculoviruses allows for the production of large amounts of the (E)-β-farnesene synthase proteins. In addition, the baculovirus system has other important advantages for the production of recombinant (E)-β-farnesene synthase. For example, baculoviruses do not infect humans and can therefore be safely handled in large quantities. In the baculovirus system, a DNA construct is prepared including a DNA segment encoding (E)-β-farnesene synthase and a vector. The vector may comprise the polyhedron gene promoter region of a baculovirus, the baculovirus flanking sequences necessary for proper cross-over during recombination (the flanking sequences comprise about 200–300 base pairs adjacent to the promoter sequence) and a bacterial origin of replication which permits the construct to replicate in bacteria. The vector is constructed so that (i) the DNA segment is placed adjacent (or operably linked or "downstream" or "under the control of") to the polyhedron gene promoter and (ii) the promoter/(E)-β-farnesene synthase combination is flanked on both sides by 200–300 base pairs of baculovirus DNA (the flanking sequences).

To produce the (E)-β-farnesene synthase DNA construct, a cDNA clone encoding the full length (E)-β-farnesene synthase is obtained using methods such as those described herein. The DNA construct is contacted in a host cell with baculovirus DNA of an appropriate baculovirus (that is, of the same species of baculovirus as the promoter encoded in the construct) under conditions such that recombination is effected. The resulting recombinant baculoviruses encode the full (E)-β-farnesene synthase. For example, an insect host cell can be cotransfected or transfected separately with the DNA construct and a functional baculovirus. Resulting recombinant baculoviruses can then be isolated and used to infect cells to effect production of the (E)-β-farnesene synthase. Host insect cells include, for example, *Spodoptera frugiperda* cells, that are capable of producing a baculovirus-expressed (E)-β-farnesene synthase. Insect host cells infected with a recombinant baculovirus of the present invention are then cultured under conditions allowing expression of the baculovirus-encoded (E)-β-farnesene synthase. (E)-β-farnesene synthase thus produced is then extracted from the cells using methods known in the art.

Other eukaryotic microbes such as yeasts may also be used to practice this invention. The baker's yeast *Saccharomyces cerevisiae*, is a commonly used yeast, although several other strains are available. The plasmid YRp7 (Stinchcomb et al., *Nature*, 282:39 [1979]; Kingsman et al., Gene 7:141 [1979]; Tschemper et al., *Gene*, 10:157 [1980]) is commonly used as an expression vector in Saccharomyces. This plasmid contains the trp1 gene that provides a selection marker for a mutant strain of yeast lacking the ability to grow in the absence of tryptophan, such as strains ATCC No. 44,076 and PEP4-1 (Jones, *Genetics*, 85:12 [1977]). The presence of the trp1 lesion as a characteristic of the yeast host cell genome then provides an effective environment for detecting transformation by growth in the absence of tryptophan. Yeast host cells are generally transformed using the polyethylene glycol method, as described by Hinnen (*Proc. Natl. Acad. Sci. USA*, 75:1929 [1978]). Additional yeast transformation protocols are set forth in Gietz et al., *N.A.R.*, 20(17):1425(1992); Reeves et al., *FEMS*, 99(2–3):193–197, (1992), both of which publications are incorporated herein by reference.

Suitable promoting sequences in yeast vectors include the promoters for 3-phosphoglycerate kinase (Hitzeman et al.,*J. Biol. Chem.*, 255:2073 [1980]) or other glycolytic enzymes (Hess et al., *J. Adv. Enzyme Reg.* 7:149 [1968]; Holland et al., *Biochemistry*, 17:4900 [1978]), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In the construction of suitable expression plasmids, the termination sequences associated with these genes are also ligated into the expression vector 3' of the sequence desired to be expressed to provide polyadenylation of the mRNA and termination. Other promoters that have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing yeast-compatible promoter, origin of replication and termination sequences is suitable.

Cell cultures derived from multicellular organisms, such as plants, may be used as hosts to practice this invention. Transgenic plants can be obtained, for example, by transferring plasmids that encode (E)-β-farnesene synthase and a selectable marker gene, e.g., the kan gene encoding resistance to kanamycin, into *Agrobacterium tumifaciens* containing a helper Ti plasmid as described in Hoeckema et al., *Nature*, 303:179–181 [1983] and culturing the Agrobacterium cells with leaf slices, or other tissues or cells, of the plant to be transformed as described by An et al., *Plant Physiology*, 81:301–305 [1986]. Transformation of cultured plant host cells is normally accomplished through *Agrobacterium tumifaciens*. Cultures of mammalian host cells and other host cells that do not have rigid cell membrane barriers are usually transformed using the calcium phosphate method as originally described by Graham and Van der Eb (*Virology*, 52:546 [1978]) and modified as described in sections 16.32–16.37 of Sambrook et al., supra. However, other methods for introducing DNA into cells such as Polybrene (Kawai and Nishizawa, *Mol. Cell. Biol.*, 4:1172 [1984]), protoplast fusion (Schaffner, *Proc. Natl. Acad Sci. USA*, 77:2163 [1980]), electroporation (Neumann et al., *EMBO J.*, 1:841 [1982]), and direct microinjection into nuclei (Capecchi, *Cell*, 22:479 [1980]) may also be used. Additionally, animal transformation strategies are reviewed in Monastersky G. M. and Robl, J. M., *Strategies in Transgenic Animal Science*, ASM Press, Washington, D.C., 1995, incorporated herein by reference. Transformed plant calli may be selected through the selectable marker by growing the cells on a medium containing, e.g., kanamycin, and appropriate amounts of phytohormone such as naphthalene acetic acid and benzyladenine for callus and shoot induction. The plant cells may then be regenerated and the resulting plants transferred to soil using techniques well known to those skilled in the art.

In addition, a gene regulating (E)-β-farnesene synthase production can be incorporated into the plant along with a necessary promoter which is inducible. In the practice of this embodiment of the invention, a promoter that only responds to a specific external or internal stimulus is fused to the target cDNA. Thus, the gene will not be transcribed except in response to the specific stimulus. As long as the gene is not being transcribed, its gene product and enzyme product are not produced.

An illustrative example of a responsive promoter system that can be used in the practice of this invention is the glutathione-S-transferase (GST) system in maize. GSTs are a family of enzymes that can detoxify a number of hydrophobic electrophilic compounds that often are used as pre-emergent herbicides (Weigand et al., *Plant Molecular Biology*, 7:235–243 [1986]). Studies have shown that the GSTs are directly involved in causing this enhanced herbicide tolerance. This action is primarily mediated through a specific 1.1 kb mRNA transcription product. In short, maize has a naturally occurring quiescent gene already present that can respond to external stimuli and that can be induced to produce a gene product. This gene has previously been identified and cloned. Thus, in one embodiment of this invention, the promoter is removed from the GST responsive gene and attached to an (E)-β-farnesene synthase gene that previously has had its native promoter removed. This engineered gene is the combination of a promoter that responds to an external chemical stimulus and a gene responsible for successful production of (E)-β-farnesene synthase.

In addition to the methods described above, several methods are known in the art for transferring cloned DNA into a wide variety of plant species, including gymnosperms, angiosperms, monocots and dicots (see, e.g., Glick and Thompson, eds., *Methods in Plant Molecular Biology*, CRC Press, Boca Raton, Fla. [1993], incorporated by reference herein). Representative examples include electroporation-facilitated DNA uptake by protoplasts in which an electrical pulse transiently permeabilizes cell membranes, permitting the uptake of a variety of biological molecules, including recombinant DNA (Rhodes et al., *Science*, 240:204–207 [1988]); treatment of protoplasts with polyethylene glycol (Lyznik et al., *Plant Molecular Biology*, 13:151–161 [1989]); and bombardment of cells with DNA-laden microprojectiles which are propelled by explosive force or compressed gas to penetrate the cell wall (Klein et al., *Plant Physiol.* 91:440–444 [1989] and Boynton et al., *Science*, 240:1534–1538 [1988]). Transformation of Taxus species can be achieved, for example, by employing the methods set forth in Han et al, *Plant Science*, 95:187–196 (1994), incorporated by reference herein. A method that has been applied to Rye plants (*Secale cereale*) is to directly inject plasmid DNA, including a selectable marker gene, into developing floral tillers (de la Pena et al., *Nature* 325:274–276 (1987)). Further, plant viruses can be used as vectors to transfer genes to plant cells. Examples of plant viruses that can be used as vectors to transform plants include the Cauliflower Mosaic Virus (Brisson et al., *Nature* 310: 511–514 (1984); Additionally, plant transformation strategies and techniques are reviewed in Birch, R. G., *Ann Rev Plant Phys Plant Mol Biol*, 48:297 (1997); Forester etal., *Exp. Agric.*, 33:15–33 (1997). The aforementioned publications disclosing plant transformation techniques are incorporated herein by reference, and minor variations make these technologies applicable to a broad range of plant species.

Each of these techniques has advantages and disadvantages. In each of the techniques, DNA from a plasmid is genetically engineered such that it contains not only the gene of interest, but also selectable and screenable marker genes. A selectable marker gene is used to select only those cells that have integrated copies of the plasmid (the construction is such that the gene of interest and the selectable and screenable genes are transferred as a unit). The screenable gene provides another check for the successful culturing of only those cells carrying the genes of interest. A commonly used selectable marker gene is neomycin phosphotransferase II (NPT II). This gene conveys resistance to kanamycin, a compound that can be added directly to the growth media on which the cells grow. Plant cells are normally susceptible to kanamycin and, as a result, die. The presence of the NPT II gene overcomes the effects of the kanamycin and each cell with this gene remains viable. Another selectable marker gene which can be employed in the practice of this invention is the gene which confers resistance to the herbicide glufosinate (Basta). A screenable gene commonly used is the β-glucuronidase gene (GUS). The presence of this gene is characterized using a histochemical reaction in which a sample of putatively transformed cells is treated with a GUS assay solution. After an appropriate incubation, the cells containing the GUS gene turn blue.

The plasmid containing one or more of these genes is introduced into either plant protoplasts or callus cells by any of the previously mentioned techniques. If the marker gene is a selectable gene, only those cells that have incorporated the DNA package survive under selection with the appropriate phytotoxic agent. Once the appropriate cells are identified and propagated, plants are regenerated. Progeny from the transformed plants must be tested to insure that the DNA package has been successfully integrated into the plant genome.

Mammalian host cells may also be used in the practice of the invention. Examples of suitable mammalian cell lines include monkey kidney CVI line transformed by SV40 (COS-7, ATCC CRL 1651); human embryonic kidney line 293S (Graham et al., *J. Gen. Virol.*, 36:59 [1977]); baby hamster kidney cells (BHK, ATCC CCL 10); Chinese hamster ovary cells (Urlab and Chasin, *Proc. Natl. Acad. Sci USA* 77:4216 [1980]); mouse sertoli cells (TM4, Mather, *Biol. Reprod.*, 23:243 [1980]); monkey kidney cells (CVI-76, ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor cells (MMT 060562, ATCC CCL 51); rat hepatoma cells (HTC, MI.54, Baumann et al., *J. Cell Biol.*, 85:1 [1980]); and TRI cells (Mather et al., *Annals N.Y. Acad. Sci.*, 383:44 [1982]). Expression vectors for these cells ordinarily include (if necessary) DNA sequences for an origin of replication, a promoter located in front of the gene to be expressed, a ribosome binding site, an RNA splice site, a polyadenylation site, and a transcription terminator site.

Promoters used in mammalian expression vectors are often of viral origin. These viral promoters are commonly derived from polyoma virus, Adenovirus 2, and most frequently Simian Virus 40 (SV40). The SV40 virus contains two promoters that are termed the early and late promoters. These promoters are particularly useful because they are both easily obtained from the virus as one DNA fragment that also contains the viral origin of replication (Fiers et al., *Nature*, 273:113 [1978]). Smaller or larger SV40 DNA fragments may also be used, provided they contain the approximately 250-bp sequence extending from the HindIII site toward the BglI site located in the viral origin of replication.

Alternatively, promoters that are naturally associated with the foreign gene (homologous promoters) may be used provided that they are compatible with the host cell line selected for transformation.

An origin of replication may be obtained from an exogenous source, such as SV40 or other virus (e.g., Polyoma, Adeno, VSV, BPV) and inserted into the cloning vector. Alternatively, the origin of replication may be provided by the host cell chromosomal replication mechanism. If the vector containing the foreign gene is integrated into the host cell chromosome, the latter is often sufficient.

The use of a secondary DNA coding sequence can enhance production levels of (E)-β-farnesene synthase in transformed cell lines. The secondary coding sequence typically comprises the enzyme dihydrofolate reductase (DHFR). The wild-type form of DHFR is normally inhibited by the chemical methotrexate (MTX). The level of DHFR expression in a cell will vary depending on the amount of MTX added to the cultured host cells. An additional feature of DHFR that makes it particularly useful as a secondary sequence is that it can be used as a selection marker to identify transformed cells. Two forms of DHFR are available for use as secondary sequences, wild-type DHFR and MTX-resistant DHFR. The type of DHFR used in a particular host cell depends on whether the host cell is DHFR deficient (such that it either produces very low levels of DHFR endogenously, or it does not produce functional DHFR at all). DHFR-deficient cell lines such as the CHO cell line described by Urlaub and Chasin, supra, are transformed with wild-type DHFR coding sequences. After transformation, these DHFR-deficient cell lines express functional DHFR and are capable of growing in a culture medium lacking the nutrients hypoxanthine, glycine and thymidine. Nontransformed cells will not survive in this medium.

The MTX-resistant form of DHFR can be used as a means of selecting for transformed host cells in those host cells that endogenously produce normal amounts of functional DHFR that is MTX sensitive. The CHO-K1 cell line (ATCC No. CL 61) possesses these characteristics, and is thus a useful cell line for this purpose. The addition of MTX to the cell culture medium will permit only those cells transformed with the DNA encoding the MTX-resistant DHFR to grow. The nontransformed cells will be unable to survive in this medium.

Prokaryotes may also be used as host cells for the initial cloning steps of this invention. They are particularly useful for rapid production of large amounts of DNA, for production of single-stranded DNA templates used for site-directed mutagenesis, for screening many mutants simultaneously, and for DNA sequencing of the mutants generated. Suitable prokaryotic host cells include E. coli K12 strain 94 (ATCC No. 31,446), E. coli strain W3110 (ATCC No. 27,325) E. coli X1776 (ATCC No. 31,537), and E. coli B; however many other strains of E. coli, such as HB101, JM101, NM522, NM538, NM539, and many other species and genera of prokaryotes including bacilli such as Bacillus subtilis, other enterobacteriaceae such as Salmonella typhimurium or Serratia marcesans, and various Pseudomonas species may all be used as hosts. Prokaryotic host cells or other host cells with rigid cell walls are preferably transformed using the calcium chloride method as described in section 1.82 of Sambrook et al., supra. Alternatively, electroporation may be used for transformation of these cells. Prokaryote transformation techniques are set forth in Dower, W. J., in Genetic Engineering, Principles and Methods, 12:275–296, Plenum Publishing Corp., 1990; Hanahan et al., Meth. Enzymol., 204:63 (1991).

As a representative example, cDNA sequences encoding (E)-β-farnesene synthase may be transferred to the $(His)_6$. Tag pET vector commercially available (from Novagen) for overexpression in E. coli as heterologous host. This pET expression plasmid has several advantages in high level heterologous expression systems. The desired cDNA insert is ligated in frame to plasmid vector sequences encoding six histidines followed by a highly specific protease recognition site (thrombin) that are joined to the amino terminus codon of the target protein. The histidine "block" of the expressed fusion protein promotes very tight binding to immobilized metal ions and permits rapid purification of the recombinant protein by immobilized metal ion affinity chromatography. The histidine leader sequence is then cleaved at the specific proteolysis site by treatment of the purified protein with thrombin, and the (E)-β-farnesene synthase again purified by immobilized metal ion affinity chromatography, this time using a shallower imidazole gradient to elute the recombinant synthases while leaving the histidine block still adsorbed. This overexpression-purification system has high capacity, excellent resolving power and is fast, and the chance of a contaminating E. coil protein exhibiting similar binding behavior (before and after thrombin proteolysis) is extremely small. As will be apparent to those skilled in the art, any plasmid vectors containing replicon and control sequences that are derived from species compatible with the host cell may also be used in the practice of the invention. The vector usually has a replication site, marker genes that provide phenotypic selection in transformed cells, one or more promoters, and a polylinker region containing several restriction sites for insertion of foreign DNA. Plasmids typically used for transformation of E. coli include pBR322, pUC18, pUC19, pUCI18, pUCI19, and Bluescript M13, all of which are described in sections 1.12–1.20 of Sambrook et al., supra. However, many other suitable vectors are available as well. These vectors contain genes coding for ampicillin and/or tetracycline resistance which enables cells transformed with these vectors to grow in the presence of these antibiotics.

The promoters most commonly used in prokaryotic vectors include the β-lactamase (penicillinase) and lactose promoter systems (Chang et al. Nature, 375:615 [1978]; Itakura et al., Science, 198:1056 [1977]; Goeddel et al., Nature, 281:544 [1979]) and a tryptophan (trp) promoter system (Goeddel et al., Nucl. Acids Res., 8:4057 [1980]; EPO Appl. Publ. No. 36,776), and the alkaline phosphatase systems. While these are the most commonly used, other microbial promoters have been utilized, and details concerning their nucleotide sequences have been published, enabling a skilled worker to ligate them functionally into plasmid vectors (see Siebenlist et al., Cell, 20:269 [1980]).

Many eukaryotic proteins normally secreted from the cell contain an endogenous secretion signal sequence as part of the amino acid sequence. Thus, proteins normally found in the cytoplasm can be targeted for secretion by linking a signal sequence to the protein. This is readily accomplished by ligating DNA encoding a signal sequence to the 5' end of the DNA encoding the protein and then expressing this fusion protein in an appropriate host cell. The DNA encoding the signal sequence may be obtained as a restriction fragment from any gene encoding a protein with a signal sequence. Thus, prokaryotic, yeast, and eukaryotic signal sequences may be used herein, depending on the type of host cell utilized to practice the invention. The DNA and amino acid sequence encoding the signal sequence portion of several eukaryotic genes including, for example, human growth hormone, proinsulin, and proalbumin are known (see Stryer, Biochemistry W.H. Freeman and Company, New York, N.Y., p. 769 [1988]), and can be used as signal sequences in appropriate eukaryotic host cells. Yeast signal sequences, as for example acid phosphatase (Arima et al., Nuc. Acids Res., 11:1657 [1983]), α-factor, alkaline phosphatase and invertase may be used to direct secretion from yeast host cells. Prokaryotic signal sequences from genes encoding, for example, LamB or OmpF (Wong et al., Gene, 68:193 [1988]), MalE, PhoA, or beta-lactamase, as well as other genes, may be used to target proteins from prokaryotic cells into the culture medium.

Trafficking sequences from plants, animals and microbes can be employed in the practice of the invention to direct the (E)-β-farnesene synthase proteins of the present invention to the cytoplasm, endoplasmic reticulum, mitochondria or other cellular components, or to target the protein for export to the medium. These considerations apply to the overexpression of (E)-β-farnesene synthase, and to direction of expression within cells or intact organisms to permit gene product function in any desired location.

The construction of suitable vectors containing DNA encoding replication sequences, regulatory sequences, phenotypic selection genes and the (E)-β-farnesene synthase DNA of interest are prepared using standard recombinant DNA procedures. Isolated plasmids and DNA fragments are cleaved, tailored, and ligated together in a specific order to generate the desired vectors, as is well known in the art (see, for example, Sambrook et al., supra).

As discussed above, (E)-β-farnesene synthase variants are preferably produced by means of mutation(s) that are generated using the method of site-specific mutagenesis. This method requires the synthesis and use of specific oligonucleotides that encode both the sequence of the desired mutation and a sufficient number of adjacent nucleotides to allow the oligonucleotide to stably hybridize to the DNA template.

The foregoing may be more fully understood in connection with the following representative examples, in which "Plasmids" are designated by a lower case p followed by an alphanumeric designation. The starting plasmids used in this invention are either commercially available, publicly available on an unrestricted basis, or can be constructed from such available plasmids using published procedures. In addition, other equivalent plasmids are known in the art and will be apparent to the ordinary artisan.

"Digestion", "cutting" or "cleaving" of DNA refers to catalytic cleavage of the DNA with an enzyme that acts only at particular locations in the DNA. These enzymes are called restriction endonucleases, and the site along the DNA sequence where each enzyme cleaves is called a restriction site. The restriction enzymes used in this invention are commercially available and are used according to the instructions supplied by the manufacturers. (See also sections 1.60–1.61 and sections 3.38–3.39 of Sambrook et al., supra.)

"Recovery" or "isolation" of a given fragment of DNA from a restriction digest means separation of the resulting DNA fragment on a polyacrylamide or an agarose gel by electrophoresis, identification of the fragment of interest by comparison of its mobility versus that of marker DNA fragments of known molecular weight, removal of the gel section containing the desired fragment, and separation of the gel from DNA. This procedure is known generally. For example, see Lawn et al. (*Nucleic Acids Res.*, 9:6103–6114 [1982]), and Goeddel et al. (*Nucleic Acids Res.*, supra).

The following examples merely illustrate the best mode now contemplated for practicing the invention, but should not be construed to limit the invention.

EXAMPLE 1

Essential Oil Analysis and Cell-Free Assay

Plant Material and Reagents. Unless stated otherwise, the following plant materials and reagents were used in the experiments reported in this and succeeding Examples. *Mentha x piperita* L. cv. 'Black Mitcham' was propagated from rhizomes as previously described (Gershenzon, J., McCaskill, D., Rajaonarivony, J. I. M., Mihaliak, C., Karp, F. and Croteau, R. (1992) *Anal. Biochem.* 200, 130–138). The preparations of [1-$^3$H]geranyl diphosphate (GDP) (250 Ci/mol), [1-$^3$H]farnesyl diphosphate (FDP) (125 Ci/mol), and [1-$^3$H]geranylgeranyl diphosphate (GGDP) (118 Ci/mol) have been previously reported (Croteau, R., Alonso, W. R., Koepp, A. E. and Johnson, M. A. (1994) *Arch. Biochem. Biophys.* 309, 184–192; Dixit, V. M., Laskovics, F. M., Noall, W. I. and Poulter, C. D. (1981) *J. Org. Chem.* 46, 1967–1969; LaFever, R. E., StoferVogel, B. and Croteau, R. (1994) *Arch. Biochem. Biophys.* 313, 139–149). Terpenoid standards were from our own collection or were prepared from plant material purchased locally. α-Farnesene was a gift from Dr. J. Brown (Washington State University), δ-cadinene was a gift from Dr. M. Essenberg (Oklahoma State University), and commercially steam distilled peppermint oil was a gift from I. P. Callison and Sons, Inc., Chehalis, Wash. All other biochemicals and reagents were purchased from Sigma Chemical Co. or Aldrich Chemical Co., unless otherwise noted.

Sesquiterpene Analysis. Unless stated otherwise, the following procedure was utilized to analyze sesquiterpene content and composition in the experiments reported in this and succeeding Examples. Young, mature peppermint leaves were harvested and hydrodistilled from $NH_4HCO_3$-buffered water with simultaneous pentane extraction (Maarse, H. and Kepner, R. E. (1970) *J. Agr. Chem.* 18, 1095–1101). The organic phase was passed through a column of $MgSO_4$-silica gel (Mallinckrodt SilicAR-60) to provide the olefin fraction for GC-MS analysis. Authentic (E)-β-farnesene was prepared by pentane extraction (followed by silica gel fractionation) of macerated ginger (*Zingiber officinale*) root, black pepper oleoresin (*Piper nigrum*), bergamot oil (*Citrus bergamot*), parsley oil (*Petroselinum crispum*), or field-grown (Yakima Valley, Wash.) commercial peppermint oil (Lawrence, B. M. (1972) *Ann. Acad. Bras. Cienc.* 44, (suppl.), 191–197); all of these sources are reported to contain (E)-β-farnesene.

Instrumental Analysis. The following instrumentation was utilized in this Example and all succeeding Examples, unless stated otherwise. Radio-GC was performed on a Gow-Mac 550P instrument (He carrier 40 ml/min, injector 220° C., detector 250° C. and 150 mA) attached to a Packard 894 gas proportional counter. The column (3.18 mm i.d. by 3.66 m stainless steel with 15% polyethylene glycol ester (AT1000 Alltech) on Gas Chrom Q was programmed from 150° C. (5 min. hold) to 220° C. at 5° C./min. Thermal conductivity and radioactivity outputs were monitored after calibration with an external radiochemical standard, and ~20,000 dpm of tritiated product was injected with data analysis using Turbochrome Navigator ver. 4.1 software (Perkin-Elmer). Liquid scintillation counting was performed in toluene:ethanol (70:30, v/v) containing 0.4% Omnifluor (DuPont NEN) using a Packard 460 CD spectrometer ($^3$H efficiency ~43%). GC-MS analysis employed a Hewlett-Packard 6890-5972 system with a 5MS capillary column (0.25 mm i.d. by 30 m with 0.25 Tm coating of 5% phenyl methyl siloxane). Injections were made cool on-column at 40° C. with oven programming from 40° C. (50° C./min) to 50° C. (5 min hold), then 10° C./min to 250° C., then 50° C./min to 300° C. Separations were made under a constant flow of 0.7 ml He/min. Mass spectral data were collected at 70 eV and analyzed using Hewlett-Packard Chemstation software.

Cell-Free Assays. Peppermint oil gland secretory cells were isolated from immature leaves as previously described (Gershenzon, J., McCaskill, D., Rajaonarivony, J. I. M., Mihaliak, C., Karp, F. and Croteau, R. (1992) *Anal. Biochem.* 200, 130–138, incorporated herein by reference) and sonically disrupted (Braun-Sonic 2000 microprobe at maximum power for three 30-second bursts with 30-second chilling period at 0–4° C. between bursts) into assay buffer consisting of 25 mM Mopso (pH 7.0), 10 mM sodium ascorbate, 25 mM KCl, 10 mM DTT and 10% glycerol, and supplemented with 0.5% (w/v) PVPP and 1% (w/v) Amberlite XAD-4 polystyrene resin. The sonicate was centrifuged at 3700×g for 15 minutes, and an aliquot of the supernatant was then placed in a 10 ml screw-capped glass test tube containing divalent metal ions (10 mM $MgCl_2$ and 1 mM $MnCl_2$) and substrate (7.3 μM [1-$^3$H]FDP). The aqueous layer was overlaid with 1 ml pentane and the sealed tube was incubated at 30° C. for two hours. The pentane overlay was then collected and the aqueous layer was extracted twice (1 ml) with pentane. The combined pentane extracts were passed through an anhydrous $MgSO_4$-silica gel column to obtain the labeled hydrocarbon fraction for GC-MS analysis, or for radio-GC analysis using peppermint oil as an internal standard.

Essential Oil Analysis. To assess the probable abundance of (E)-β-farnesene synthase in peppermint gland secretory cells, the exclusive site of essential oil biosynthesis (Gershenzon, J., McCaskill, D., Rajaonarivony, J. I. M., Mihaliak, C., Karp, F. and Croteau, R. (1992) *Anal. Biochem.* 200, 130–138), the sesquiterpene olefin fraction of field-distilled peppermint oil was analyzed by GC-MS and shown to contain β-caryophyllene (39%), γ-cadinene (33%), β-bourbonene (11%), (E)-β-farnesene (2.9%), δ-cadinene (2.0%), germacrene D (1.3%), copaene (1.3%) and α-humulene (1.2%) (FIG. 1), as well as several other minor components (<1% each). GC-MS analysis of the oil distilled from greenhouse material revealed a similar composition, except that the amount of γ-cadinene was higher (53%), β-bourbonene was conspicuously absent, and the (E)-β-farnesene content was 3.4%. Although (E)-β-farnesene was not one of the more prominent sesquiterpenes of peppermint, the abundance was sufficient to suggest that cloning of the corresponding synthase by random sequencing of an enriched, oil gland cDNA library might be possible.

Figure 2:
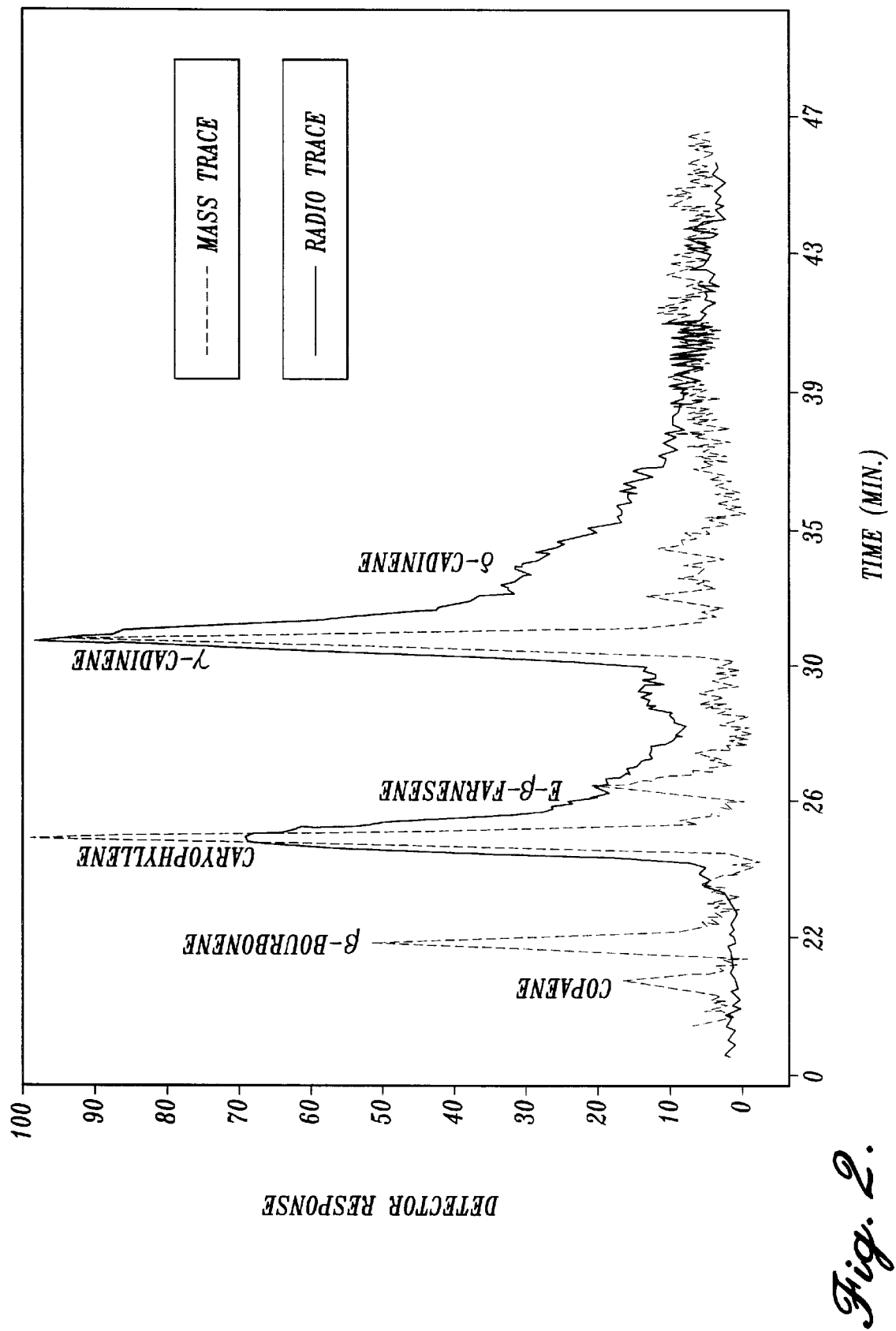
FIG. 2. Radio-GC of the sesquiterpene olefins generated from [1-$^3$H]farnesyl diphosphate by an enzyme preparation from peppermint oil gland secretory cells. The olefin fraction of steam-distilled peppermint oil was used as internal standard, and only the portion of the chromatogram containing the sesquiterpene olefins is shown.
Figure 3A:
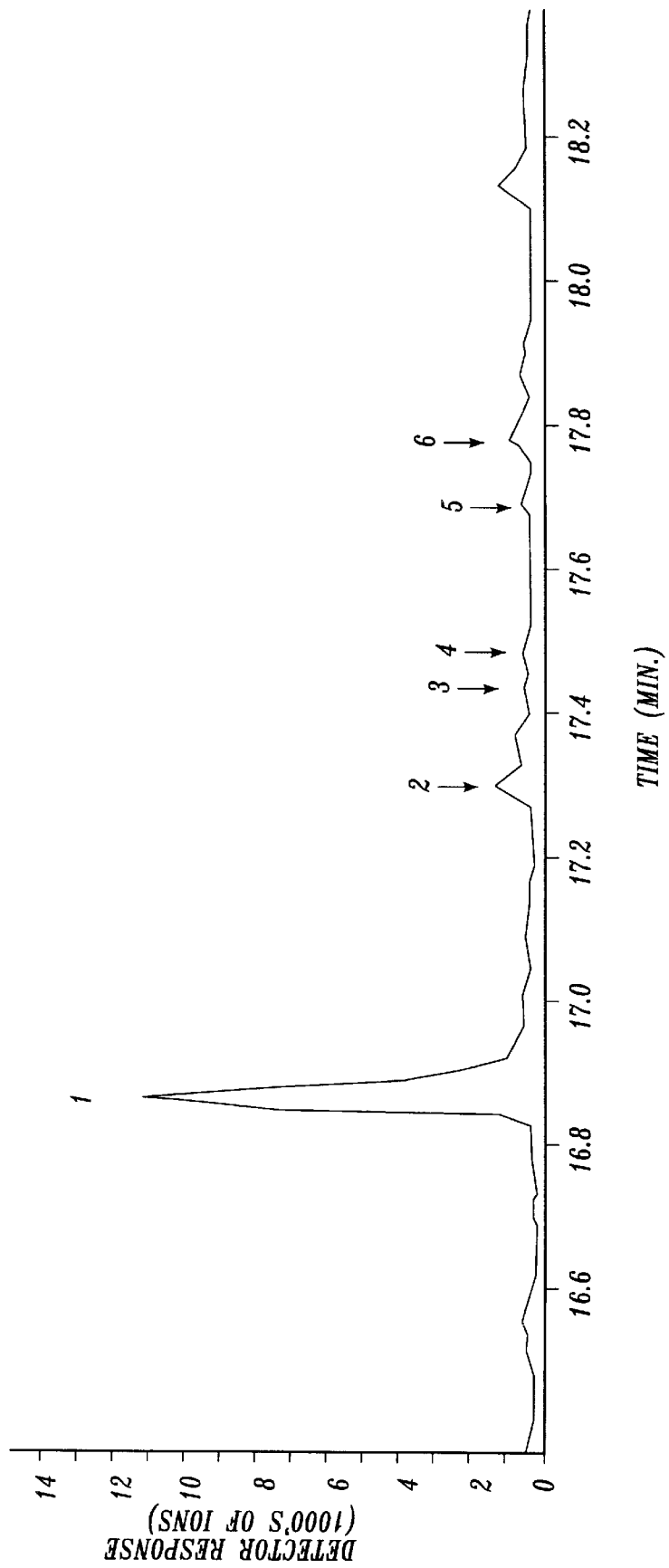
FIG. 3A. GC-MS of the products generated from farnesyl diphosphate by the recombinant (E)-β-farnesene synthase. Panel A: Total ion chromatogram. Numbered peaks are sesquiterpene olefins.
Figure 3B:
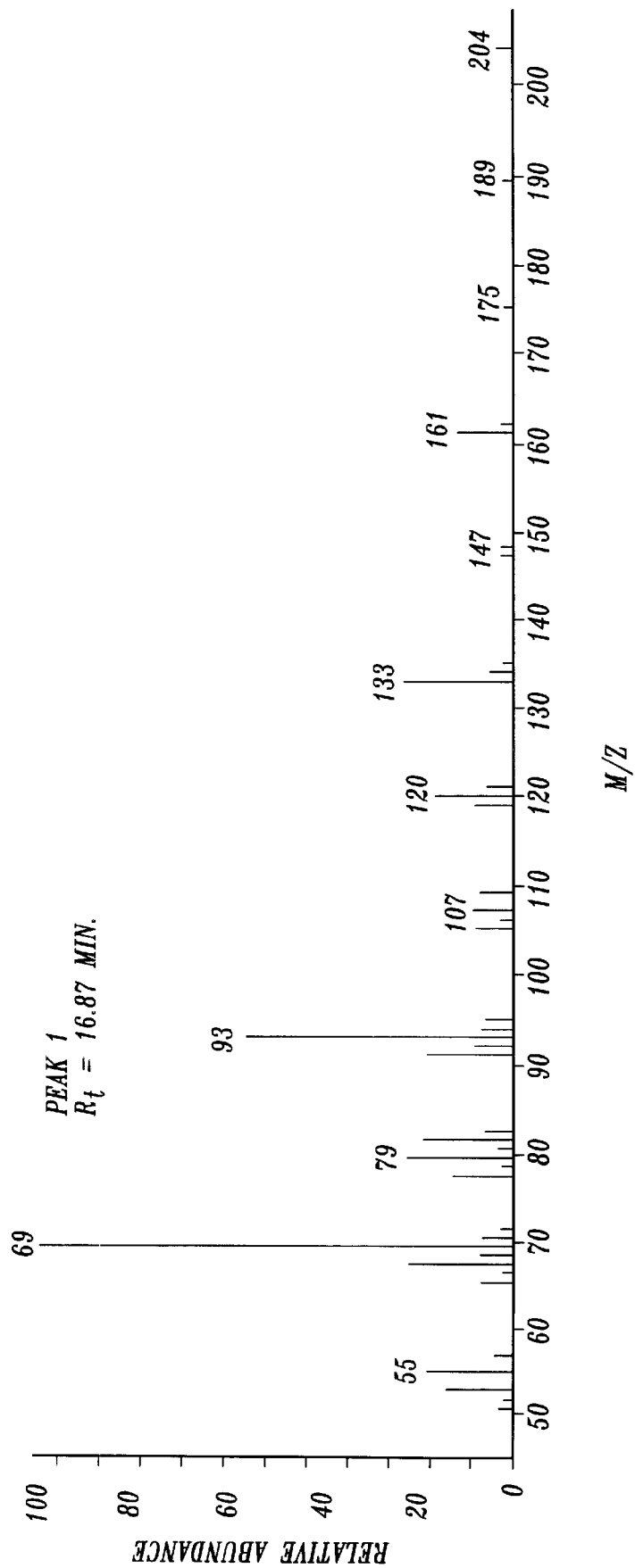
FIG. 3B. Mass spectrum and retention time of peak 1 designated in FIG. 3A.
Figure 3C:
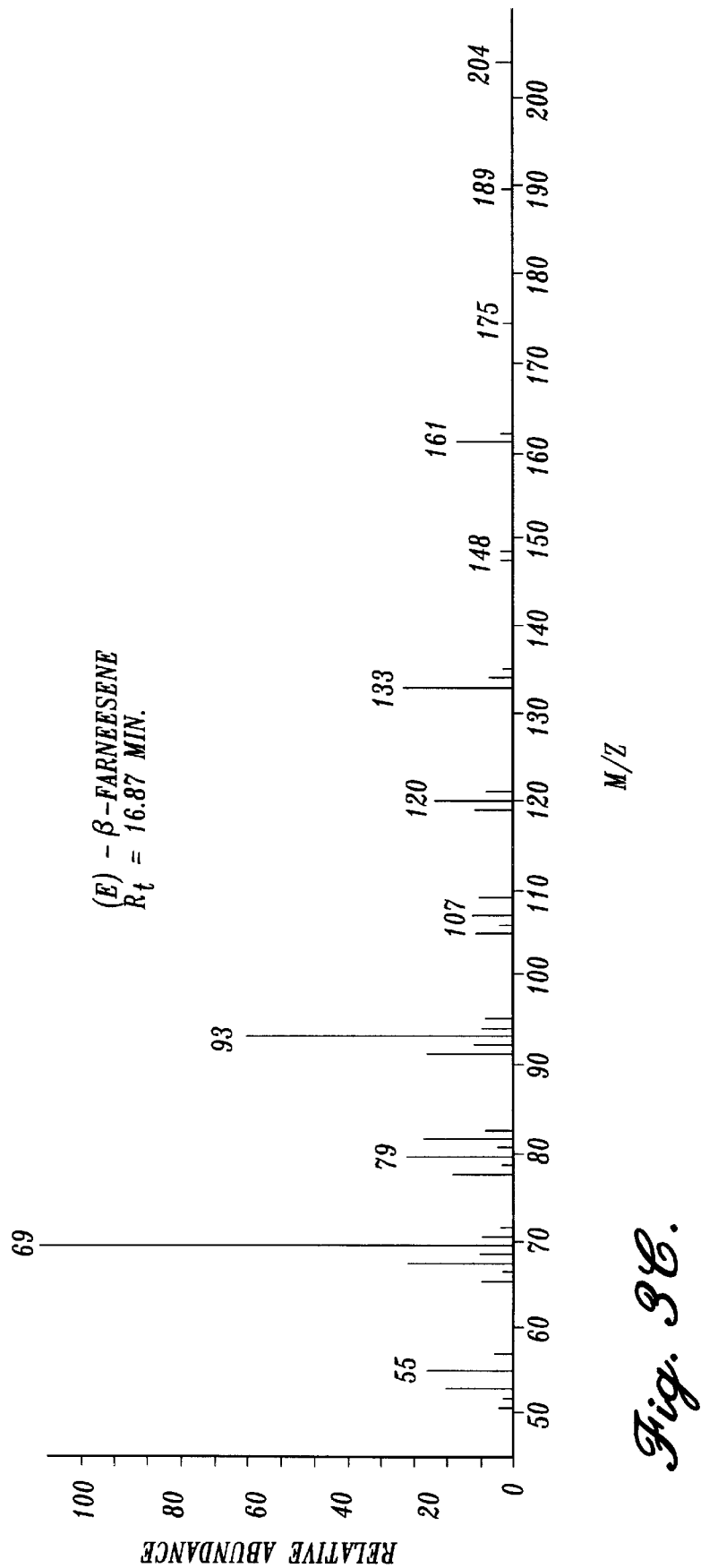
FIG. 3C. Mass spectrum and retention time of authentic (E)-β-farnesene from parley oil.
Figure 3D:
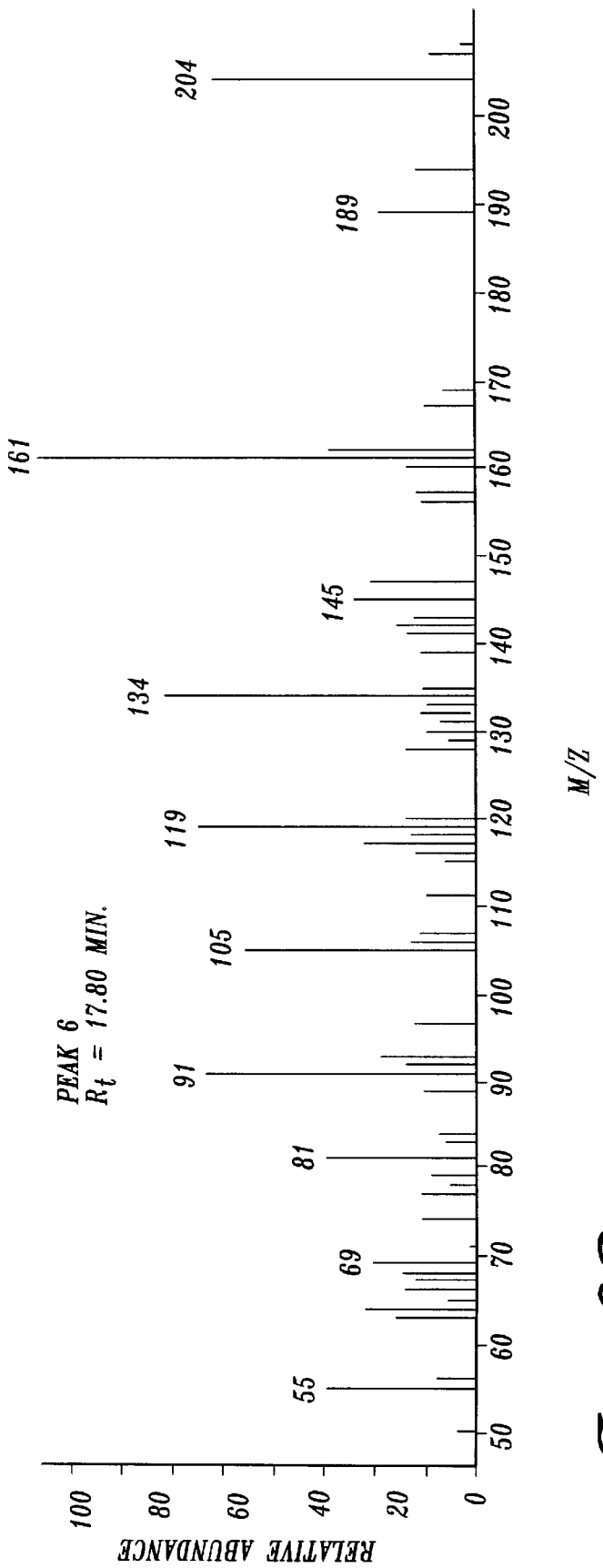
FIG. 3D. Mass spectrum and retention time of peak 6 designated in FIG. 3A. The spectrum of this minor product is compromised by the low ion abundance and the corresponding prominence of background ions.
Figure 3E:
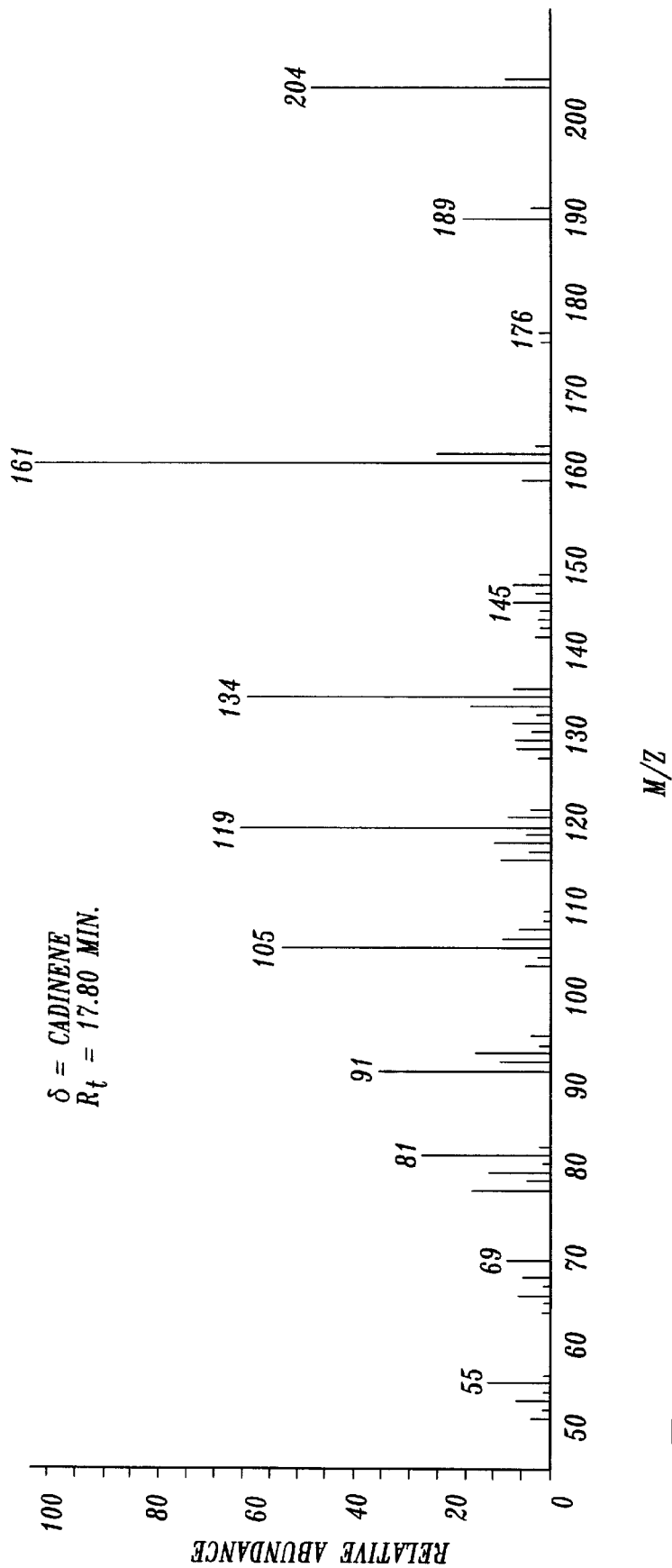
FIG. 3E. Mass spectrum and retention time of authentic δ-cadinene.

Cell-free extracts. To gain a preliminary assessment of the target activity, cell-free extracts of peppermint oil gland secretory cells (Gershenzon, J., McCaskill, D., Rajaonarivony, J. I. M., Mihaliak, C., Karp, F. and Croteau, R. (1992) *Anal. Biochem.* 200, 130–138), were assayed for the divalent metal ion-dependent conversion of [1-$^3$H] farnesyl diphosphate to sesquiterpene olefins (Cane, D. E. (1990) *Chem. Rev.* 90, 1089–1103). Radio-GC analysis of the derived biosynthetic products (FIG. 2) revealed the presence of two major components identified as caryophyllene and γ-cadinene. However, the separation of the labeled olefins was insufficient to resolve (E)-β-farnesene from caryophyllene, or δ-cadinene-from γ-cadinene. Both of these minor components appear at the trailing edges of the major peaks but are, nevertheless, coincident with the authentic standards, indicating the corresponding biosynthetic capability. No β-bourbonene was synthesized from FDP by this system.

EXAMPLE 2

Cloning and Expression in *E. coli* of a cDNA Encoding (E)-β-Farnesene Synthase (SEQ ID NO:1)

Library Construction and Clone Identification. Initial cloning of full-length terpenoid biosynthetic genes from the peppermint oil gland cDNA library was successful and established a very high degree of enrichment for these target sequences. For example, the monoterpene cyclase, limonene synthase (Colby, S. M., Alonso, W. R., Katahira, E. J., McGarvey, D. J. and Croteau, R. (1993) *J. Biol. Chem.* 268, 23016–23024), represents approximately 4% of the library. This fact, plus the availability of automated sequencing capability, led to the possibility of randomly sequencing the library in search of cDNA species encoding other terpenoid synthases, including the (E)-β-farnesene synthase which was shown to be operational in this plant by both sesquiterpene analysis and cell-free assay.

An enriched cDNA library was constructed from peppermint secretory cell clusters consisting of the eight glandular cells subtending the oil droplet. These cell clusters were harvested by a leaf surface abrasion technique (Gershenzon, J., McCaskill, D., Rajaonarivony, J. I. M., Mihaliak, C., Karp, F. and Croteau, R. (1992) *Anal. Biochem.* 200, 130–138), and the RNA contained therein was isolated using the protocol of Logemann et al. (Logemann, J., Schell, J. and Willmitzer, L. (1987) *Anal. Biochem.* 163, 16–20). mRNA was purified by oligo-dT cellulose chromatography (Pharmacia), and 5 μg of mRNA was used to construct a λZAPII cDNA library according to the manufacturer's instructions (Stratagene).

Plasmids were excised from the library en mass and used to transform *E. coli* strain XLOLR as per the manufacturer's instructions (Stratagene). Approximately 150 individual plasmid-bearing strains were grown in 5 ml LB media overnight, and the corresponding plasmids were purified using a Qiawell 8 Ultraplasmid Kit (Qiagen) before partial 5'-sequencing by the Dye-Deoxy™ method using an ABI Sequenator at the Laboratory for Biotechnology and Bioanalysis at Washington State University. Putative terpenoid synthase genes were identified by sequence comparison using the BLAST program of the GCG Wisconsin Package ver. 8. Bluescript plasmids harboring unique full-length cDNA inserts with high similarity to known plant terpenoid synthases were tested for functional expression following transformation into *E. coli* XL1-Blue cells. A single extract, from the bacteria containing clone p43, including the cDNA insert sequence set forth in SEQ ID NO:1, produced a sesquiterpene olefin from [1-$^3$H]FDP, and this clone was selected for further study.

Bacterial Expression and Characterization of (E)-β-Farnesene Synthase (SEQ ID NO:2). *E. coli* XL1-Blue harboring p43 (including the cDNA insert sequence set forth in SEQ ID NO:1), or empty pBluescript plasmid as a control, were grown overnight at 37° C. in LB medium containing 100 μg ampicillin/ml. A 50 μl aliquot of the overnight culture was used to inoculate 5 ml of fresh LB medium, and the culture was grown at 37° C. with vigorous agitation to $A_{600}$ 0.5 before induction with 1 mM IPTG. After an additional two hours of growth, the suspension was centrifuged (1000× g, 15 min, 4° C.), the media removed, and the pelleted cells resuspended in 1 ml of cold assay buffer containing 1 mM EDTA. The cells were disrupted by sonication with a microprobe as previously described, except that only two 20-second bursts were employed. The chilled sonicate was cleared by centrifugation and the supernatant was assayed for sesquiterpene synthase activity as before, or for monoterpene synthase activity (with 4.5 μM [1-$^3$H]GDP) or diterpene synthase activity (with 10 μM [1-$^3$H]GGDP). In all cases, the pentane-soluble reaction products were purified by MgSO$_4$-silica gel chromatography, as above, to prepare the olefin fraction for further analysis.

A cell-free extract of *E. coli* XL-1 Blue cells harboring the plasmid p43 (including the cDNA insert sequence set forth in SEQ ID NO:1) was prepared and shown to be capable of catalyzing the divalent metal ion-dependent conversion of [1-$^3$H]FDP to labeled sesquiterpene olefins. Radio-GC analysis (data not shown) and GC-MS analysis (FIG. 3) of this sesquiterpene olefin fraction demonstrated that the major biosynthetic product (85%) was (E)-β-farnesene by matching of both retention time and mass spectrum to those of the authentic standard obtained from several natural sources. Lesser amounts of (Z)-β-farnesene (8%) and δ-cadinene (5%), as well as three other minor products (less than 1% each; all seemingly of the cadinene-type based on MS), were also produced. Control reactions, employing extracts of XL1-Blue cells transformed with pBluescript lacking the cDNA insert having the sequence set forth in SEQ ID NO:1, evidenced no detectable production of sesquiterpene olefins from [1-$^3$H]FDP, thereby demonstrating that a cDNA clone encoding (E)-β-farnesene synthase had been acquired.

Figure 4:
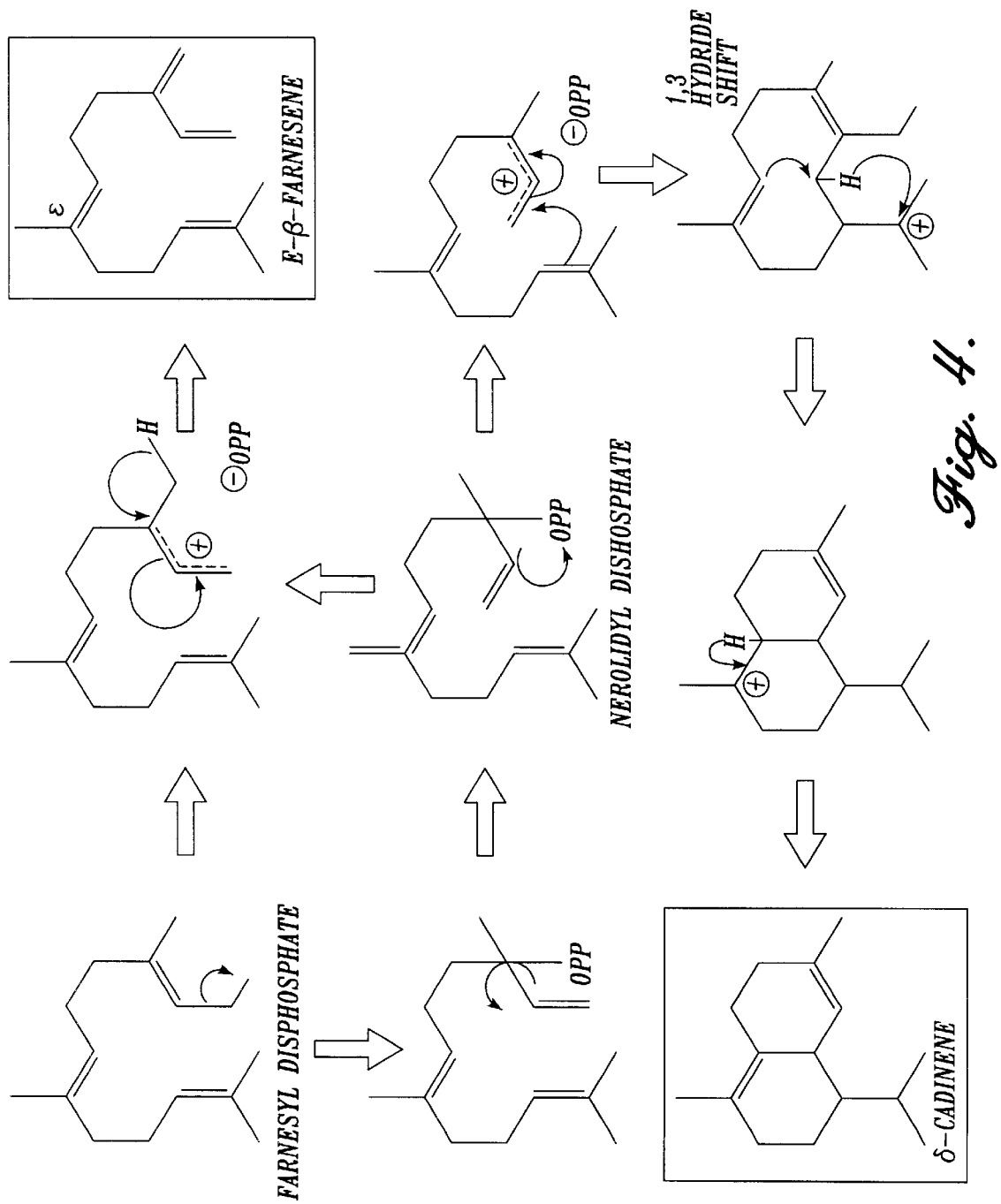
FIG. 4. Proposed mechanism for the formation of (E)-β-farnesene and δ-cadinene from farnesyl diphosphate. OPP denotes the diphosphate moiety. Ionization of the enzyme-bound nerolidyl diphosphate intermediate and proton elimination can also produce (E)-β-farnesene.

Multiple product formation is a common feature of the terpenoid synthases, and may be a consequence of the electrophilic reaction mechanism catalyzed by these enzymes in which highly reactive carbocationic intermediates are generated (Cane, D. E. (1990) *Chem. Rev.* 90, 1089–1103; Croteau, R. (1987) *Chem. Rev.* 87, 929–954). (E)-β-farnesene is one of the simplest sesquiterpene olefins that can be derived from FDP, in a reaction involving divalent metal ion-assisted ionization of the diphosphate ester and deprotonation from the C-3 methyl of the resulting carbocation (FIG. 4). The formation of δ-cadinene (FIG. 4) involves a considerably more extended reaction sequence, in which a preliminary isomerization step (to nerolidyl diphosphate) is required to permit the ionization-dependent cyclization to the macrocycle, followed by 1,3-hydride shift, closure of the second ring, and deprotonation to the bicyclic product. The small amount of δ-cadinene produced by the recombinant synthase (SEQ ID NO:2) from FDP is interesting in light of the abundance of this bicyclic olefin in the sesquiterpene fraction of peppermint oil and the efficient production of this olefin in oil gland extracts; these observations suggest that an additional and distinct δ-cadinene synthase must operate in peppermint.

Figure 5:
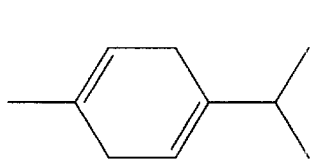
FIG. 5. Monoterpene olefins generated from the alternate substrate geranyl diphosphate by recombinant (E)-β-farnesene synthase.
Figure 5:
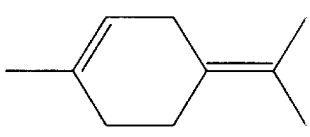
Figure 5:
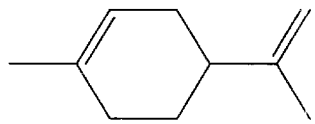
Figure 5:
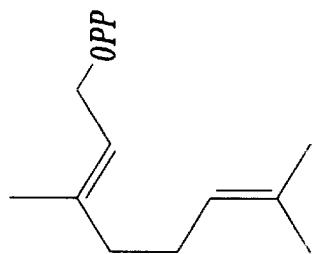
Figure 5:
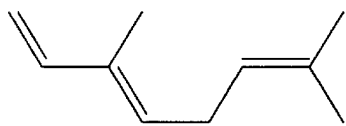
Figure 5:
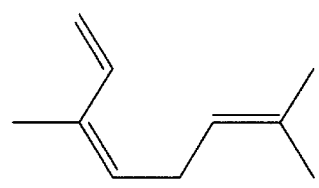
Figure 5:
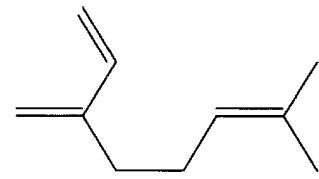
Figure 5:
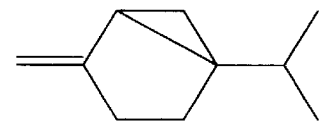

The recombinant (E)-β-farnesene synthase (SEQ ID NO:2) was inactive with the $C_{20}$ substrate analog [1-$^3$H] GGDP, but was able to catalyze the divalent cation-dependent conversion of the $C_{10}$ analog [1-$^3$H]GDP to monoterpene olefins. Although the rate of conversion of GDP to these products was less than 3% of the rate of conversion of FDP to sesquiterpene olefins at saturation, a more diverse spectrum of products was formed (see FIG. 5 for structures). The cyclic monoterpenes limonene (48%) and terpinolene (15%), and the acyclic monoterpene analog of β-farnesene, myrcene (15%), were the most abundant products as determined by both radio-GC and GC-MS analysis (data not shown). Lesser amounts of γ-terpinene (7%), (Z)-ocimene (6%), (E)-ocimene (7%), and sabinene (3%) were also observed as products. Control reactions, employing extracts of XL1-Blue cells transformed with pBluescript lacking the insert, evidenced no detectable production of monoterpene olefins from [1-$^3$H]GDP, thereby confirming that the monoterpene synthase activity expressed from p43 was a function of the (E)-β-farnesene synthase (SEQ ID NO:2). This is the first report describing the utilization of GDP by a sesquiterpene synthase. Because monoterpene biosynthesis is localized to plastids, as is diterpene biosynthesis, whereas sesquiterpene biosynthesis occurs in the cytoplasm (Chappell, J. (1995) *Annu. Rev. Plant Physiol. Plant Mol. Biol.* 46, 521–547), the utilization of GDP as a substrate by (E)-β-farnesene synthase is unlikely to be of physiological relevance and may simply reflect the lack of evolutionary pressure to discern the chain length of this isoprenoid substrate to which the enzyme is not exposed in vivo.

EXAMPLE 3

Sequence Analysis of the p43 cDNA Insert (SEQ ID NO:1)

Complete sequencing of the (E)-β-farnesene synthase cDNA (SEQ ID NO:1) contained in p43 revealed an insert size of 1959 bp encoding an open reading frame of 550 amino acids with a deduced molecular weight of 63,829. A putative starting methionine codon was identified which was out of frame with the vector β-galactosidase starting methionine; however, a fortuitous stop codon in the 5'-untranslated region, 46 bp upstream of the synthase translation start site and in frame with the β-galactosidase fusion sequence, allowed polycistronic translation of the cDNA free of vector-derived sequence. The deduced amino acid sequence of the (E)-β-farnesene synthase (SEQ ID NO:2) lacks a plastidial targeting peptide (Keegstra, K., Olsen, J. J. and Theg, S. M. (1989) *Ann. Rev. Plant Physiol. Plant Mol. Biol.* 40, 471–501), typical of monoterpene and diterpene synthases (Colby, S. M., Alonso, W. R., Katahira, E. J., McGarvey, D. J. and Croteau, R. (1993) *J. Biol. Chem.* 268, 23016–23024; Stofer Vogel, B., Wildung, M. R., Vogel, G. and Croteau, R. (1996) *J. Biol. Chem.* 271, 23262–23268; Wildung, M. R. and Croteau, R. (1996) *J. Biol. Chem.* 271, 9201–9204), but consistent with all known plant-derived sesquiterpene synthases (Fachinni, P. J. and Chappell, J. (1992) *Proc. Natl. Acad Sci. USA* 89, 11088–11092; Back, K. and Chappell, J. (1995) *J. Biol. Chem.* 270, 7375–7381; Chen, X. Y., Chen, Y., Heinstein, P. and Davisson, V. J. (1996) *Arch. Biochem. Biophys.* 324, 255–266) which are directed to the cytoplasm. Like all other known terpenoid synthases, (E)-β-farnesene synthase (SEQ ID NO:2) is rich in tryptophan (1.8%) and arginine (5.5%) residues, and bears a DDXXD motif (residues 301–305)(SEQ ID NO:3) which is believed to coordinate the divalent metal ion chelated to the substrate diphosphate group (Marrero, O. F., Poulter, C. D. and Edwards, P. A. (1992) *J. Biol. Chem.* 267, 21873–21878); the enzyme (SEQ ID NO:2) has a deduced isoelectric point at pH 5.16.

The deduced amino acid sequence of the farnesene synthase (SEQ ID NO:2) is most similar to that of the sesquiterpene cyclase epi-aristolochene synthase from tobacco (Fachinni, P. J. and Chappell, J. (1992) *Proc. Natl. Acad Sci. USA* 89, 11088–11092) in exhibiting 62% similarity (S) and 49% identity (I). This peppermint synthase (SEQ ID NO:2) also closely resembles the three other known angiosperm sesquiterpene cyclases (vetispiradiene synthase from *Hyoscyamus muticus* (Back, K. and Chappell, J. (1995) *J. Biol. Chem.* 270, 7375–7381) at 63% S and 40% I, δ-cadinene synthase from cotton (Chen, X. Y., Chen, Y., Heinstein, P. and Davisson, V. J. (1996) *Arch. Biochem. Biophys.* 324, 255–266) at 60% S and 37% I, and germacrene C synthase from tomato at 57% S and 34% I (unpublished), and also the diterpene cyclase, casbene synthase (Mau, C. J. D. and West, C. A. (1994) *Proc. Natl. Acad. Sci. USA* 91, 8497–8501), from castor bean (at 61% S and 35% I). Since (E)-β-farnesene synthase (SEQ ID NO:2) produces a small amount of δ-cadinene, but cannot be the major source of δ-cadinene in peppermint, it is tempting to speculate that the farnesene synthase (SEQ ID NO:2) represents either a progenitor, or an altered form of cadinene synthase in which the ability to catalyze the more complex bicyclization reaction has been lost.

Surprisingly, (E)-β-farnesene synthase (SEQ ID NO:2) is no more closely related to monoterpene synthases from the Lamiaceae (limonene synthase from spearmint (Colby, S. M., Alonso, W. R., Katahira, E. J., McGarvey, D. J. and Croteau, R. (1993) *J. Biol. Chem.* 268, 23016–23024) with 51% S and 30% I; sabinene synthase and 1,8-cineole synthase from culinary sage with 50% S and 29% I each) than to the various terpenoid synthases from the gymnosperm *Abies grandis* (monoterpene synthases with 49% S and 28% I (Bohlmann, J., Steele, C. L. and Croteau, R. (1997) *J. Biol. Chem.* 272, 21784–21792); sesquiterpene synthases with 53% S and 29% I; diterpene synthases with 51% S and 28% I (Stofer Vogel, B., Wildung, M. R., Vogel, G. and Croteau, R. (1996) *J. Biol. Chem.* 271, 23262–23268). Even a phylogenetically distant diterpene cyclase from *Taxus brevifolia*, taxadiene synthase (Wildung, M. R. and Croteau, R. (1996) *J. Biol. Chem.* 271, 9201–9204), resembles (E)-β-farnesene synthase (SEQ ID NO:2) at the amino acid level (50% S and 24% I) as closely as do the monoterpene synthases of the mint family. These sequence-based relationships may reflect a bifurcation in the evolution of the monoterpene synthases from the higher terpenoid synthases that is as ancient as the separation between the angiosperms and gymnosperms.

EXAMPLE 4

Characterization of (E)-β-Farnesene Synthase (SEQ ID NO:2)

For determination of the pH optimum of (E)-β-farnesene synthase (SEQ ID NO:2), the preparation was adjusted with 50 mM Mopso (to a pH of 6.5, 6.75, 7.0, 7.25, 7.5, 8.0, or 8.5) before the assay. Kinetic constants for FDP, GDP, $Mg^{++}$ and $Mn^{++}$ were determined using a preparation of (E)-β-farnesene synthase (SEQ ID NO:2) that was partially purified by anion-exchange chromatography (on a Mono-Q column (Pharmacia) equilibrated with assay buffer and eluted with a linear KCl gradient (0 to 500 mM) in assay buffer). The 210–230 mM fraction containing the (E)-β-farnesene synthase (SEQ ID NO:2) was used for kinetic evaluation of FDP and GDP as substrates (concentration range 0.31 to 20 μM, with saturating $Mg^{++}$). Due to the tenacious binding of divalent cations by the synthase, the partially purified enzyme (prepared in the presence of 10 mM EDTA) was dialyzed overnight against assay buffer containing 50 mM EDTA. The dialysate was buffer-exchanged by ultrafiltration (Amicon Centriprep 30, 450 fold dilution), then desalted (Bio-Rad Econo-Pak 10 DG) into assay buffer. Kinetic constants for $Mg^{++}$ and $Mn^{++}$ (assay range 1 μM to 2 mM of the chloride salts) were then determined at 7.3 μM [1-$^3$H]FDP. Triplicate assays were conducted and control incubations (without enzyme) were included in all cases. A double reciprocal plot (Lineweaver, H. and Burk, D. (1934) *J. Am. Chem. Soc.* 56, 658–666) was generated for each averaged data set, and the equation of the best-fit line determined (Kaleidagraph ver. 3.08, Synergy Software).

The recombinant, partially purified (E)-β-farnesene synthase (SEQ ID NO:2) exhibited a broad pH optimum in the 6.75 to 7.25 range in Mopso buffer. This observation is in agreement with the studies of Salin et al. (Salin, F., Pauly, G., Charon, J. and Gleizes, M. (1995) *J. Plant Phys.* 146, 203–209) in which the purified (E)-β-farnesene synthase from maritime pine was shown to possess a pH optimum in the 7.0 to 7.3 range. The $K_m$ value for FDP with the recombinant synthase (SEQ ID NO:2) was calculated to be 0.6 μM, a value typical of other sesquiterpene synthases of plant origin (Cane, D. E. (1990) *Chem. Rev.* 90, 1089–1103) but lower than the value of 5 μM determined for the enzyme from maritime pine (Salin, F., Pauly, G., Charon, J. and Gleizes, M. (1995) *J. Plant Phys.* 146, 203–209). Substrate concentrations in excess of 10 μM FDP evidenced slight inhibition of activity with the recombinant enzyme (SEQ ID NO:2). Although the relative velocity at saturating levels of GDP was only 3% of the velocity with FDP for the recombinant synthase (SEQ ID NO:2), the calculated $K_m$ value for GDP (1.5 μM was only three-fold higher than that for FDP, suggesting that the binding of the $C_{10}$ analog was reasonably efficient.

A $K_m$ value of 150 μM was determined for $Mg^{++}$ ($V_{rel}$= 100), and a $K_m$ value of 7.0 μM was determined for $Mn^{++}$ ($V_{rel}$=80). No inhibition of activity was observed at $Mg^{++}$ concentrations up to 10 mM; however, concentrations of $Mn^{++}$ exceeding 20 μM resulted in a sharp decline in reaction velocity to a plateau ($V_{rel}$=20) in the 0.25 to 2 mM range. Since the product distribution of the recombinant (E)-β-farnesene synthase (SEQ ID NO:2) had been initially determined in the presence of excess $Mg^{++}$, the conversion of [1-$^3$H]FDP was re-evaluated in the presence of $Mn^{++}$ alone at apparent saturation (20 μM). The olefin products were again analyzed by GC-MS and found in this case to consist of 98% (E)-β-farnesene and 2% (Z)-β-farnesene. No δ-cadinene, or other sesquiterpenes, were synthesized in this instance, indicating that a structural alteration in the binding of $Mn^{++}$ to the substrate and/or enzyme (relative to $Mg^{++}$) improves the fidelity of the reaction.

In operational characteristics (pH optimum, kinetic constants) and physical features (size, pI), the recombinant (E)-β-farnesene synthase (SEQ ID NO:2) is a typical sesquiterpene synthase (Cane, D. E. (1990) *Chem. Rev.* 90, 1089–1103; Fachinni, P. J. and Chappell, J. (1992) *Proc. Natl. Acad. Sci. USA* 89, 11088–11092; Back, K. and Chappell, J. (1995) *J. Biol. Chem.* 270, 7375–7381; Chen, X. Y., Chen, Y., Heinstein, P. and Davisson, V. J. (1996) *Arch. Biochem. Piophys.* 324, 255–266), suggesting that the enzyme should be highly functional in planta. Given that this synthase (SEQ ID NO:2) will be targeted by default to the cytoplasm (Chappell, J. (1995) *Annu. Rev. Plant Physioll. Plant Mol. Biol.* 46, 521–547; Keegstra, K., Olsen, J. J. and Theg, S. M. (1989) *Ann. Rev. Plant Physiol. Plant Mol. Biol.* 40, 471–501), where the substrate arises from the mevalonate pathway, it should be possible to engineer virtually any plant for the production of (E)-β-farnesene in order to exploit the kairomonal and pheromonal properties of this natural product.

EXAMPLE 5

Properties of (E)-β-Farnesene Synthase Proteins of the Present Invention

The (E)-β-farnesene synthase proteins of the present invention all require a divalent metal ion as a cofactor. Most (E)-β-farnesene synthase proteins of the present invention utilize either $Mg^{++}$ or $Mn^{++}$ as a cofactor. Nonetheless, (E)-β-farnesene synthase proteins of the present invention are inhibited at concentrations of $Mn^{++}$ in excess of about 5 mM.

(E)-β-farnesene synthase proteins of the present invention have a pH optimum in the range of from about pH 5.5 to about pH 8.5, and a pI in the range of from about pH 4.5 to about pH 6.0. The Km(FPP) of (E)-β-farnesene synthase proteins of the present invention is less than about 10 μM, while the Kcat(FPP) of (E)-β-farnesene synthase proteins of the present invention is less than about 5/sec. The (E)-β-farnesene synthase proteins of the present invention exist as either monomers or homodimers, with the monomer having a molecular weight of from about 55 kD (kiloDaltons) to about 65 kD.

EXAMPLE 6

Hybridization of Peppermint (E)-β-Farnesene Synthase cDNA (SEQ ID NO:1) to Other Nucleic Acid Sequences of the Present Invention The nucleic acid molecules of the present invention are capable of hybridizing to the nucleic acid sequence set forth in SEQ ID NO:1, or to the complementary sequence of the nucleic acid sequence set forth in SEQ ID NO:1, under the following stringent hybridization conditions: incubation in 5×SSC at 65° C. for 16 hours, followed by washing under the following conditions: two washes in 2×SSC at 18° C. to 25° C. for twenty minutes per wash; preferably, two washes in 2×SSC at 18° C. to 25° C. for twenty minutes per wash, followed by one wash in 0.5×SSC at 55° C. for thirty minutes; most preferably, two washes in 2×SSC at 18° C. to 25° C. for fifteen minutes per wash, followed by two washes in 0.2×SSC at 65° C. for twenty minutes per wash.

The ability of the nucleic acid molecules of the present invention to hybridize to the nucleic acid sequence set forth in SEQ ID NO:1, or to the complementary sequence of the nucleic acid sequence set forth in SEQ ID NO:1, can be determined utilizing the technique of hybridizing radiolabelled nucleic acid probes to nucleic acids immobilized on nitrocellulose filters or nylon membranes as set forth, for example, at pages 9.52 to 9.55 of Molecular Cloning, A Laboratory Manual (2nd edition), J. Sambrook, E. F. Fritsch and T. Maniatis eds, the cited pages of which are incorporated herein by reference.

In addition to the nucleic acid sequence set forth in SEQ ID NO:1, examples of representative nucleic acid sequences of the present invention that encode a peppermint (E)-β-farnesene synthase protein and which hybridize to the complementary sequence of the nucleic acid sequence disclosed in SEQ ID NO:1 are set forth in SEQ ID NO:4; SEQ ID NO:6; SEQ ID NO:8; SEQ ID NO:10; SEQ ID NO:12; SEQ ID NO:14; SEQ ID NO:16 and SEQ ID NO:18. With the exception of the nucleic acid sequence set forth in SEQ ID NO:1, the foregoing representative nucleic acid sequences of the present invention were generated using a computer. By utilizing the degeneracy of the genetic code, each of the foregoing, representative nucleic acid sequences has a different sequence, but each encodes the protein set forth in SEQ ID NO:2. Thus, the identical (E)-β-farnesene synthase protein sequence is set forth in SEQ ID NO:2, SEQ ID NO:5; SEQ ID NO:7; SEQ ID NO:9; SEQ ID NO:11; SEQ ID NO:13; SEQ ID NO:15; SEQ ID NO:17 and SEQ ID NO:19.

In addition to the protein sequence set forth in SEQ ID NO:2 examples of representative (E)-β-farnesene synthase proteins of the present invention are set forth in SEQ ID NO:20; SEQ ID NO:21; SEQ ID NO:22; SEQ ID NO:23; SEQ ID NO:24; SEQ ID NO:25; SEQ ID NO:26, SEQ ID NO:27 and SEQ ID NO:28. With the exception of the amino acid sequence set forth in SEQ ID NO:2, the foregoing representative amino acid sequences of the present invention were generated using a computer by making conservative amino acid substitutions.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. An isolated nucleic acid molecule encoding (E)-β-farnesene synthase protein wherein said nucleic acid sequence consists of SEQ ID NO: 1.

2. An isolated nucleic acid molecule encoding an (E)-β-farnesene synthase protein having the amino acid sequence set forth in SEQ ID NO: 2.

3. A replicable expression vector comprising a nucleic acid sequence consisting of the nucleic acid sequence set forth in SEQ ID NO: 1.

4. A host cell comprising a vector according to claim 3.

5. An isolated nucleic acid molecule that encodes an active (E)-β-farnesene synthase, wherein said nucleic acid hybridizes to the nucleic acid molecule set forth in SEQ ID NO: 1 or its complement under stringent hybridization conditions comprising two twenty minute washes in 0.2× SSC at 65° C.

* * * * *

UNITED STATES PATENT AND TRADEMARK OFFICE
CERTIFICATE OF CORRECTION

PATENT NO. : 6,008,043  
DATED : December 28, 1999  
INVENTOR(S) : R.B. Croteau et al.

It is certified that error appears in the above-identified patent and that said Letters Patent is hereby corrected as shown below:

Column 1,  
Line 9, after "GM-31354" insert -- , --  
Line 10, "96E20212" should read -- 96ER20212 --

Signed and Sealed this

Fifth Day of March, 2002

Attest:

JAMES E. ROGAN  
*Attesting Officer*     *Director of the United States Patent and Trademark Office*

SEQUENCE LISTING

```
<160> NUMBER OF SEQ ID NOS: 28

<210> SEQ ID NO 1
<211> LENGTH: 1959
<212> TYPE: DNA
<213> ORGANISM: Mentha piperita
<220> FEATURE:
<221> NAME/KEY: CDS
<222> LOCATION: (71)..(1720)

<400> SEQUENCE: 1
aaactctgca atttcatata taacatcata aaatcagaga gagagacaga gagtttgttg      60
tagtgaaaaa atg gct aca aac ggc gtc gta att agt tgc tta agg gaa      109
            Met Ala Thr Asn Gly Val Val Ile Ser Cys Leu Arg Glu
              1               5                  10 gta agg cca cct atg acg aag cat gcg cca agc atg tgg act gat acc      157
Val Arg Pro Pro Met Thr Lys His Ala Pro Ser Met Trp Thr Asp Thr
     15                  20                  25 ttt tct aac ttt tct ctt gac gat aag gaa caa caa aag tgc tca gaa      205
Phe Ser Asn Phe Ser Leu Asp Asp Lys Glu Gln Gln Lys Cys Ser Glu
 30                  35                  40                  45 acc atc gaa gca ctt aag caa gaa gca aga ggc atg ctt atg gct gca      253
Thr Ile Glu Ala Leu Lys Gln Glu Ala Arg Gly Met Leu Met Ala Ala
                 50                  55                  60 acc act cct ctc caa caa atg aca cta atc gac act ctc gag cgt ttg      301
Thr Thr Pro Leu Gln Gln Met Thr Leu Ile Asp Thr Leu Glu Arg Leu
             65                  70                  75 gga ttg tct ttc cat ttt gag acg gag atc gaa tac aaa atc gaa cta      349
Gly Leu Ser Phe His Phe Glu Thr Glu Ile Glu Tyr Lys Ile Glu Leu
         80                  85                  90 atc aac gct gca gaa gac gac ggc ttt gat ttg ttc gct act gct ctt      397
Ile Asn Ala Ala Glu Asp Asp Gly Phe Asp Leu Phe Ala Thr Ala Leu
     95                 100                 105 cgt ttc cgt ttg ctc aga caa cat caa cgc cac gtt tct tgt gat gtt      445
Arg Phe Arg Leu Leu Arg Gln His Gln Arg His Val Ser Cys Asp Val
110                 115                 120                 125
```

-continued

| | |
|---|---|
| ttc gac aag ttc atc gac aaa gat ggc aag ttc gaa gaa tcc ctt agc<br>Phe Asp Lys Phe Ile Asp Lys Asp Gly Lys Phe Glu Glu Ser Leu Ser<br>130 135 140 | 493 |
| aat aat gtt gaa ggc cta tta agc ttg tat gaa gca gct cat gtt ggg<br>Asn Asn Val Glu Gly Leu Leu Ser Leu Tyr Glu Ala Ala His Val Gly<br>145 150 155 | 541 |
| ttt cgc gaa gaa aga ata tta caa gag gct gta aat ttt acg agg cat<br>Phe Arg Glu Glu Arg Ile Leu Gln Glu Ala Val Asn Phe Thr Arg His<br>160 165 170 | 589 |
| cac ttg gaa gga gca gag tta gat cag tct cca tta ttg att aga gag<br>His Leu Glu Gly Ala Glu Leu Asp Gln Ser Pro Leu Leu Ile Arg Glu<br>175 180 185 | 637 |
| aaa gtg aag cga gct ttg gag cac cct ctt cat agg gat ttc ccc att<br>Lys Val Lys Arg Ala Leu Glu His Pro Leu His Arg Asp Phe Pro Ile<br>190 195 200 205 | 685 |
| gtc tat gca cgc ctt ttc atc tcc att tac gaa aag gat gac tct aga<br>Val Tyr Ala Arg Leu Phe Ile Ser Ile Tyr Glu Lys Asp Asp Ser Arg<br>210 215 220 | 733 |
| gat gaa tta ctt ctc aag cta tcc aaa gtc aac ttc aaa ttc atg cag<br>Asp Glu Leu Leu Leu Lys Leu Ser Lys Val Asn Phe Lys Phe Met Gln<br>225 230 235 | 781 |
| aat ttg tat aag gaa gag ctc tcc caa ctc tcc agg tgg tgg aac aca<br>Asn Leu Tyr Lys Glu Glu Leu Ser Gln Leu Ser Arg Trp Trp Asn Thr<br>240 245 250 | 829 |
| tgg aat ctg aaa tca aaa tta cca tat gca aga gat cga gtc gtg gag<br>Trp Asn Leu Lys Ser Lys Leu Pro Tyr Ala Arg Asp Arg Val Val Glu<br>255 260 265 | 877 |
| gct tat gtt tgg gga gta ggt tac cat tac gaa ccc caa tac tca tat<br>Ala Tyr Val Trp Gly Val Gly Tyr His Tyr Glu Pro Gln Tyr Ser Tyr<br>270 275 280 285 | 925 |
| gtt cga atg gga ctt gcc aaa ggc gta cta att tgt gga atc atg gac<br>Val Arg Met Gly Leu Ala Lys Gly Val Leu Ile Cys Gly Ile Met Asp<br>290 295 300 | 973 |
| gat aca tat gat aat tat gct aca ctc aat gaa gct caa ctt ttt act<br>Asp Thr Tyr Asp Asn Tyr Ala Thr Leu Asn Glu Ala Gln Leu Phe Thr<br>305 310 315 | 1021 |
| caa gtc tta gac aag tgg gat aga gat gaa gct gaa cga ctc cca gaa<br>Gln Val Leu Asp Lys Trp Asp Arg Asp Glu Ala Glu Arg Leu Pro Glu<br>320 325 330 | 1069 |
| tac atg aaa atc gtt tat cga ttt att ttg agt ata tat gaa aat tat<br>Tyr Met Lys Ile Val Tyr Arg Phe Ile Leu Ser Ile Tyr Glu Asn Tyr<br>335 340 345 | 1117 |
| gaa cgt gat gca gcg aaa ctt gga aaa agc ttt gca gct cct tat ttt<br>Glu Arg Asp Ala Ala Lys Leu Gly Lys Ser Phe Ala Ala Pro Tyr Phe<br>350 355 360 365 | 1165 |
| aag gaa acc gtg aaa caa ctg gca agg gca ttt aat gag gag cag aag<br>Lys Glu Thr Val Lys Gln Leu Ala Arg Ala Phe Asn Glu Glu Gln Lys<br>370 375 380 | 1213 |
| tgg gtt atg gaa agg cag cta ccg tca ttc caa gac tac gta aag aat<br>Trp Val Met Glu Arg Gln Leu Pro Ser Phe Gln Asp Tyr Val Lys Asn<br>385 390 395 | 1261 |
| tca gag aaa acc agc tgc att tat acc atg ttt gct tct atc atc cca<br>Ser Glu Lys Thr Ser Cys Ile Tyr Thr Met Phe Ala Ser Ile Ile Pro<br>400 405 410 | 1309 |
| ggc ttg aaa tct gtt acc caa gaa acc att gat tgg atc aag agt gaa<br>Gly Leu Lys Ser Val Thr Gln Glu Thr Ile Asp Trp Ile Lys Ser Glu<br>415 420 425 | 1357 |
| ccc acg ctc gca aca tcg acc gct atg atc ggt cgg tat tgg aat gac<br>Pro Thr Leu Ala Thr Ser Thr Ala Met Ile Gly Arg Tyr Trp Asn Asp<br>430 435 440 445 | 1405 |
| acc agc tct cag ctc cgt gaa agc aaa gga ggg gaa atg ctg act gcg | 1453 |

```
            Thr  Ser  Ser  Gln  Leu  Arg  Glu  Ser  Lys  Gly  Glu  Met  Leu  Thr  Ala
                      450                      455                      460 ttg  gat  ttc  cac  atg  aaa  gaa  tat  ggt  ctg  acg  aag  gaa  gag  gcg  gca              1501
            Leu  Asp  Phe  His  Met  Lys  Glu  Tyr  Gly  Leu  Thr  Lys  Glu  Glu  Ala  Ala
                           465                      470                      475 tct  aag  ttt  gaa  gga  ttg  gtt  gag  gaa  aca  tgg  aag  gat  ata  aac  aag              1549
            Ser  Lys  Phe  Glu  Gly  Leu  Val  Glu  Glu  Thr  Trp  Lys  Asp  Ile  Asn  Lys
                      480                      485                      490 gaa  ttc  ata  gcc  aca  act  aat  tat  aat  gtg  ggt  aga  gaa  att  gcc  atc              1597
            Glu  Phe  Ile  Ala  Thr  Thr  Asn  Tyr  Asn  Val  Gly  Arg  Glu  Ile  Ala  Ile
                 495                      500                      505 aca  ttc  ctc  aac  tac  gct  cgg  ata  tgt  gaa  gcc  agt  tac  agc  aaa  act              1645
            Thr  Phe  Leu  Asn  Tyr  Ala  Arg  Ile  Cys  Glu  Ala  Ser  Tyr  Ser  Lys  Thr
            510                      515                      520                      525 gac  gga  gac  gct  tat  tca  gat  cct  aat  gtt  gcc  aag  gca  aat  gtc  gtt              1693
            Asp  Gly  Asp  Ala  Tyr  Ser  Asp  Pro  Asn  Val  Ala  Lys  Ala  Asn  Val  Val
                                530                      535                      540 gct  ctc  ttt  gtt  gat  gcc  ata  gtc  ttt  tgatttgcat  aatcaaagac                          1740
            Ala  Leu  Phe  Val  Asp  Ala  Ile  Val  Phe
                           545                      550 cctataatta  taattatatg  tgtttaagaa  actaataagc  ttgctttatg  tatagttgtc                       1800
aattgaataa  taatgtatta  attagtagag  ttaagaagtt  ataaagaata  aagaggagct                       1860
ggtagacgta  aacaagaaat  aatgtgtcaa  ataacttca   actttttcaa  gaataaagaa                       1920
ttggaagaga  ccaatatata  caaaaaaaaa  aaaaaaaa                                                 1959

<210> SEQ ID NO 2
            <211> LENGTH: 550
            <212> TYPE: PRT
            <213> ORGANISM: Mentha piperita

<400> SEQUENCE: 2

Met  Ala  Thr  Asn  Gly  Val  Val  Ile  Ser  Cys  Leu  Arg  Glu  Val  Arg  Pro
             1                  5                      10                      15

Pro  Met  Thr  Lys  His  Ala  Pro  Ser  Met  Trp  Thr  Asp  Thr  Phe  Ser  Asn
                           20                      25                      30

Phe  Ser  Leu  Asp  Asp  Lys  Glu  Gln  Gln  Lys  Cys  Ser  Glu  Thr  Ile  Glu
                      35                      40                      45

Ala  Leu  Lys  Gln  Glu  Ala  Arg  Gly  Met  Leu  Met  Ala  Ala  Thr  Thr  Pro
            50                       55                      60

Leu  Gln  Gln  Met  Thr  Leu  Ile  Asp  Thr  Leu  Glu  Arg  Leu  Gly  Leu  Ser
            65                       70                      75                      80

Phe  His  Phe  Glu  Thr  Glu  Ile  Glu  Tyr  Lys  Ile  Glu  Leu  Ile  Asn  Ala
                              85                      90                      95

Ala  Glu  Asp  Asp  Gly  Phe  Asp  Leu  Phe  Ala  Thr  Ala  Leu  Arg  Phe  Arg
                              100                     105                     110

Leu  Leu  Arg  Gln  His  Gln  Arg  His  Val  Ser  Cys  Asp  Val  Phe  Asp  Lys
                      115                     120                     125

Phe  Ile  Asp  Lys  Asp  Gly  Lys  Phe  Glu  Glu  Ser  Leu  Ser  Asn  Asn  Val
                      130                     135                     140

Glu  Gly  Leu  Leu  Ser  Leu  Tyr  Glu  Ala  Ala  His  Val  Gly  Phe  Arg  Glu
            145                     150                     155                     160

Glu  Arg  Ile  Leu  Gln  Glu  Ala  Val  Asn  Phe  Thr  Arg  His  His  Leu  Glu
                              165                     170                     175

Gly  Ala  Glu  Leu  Asp  Gln  Ser  Pro  Leu  Leu  Ile  Arg  Glu  Lys  Val  Lys
                      180                     185                     190

Arg  Ala  Leu  Glu  His  Pro  Leu  His  Arg  Asp  Phe  Pro  Ile  Val  Tyr  Ala
```

```
                    195                 200                 205
Arg Leu Phe Ile Ser Ile Tyr Glu Lys Asp Asp Ser Arg Asp Glu Leu
    210                 215                 220
Leu Leu Lys Leu Ser Lys Val Asn Phe Lys Phe Met Gln Asn Leu Tyr
225                 230                 235                 240
Lys Glu Glu Leu Ser Gln Leu Ser Arg Trp Trp Asn Thr Trp Asn Leu
                245                 250                 255
Lys Ser Lys Leu Pro Tyr Ala Arg Asp Arg Val Val Glu Ala Tyr Val
                260                 265                 270
Trp Gly Val Gly Tyr His Tyr Glu Pro Gln Tyr Ser Tyr Val Arg Met
            275                 280                 285
Gly Leu Ala Lys Gly Val Leu Ile Cys Gly Ile Met Asp Asp Thr Tyr
        290                 295                 300
Asp Asn Tyr Ala Thr Leu Asn Glu Ala Gln Leu Phe Thr Gln Val Leu
305                 310                 315                 320
Asp Lys Trp Asp Arg Asp Glu Ala Glu Arg Leu Pro Glu Tyr Met Lys
                325                 330                 335
Ile Val Tyr Arg Phe Ile Leu Ser Ile Tyr Glu Asn Tyr Glu Arg Asp
                340                 345                 350
Ala Ala Lys Leu Gly Lys Ser Phe Ala Ala Pro Tyr Phe Lys Glu Thr
            355                 360                 365
Val Lys Gln Leu Ala Arg Ala Phe Asn Glu Glu Gln Lys Trp Val Met
        370                 375                 380
Glu Arg Gln Leu Pro Ser Phe Gln Asp Tyr Val Lys Asn Ser Gly Lys
385                 390                 395                 400
Thr Ser Cys Ile Tyr Thr Met Phe Ala Ser Ile Ile Pro Gly Leu Lys
                405                 410                 415
Ser Val Thr Gln Glu Thr Ile Asp Trp Ile Lys Ser Glu Pro Thr Leu
                420                 425                 430
Ala Thr Ser Thr Ala Met Ile Gly Arg Tyr Trp Asn Asp Thr Ser Ser
            435                 440                 445
Gln Leu Arg Glu Ser Lys Gly Gly Glu Met Leu Thr Ala Leu Asp Phe
        450                 455                 460
His Met Lys Glu Tyr Gly Leu Thr Lys Glu Glu Ala Ala Ser Lys Phe
465                 470                 475                 480
Glu Gly Leu Val Glu Glu Thr Trp Lys Asp Ile Asn Lys Glu Phe Ile
                485                 490                 495
Ala Thr Thr Asn Tyr Asn Val Gly Arg Glu Ile Ala Ile Thr Phe Leu
                500                 505                 510
Asn Tyr Ala Arg Ile Cys Glu Ala Ser Tyr Ser Lys Thr Asp Gly Asp
            515                 520                 525
Ala Tyr Ser Asp Pro Asn Val Ala Lys Ala Asn Val Val Ala Leu Phe
        530                 535                 540
Val Asp Ala Ile Val Phe
545                 550

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: conserved
      amino acid motif
<220> FEATURE:
<221> NAME/KEY: DOMAIN
<222> LOCATION: (1)..(5)
<223> OTHER INFORMATION: Conserved domain that may coordinate binding of
``` divalent metal ion wherein Xaa represents any amino acid

<400> SEQUENCE: 3

Asp Asp Xaa Xaa Asp
 1               5

<210> SEQ ID NO 4
<211> LENGTH: 1650
<212> TYPE: DNA
<213> ORGANISM: Artificial Sequence
<220> FEATURE:
<223> OTHER INFORMATION: Description of Artificial Sequence: nucleic
      acid sequence encoding peppermint E-beta-farnesene
      synthase protein
<220> FEATURE:
<221> NAME/KEY: CDS
<222> LOCATION: (1)..(1650)
<223> OTHER INFORMATION: Computer-generated nucleic acid sequence
      encoding peppermint E-beta-farnesene synthase protein

<400> SEQUENCE: 4

| | | |
|---|---|---|
| atg gca aca aac ggc gtc gta att agt tgc tta agg gaa gta agg cca<br>Met Ala Thr Asn Gly Val Val Ile Ser Cys Leu Arg Glu Val Arg Pro<br> 1               5                  10                  15 | | 48 |
| cct atg acg aag cat gcg cca agc atg tgg act gat acc ttt tct aac<br>Pro Met Thr Lys His Ala Pro Ser Met Trp Thr Asp Thr Phe Ser Asn<br>              20                  25                  30 | | 96 |
| ttt tct ctt gac gat aag gaa caa caa aag tgc tca gaa acc atc gaa<br>Phe Ser Leu Asp Asp Lys Glu Gln Gln Lys Cys Ser Glu Thr Ile Glu<br>          35                  40                  45 | | 144 |
| gca ctt aag caa gaa gca aga ggc atg ctt atg gct gca acc act cct<br>Ala Leu Lys Gln Glu Ala Arg Gly Met Leu Met Ala Ala Thr Thr Pro<br>      50                  55                  60 | | 192 |
| ctc caa caa atg aca cta atc gac act ctc gag cgt ttg gga ttg tct<br>Leu Gln Gln Met Thr Leu Ile Asp Thr Leu Glu Arg Leu Gly Leu Ser<br>  65                  70                  75                  80 | | 240 |
| ttc cat ttt gag acg gag atc gaa tac aaa atc gaa cta atc aac gct<br>Phe His Phe Glu Thr Glu Ile Glu Tyr Lys Ile Glu Leu Ile Asn Ala<br>                  85                  90                  95 | | 288 |
| gca gaa gac gac ggc ttt gat ttg ttc gct act gct ctt cgt ttc cgt<br>Ala Glu Asp Asp Gly Phe Asp Leu Phe Ala Thr Ala Leu Arg Phe Arg<br>             100                 105                 110 | | 336 |
| ttg ctc aga caa cat caa cgc cac gtt tct tgt gat gtt ttc gac aag<br>Leu Leu Arg Gln His Gln Arg His Val Ser Cys Asp Val Phe Asp Lys<br>         115                 120                 125 | | 384 |
| ttc atc gac aaa gat ggc aag ttc gaa gaa tcc ctt agc aat aat gtt<br>Phe Ile Asp Lys Asp Gly Lys Phe Glu Glu Ser Leu Ser Asn Asn Val<br>     130                 135                 140 | | 432 |
| gaa ggc cta tta agc ttg tat gaa gca gct cat gtt ggg ttt cgc gaa<br>Glu Gly Leu Leu Ser Leu Tyr Glu Ala Ala His Val Gly Phe Arg Glu<br>145                 150                 155                 160 | | 480 |
| gaa aga ata tta caa gag gct gta aat ttt acg agg cat cac ttg gaa<br>Glu Arg Ile Leu Gln Glu Ala Val Asn Phe Thr Arg His His Leu Glu<br>                 165                 170                 175 | | 528 |
| gga gca gag tta gat cag tct cca tta ttg att aga gag aaa gtg aag<br>Gly Ala Glu Leu Asp Gln Ser Pro Leu Leu Ile Arg Glu Lys Val Lys<br>             180                 185                 190 | | 576 |
| cga gct ttg gag cac cct ctt cat agg gat ttc ccc att gtc tat gca<br>Arg Ala Leu Glu His Pro Leu His Arg Asp Phe Pro Ile Val Tyr Ala<br>         195                 200                 205 | | 624 |
| cgc ctt ttc atc tcc att tac gaa aag gat gac tct aga gat gaa tta<br>Arg Leu Phe Ile Ser Ile Tyr Glu Lys Asp Asp Ser Arg Asp Glu Leu<br>     210                 215                 220 | | 672 |

```
ctt ctc aag cta tcc aaa gtc aac ttc aaa ttc atg cag aat ttg tat        720
Leu Leu Lys Leu Ser Lys Val Asn Phe Lys Phe Met Gln Asn Leu Tyr
225                 230                 235                 240 aag gaa gag ctc tcc caa ctc tcc agg tgg tgg aac aca tgg aat ctg        768
Lys Glu Glu Leu Ser Gln Leu Ser Arg Trp Trp Asn Thr Trp Asn Leu
                245                 250                 255 aaa tca aaa tta cca tat gca aga gat cga gtc gtg gag gct tat gtt        816
Lys Ser Lys Leu Pro Tyr Ala Arg Asp Arg Val Val Glu Ala Tyr Val
            260                 265                 270 tgg gga gta ggt tac cat tac gaa ccc caa tac tca tat gtt cga atg        864
Trp Gly Val Gly Tyr His Tyr Glu Pro Gln Tyr Ser Tyr Val Arg Met
        275                 280                 285 gga ctt gcc aaa ggc gta cta att tgt gga atc atg gac gat aca tat        912
Gly Leu Ala Lys Gly Val Leu Ile Cys Gly Ile Met Asp Asp Thr Tyr
290                 295                 300 gat aat tat gct aca ctc aat gaa gct caa ctt ttt act caa gtc tta        960
Asp Asn Tyr Ala Thr Leu Asn Glu Ala Gln Leu Phe Thr Gln Val Leu
305                 310                 315                 320 gac aag tgg gat aga gat gaa gct gaa cga ctc cca gaa tac atg aaa       1008
Asp Lys Trp Asp Arg Asp Glu Ala Glu Arg Leu Pro Glu Tyr Met Lys
                325                 330                 335 atc gtt tat cga ttt att ttg agt ata tat gaa aat tat gaa cgt gat       1056
Ile Val Tyr Arg Phe Ile Leu Ser Ile Tyr Glu Asn Tyr Glu Arg Asp
            340                 345                 350 gca gcg aaa ctt gga aaa agc ttt gca gct cct tat ttt aag gaa acc       1104
Ala Ala Lys Leu Gly Lys Ser Phe Ala Ala Pro Tyr Phe Lys Glu Thr
        355                 360                 365 gtg aaa caa ctg gca agg gca ttt aat gag gag cag aag tgg gtt atg       1152
Val Lys Gln Leu Ala Arg Ala Phe Asn Glu Glu Gln Lys Trp Val Met
370                 375                 380 gaa agg cag cta ccg tca ttc caa gac tac gta aag aat tca gag aaa       1200
Glu Arg Gln Leu Pro Ser Phe Gln Asp Tyr Val Lys Asn Ser Glu Lys
385                 390                 395                 400 acc agc tgc att tat acc atg ttt gct tct atc atc cca ggc ttg aaa       1248
Thr Ser Cys Ile Tyr Thr Met Phe Ala Ser Ile Ile Pro Gly Leu Lys
                405                 410                 415 tct gtt acc caa gaa acc att gat tgg atc aag agt gaa ccc acg ctc       1296
Ser Val Thr Gln Glu Thr Ile Asp Trp Ile Lys Ser Glu Pro Thr Leu
            420                 425                 430 gca aca tcg acc gct atg atc ggt cgg tat tgg aat gac acc agc tct       1344
Ala Thr Ser Thr Ala Met Ile Gly Arg Tyr Trp Asn Asp Thr Ser Ser
        435                 440                 445 cag ctc cgt gaa agc aaa gga ggg gaa atg ctg act gcg ttg gat ttc       1392
Gln Leu Arg Glu Ser Lys Gly Gly Glu Met Leu Thr Ala Leu Asp Phe
450                 455                 460 cac atg aaa gaa tat ggt ctg acg aag gaa gag gcg gca tct aag ttt       1440
His Met Lys Glu Tyr Gly Leu Thr Lys Glu Glu Ala Ala Ser Lys Phe
465                 470                 475                 480 gaa gga ttg gtt gag gaa aca tgg aag gat ata aac aag gaa ttc ata       1488
Glu Gly Leu Val Glu Glu Thr Trp Lys Asp Ile Asn Lys Glu Phe Ile
                485                 490                 495 gcc aca act aat tat aat gtg ggt aga gaa att gcc atc aca ttc ctc       1536
Ala Thr Thr Asn Tyr Asn Val Gly Arg Glu Ile Ala Ile Thr Phe Leu
            500                 505                 510 aac tac gct cgg ata tgt gaa gcc agt tac agc aaa act gac gga gac       1584
Asn Tyr Ala Arg Ile Cys Glu Ala Ser Tyr Ser Lys Thr Asp Gly Asp
        515                 520                 525 gct tat tca gat cct aat gtt gcc aag gca aat gtc gtt gct ctc ttt       1632
Ala Tyr Ser Asp Pro Asn Val Ala Lys Ala Asn Val Val Ala Leu Phe
530                 535                 540
```

```
gtt gat gcc ata gtc ttt                                              1650
Val Asp Ala Ile Val Phe
545             550
```

<210> SEQ ID NO 5
<211> LENGTH: 550
<212> TYPE: PRT
<213> ORGANISM: Artificial Sequence

<400> SEQUENCE: 5

```
Met Ala Thr Asn Gly Val Val Ile Ser Cys Leu Arg Glu Val Arg Pro
 1               5                  10                  15

Pro Met Thr Lys His Ala Pro Ser Met Trp Thr Asp Thr Phe Ser Asn
            20                  25                  30

Phe Ser Leu Asp Asp Lys Glu Gln Gln Lys Cys Ser Glu Thr Ile Glu
        35                  40                  45

Ala Leu Lys Gln Glu Ala Arg Gly Met Leu Met Ala Ala Thr Thr Pro
    50                  55                  60

Leu Gln Gln Met Thr Leu Ile Asp Thr Leu Glu Arg Leu Gly Leu Ser
65                  70                  75                  80

Phe His Phe Glu Thr Glu Ile Glu Tyr Lys Ile Glu Leu Ile Asn Ala
                85                  90                  95

Ala Glu Asp Asp Gly Phe Asp Leu Phe Ala Thr Ala Leu Arg Phe Arg
            100                 105                 110

Leu Leu Arg Gln His Gln Arg His Val Ser Cys Asp Val Phe Asp Lys
        115                 120                 125

Phe Ile Asp Lys Asp Gly Lys Phe Glu Glu Ser Leu Ser Asn Asn Val
    130                 135                 140

Glu Gly Leu Leu Ser Leu Tyr Glu Ala Ala His Val Gly Phe Arg Glu
145                 150                 155                 160

Glu Arg Ile Leu Gln Glu Ala Val Asn Phe Thr Arg His His Leu Glu
                165                 170                 175

Gly Ala Glu Leu Asp Gln Ser Pro Leu Leu Ile Arg Glu Lys Val Lys
            180                 185                 190

Arg Ala Leu Glu His Pro Leu His Arg Asp Phe Pro Ile Val Tyr Ala
        195                 200                 205

Arg Leu Phe Ile Ser Ile Tyr Glu Lys Asp Asp Ser Arg Asp Glu Leu
    210                 215                 220

Leu Leu Lys Leu Ser Lys Val Asn Phe Lys Phe Met Gln Asn Leu Tyr
225                 230                 235                 240

Lys Glu Glu Leu Ser Gln Leu Ser Arg Trp Trp Asn Thr Trp Asn Leu
                245                 250                 255

Lys Ser Lys Leu Pro Tyr Ala Arg Asp Arg Val Val Glu Ala Tyr Val
            260                 265                 270

Trp Gly Val Gly Tyr His Tyr Glu Pro Gln Tyr Ser Tyr Val Arg Met
        275                 280                 285

Gly Leu Ala Lys Gly Val Leu Ile Cys Gly Ile Met Asp Asp Thr Tyr
    290                 295                 300

Asp Asn Tyr Ala Thr Leu Asn Glu Ala Gln Leu Phe Thr Gln Val Leu
305                 310                 315                 320

Asp Lys Trp Asp Arg Asp Glu Ala Glu Arg Leu Pro Glu Tyr Met Lys
                325                 330                 335

Ile Val Tyr Arg Phe Ile Leu Ser Ile Tyr Glu Asn Tyr Glu Arg Asp
            340                 345                 350

Ala Ala Lys Leu Gly Lys Ser Phe Ala Ala Pro Tyr Phe Lys Glu Thr
        355                 360                 365
```

```
Val Lys Gln Leu Ala Arg Ala Phe Asn Glu Glu Gln Lys Trp Val Met
    370                 375                 380
Glu Arg Gln Leu Pro Ser Phe Gln Asp Tyr Val Lys Asn Ser Glu Lys
385                 390                 395                 400
Thr Ser Cys Ile Tyr Thr Met Phe Ala Ser Ile Ile Pro Gly Leu Lys
                405                 410                 415
Ser Val Thr Gln Glu Thr Ile Asp Trp Ile Lys Ser Glu Pro Thr Leu
            420                 425                 430
Ala Thr Ser Thr Ala Met Ile Gly Arg Tyr Trp Asn Asp Thr Ser Ser
        435                 440                 445
Gln Leu Arg Glu Ser Lys Gly Gly Glu Met Leu Thr Ala Leu Asp Phe
    450                 455                 460
His Met Lys Glu Tyr Gly Leu Thr Lys Glu Glu Ala Ala Ser Lys Phe
465                 470                 475                 480
Glu Gly Leu Val Glu Glu Thr Trp Lys Asp Ile Asn Lys Glu Phe Ile
                485                 490                 495
Ala Thr Thr Asn Tyr Asn Val Gly Arg Glu Ile Ala Ile Thr Phe Leu
            500                 505                 510
Asn Tyr Ala Arg Ile Cys Glu Ala Ser Tyr Ser Lys Thr Asp Gly Asp
        515                 520                 525
Ala Tyr Ser Asp Pro Asn Val Ala Lys Ala Asn Val Val Ala Leu Phe
    530                 535                 540
Val Asp Ala Ile Val Phe
545                 550

<210> SEQ ID NO 6
<211> LENGTH: 1650
<212> TYPE: DNA
<213> ORGANISM: Artificial Sequence
<220> FEATURE:
<223> OTHER INFORMATION: Description of Artificial Sequence: nucleic
      acid sequence encoding E-beta-farnesene synthase
      protein
<220> FEATURE:
<221> NAME/KEY: CDS
<222> LOCATION: (1)..(1650)
<223> OTHER INFORMATION: Computer-generated nucleic acid sequence
      encoding peppermint E-beta-farnesene synthase protein

<400> SEQUENCE: 6 atg gct aca aac ggc gtc gtc att agt tgc tta agg gaa gta agg cca      48
Met Ala Thr Asn Gly Val Val Ile Ser Cys Leu Arg Glu Val Arg Pro
  1               5                  10                  15 cct atg tcg aag cat gcg cca agc atg tgg act gat acc ttt tct aac      96
Pro Met Ser Lys His Ala Pro Ser Met Trp Thr Asp Thr Phe Ser Asn
             20                  25                  30 ttt tct ctt gac gat aag gaa caa caa aag tgc tca gaa acc atc gaa     144
Phe Ser Leu Asp Asp Lys Glu Gln Gln Lys Cys Ser Glu Thr Ile Glu
         35                  40                  45 gca ctt aag caa gaa gca aga ggc atg ctt atg gct gca acc act cct     192
Ala Leu Lys Gln Glu Ala Arg Gly Met Leu Met Ala Ala Thr Thr Pro
     50                  55                  60 ctc caa caa atg aca cta atc gac act ctc gag cgt ttg gga ttg tct     240
Leu Gln Gln Met Thr Leu Ile Asp Thr Leu Glu Arg Leu Gly Leu Ser
 65                  70                  75                  80 ttc cat ttt gag acg gag atc gaa tac aaa atc gaa cta atc aac gct     288
Phe His Phe Glu Thr Glu Ile Glu Tyr Lys Ile Glu Leu Ile Asn Ala
                 85                  90                  95 gca gaa gac gac ggc ttt gat ttg ttc gct act gct ctt cgt ttc cgt     336
Ala Glu Asp Asp Gly Phe Asp Leu Phe Ala Thr Ala Leu Arg Phe Arg
            100                 105                 110
```

-continued

|  | 100 | | | | 105 | | | | | 110 | | | | | | |
|---|---|---|---|---|---|---|---|---|---|---|---|---|---|---|---|---|

```
ttg ctc aga caa cat caa cgc cac gtt tct tgt gat gtt ttc gac aag      384
Leu Leu Arg Gln His Gln Arg His Val Ser Cys Asp Val Phe Asp Lys
        115                 120                 125 ttc atc gac aaa gat ggc aag ttc gaa gaa tcc ctt agc aat aat gtt      432
Phe Ile Asp Lys Asp Gly Lys Phe Glu Glu Ser Leu Ser Asn Asn Val
130                 135                 140 gaa ggc cta tta agc ttg tat gaa gca gct cat gtt ggg ttt cgc gaa      480
Glu Gly Leu Leu Ser Leu Tyr Glu Ala Ala His Val Gly Phe Arg Glu
145                 150                 155                 160 gaa aga ata tta caa gag gct gta aat ttt acg agg cat cac ttg gaa      528
Glu Arg Ile Leu Gln Glu Ala Val Asn Phe Thr Arg His His Leu Glu
        165                 170                 175 gga gca gag tta gat cag tct cca tta ttg att aga gag aaa gtg aag      576
Gly Ala Glu Leu Asp Gln Ser Pro Leu Leu Ile Arg Glu Lys Val Lys
        180                 185                 190 cga gct ttg gag cac cct ctt cat agg gat ttc ccc att gtc tat gca      624
Arg Ala Leu Glu His Pro Leu His Arg Asp Phe Pro Ile Val Tyr Ala
        195                 200                 205 cgc ctt ttc atc tcc att tac gaa aag gat gac tct aga gat gaa tta      672
Arg Leu Phe Ile Ser Ile Tyr Glu Lys Asp Asp Ser Arg Asp Glu Leu
210                 215                 220 ctt ctc aag cta tcc aaa gtc aac ttc aaa ttc atg cag aat ttg tat      720
Leu Leu Lys Leu Ser Lys Val Asn Phe Lys Phe Met Gln Asn Leu Tyr
225                 230                 235                 240 aag gaa gag ctc tcc caa ctc tcc agg tgg tgg aac aca tgg aat ctg      768
Lys Glu Glu Leu Ser Gln Leu Ser Arg Trp Trp Asn Thr Trp Asn Leu
            245                 250                 255 aaa tca aaa tta cca tat gca aga gat cga gtc gtg gag gct tat gtt      816
Lys Ser Lys Leu Pro Tyr Ala Arg Asp Arg Val Val Glu Ala Tyr Val
        260                 265                 270 tgg gga gta ggt tac cat tac gaa ccc caa tac tca tat gtt cga atg      864
Trp Gly Val Gly Tyr His Tyr Glu Pro Gln Tyr Ser Tyr Val Arg Met
        275                 280                 285 gga ctt gcc aaa ggc gta cta att tgt gga atc atg gac gat aca tat      912
Gly Leu Ala Lys Gly Val Leu Ile Cys Gly Ile Met Asp Asp Thr Tyr
290                 295                 300 gat aat tat gct aca ctc aat gaa gct caa ctt ttt act caa gtc tta      960
Asp Asn Tyr Ala Thr Leu Asn Glu Ala Gln Leu Phe Thr Gln Val Leu
305                 310                 315                 320 gac aag tgg gat aga gat gaa gct gaa cga ctc cca gaa tac atg aaa     1008
Asp Lys Trp Asp Arg Asp Glu Ala Glu Arg Leu Pro Glu Tyr Met Lys
            325                 330                 335 atc gtt tat cga ttt att ttg agt ata tat gaa aat tat gaa cgt gat     1056
Ile Val Tyr Arg Phe Ile Leu Ser Ile Tyr Glu Asn Tyr Glu Arg Asp
        340                 345                 350 gca gcg aaa ctt gga aaa agc ttt gca gct cct tat ttt aag gaa acc     1104
Ala Ala Lys Leu Gly Lys Ser Phe Ala Ala Pro Tyr Phe Lys Glu Thr
        355                 360                 365 gtg aaa caa ctg gca agg gca ttt aat gag gag cag aag tgg gtt atg     1152
Val Lys Gln Leu Ala Arg Ala Phe Asn Glu Glu Gln Lys Trp Val Met
370                 375                 380 gaa agg cag cta ccg tca ttc caa gac tac gta aag aat tca gag aaa     1200
Glu Arg Gln Leu Pro Ser Phe Gln Asp Tyr Val Lys Asn Ser Glu Lys
385                 390                 395                 400 acc agc tgc att tat acc atg ttt gct tct atc atc cca ggc ttg aaa     1248
Thr Ser Cys Ile Tyr Thr Met Phe Ala Ser Ile Ile Pro Gly Leu Lys
            405                 410                 415 tct gtt acc caa gaa acc att gat tgg atc aag agt gaa ccc acg ctc     1296
Ser Val Thr Gln Glu Thr Ile Asp Trp Ile Lys Ser Glu Pro Thr Leu
```

-continued

```
              420                 425                 430
gca aca tcg acc gct atg atc ggt cgg tat tgg aat gac acc agc tct    1344
Ala Thr Ser Thr Ala Met Ile Gly Arg Tyr Trp Asn Asp Thr Ser Ser
            435                 440                 445 cag ctc cgt gaa agc aaa gga ggg gaa atg ctg act gcg ttg gat ttc    1392
Gln Leu Arg Glu Ser Lys Gly Gly Glu Met Leu Thr Ala Leu Asp Phe
        450                 455                 460 cac atg aaa gaa tat ggt ctg acg aag gaa gag gcg gca tct aag ttt    1440
His Met Lys Glu Tyr Gly Leu Thr Lys Glu Glu Ala Ala Ser Lys Phe
465                 470                 475                 480 gaa gga ttg gtt gag gaa aca tgg aag gat ata aac aag gaa ttc ata    1488
Glu Gly Leu Val Glu Glu Thr Trp Lys Asp Ile Asn Lys Glu Phe Ile
                485                 490                 495 gcc aca act aat tat aat gtg ggt aga gaa att gcc atc aca ttc ctc    1536
Ala Thr Thr Asn Tyr Asn Val Gly Arg Glu Ile Ala Ile Thr Phe Leu
            500                 505                 510 aac tac gct cgg ata tgt gaa gcc agt tac agc aaa act gac gga gac    1584
Asn Tyr Ala Arg Ile Cys Glu Ala Ser Tyr Ser Lys Thr Asp Gly Asp
        515                 520                 525 gct tat tca gat cct aat gtt gcc aag gca aat gtc gtt gct ctc ttt    1632
Ala Tyr Ser Asp Pro Asn Val Ala Lys Ala Asn Val Val Ala Leu Phe
530                 535                 540 gtt gat gcc ata gtc ttt                                            1650
Val Asp Ala Ile Val Phe
545                 550

<210> SEQ ID NO 7
<211> LENGTH: 550
<212> TYPE: PRT
<213> ORGANISM: Artificial Sequence

<400> SEQUENCE: 7

Met Ala Thr Asn Gly Val Val Ile Ser Cys Leu Arg Glu Val Arg Pro
1               5                   10                  15

Pro Met Ser Lys His Ala Pro Ser Met Trp Thr Asp Thr Phe Ser Asn
            20                  25                  30

Phe Ser Leu Asp Asp Lys Glu Gln Gln Lys Cys Ser Glu Thr Ile Glu
        35                  40                  45

Ala Leu Lys Gln Glu Ala Arg Gly Met Leu Met Ala Ala Thr Thr Pro
    50                  55                  60

Leu Gln Gln Met Thr Leu Ile Asp Thr Leu Glu Arg Leu Gly Leu Ser
65                  70                  75                  80

Phe His Phe Glu Thr Glu Ile Glu Tyr Lys Ile Glu Leu Ile Asn Ala
                85                  90                  95

Ala Glu Asp Asp Gly Phe Asp Leu Phe Ala Thr Ala Leu Arg Phe Arg
            100                 105                 110

Leu Leu Arg Gln His Gln Arg His Val Ser Cys Asp Val Phe Asp Lys
        115                 120                 125

Phe Ile Asp Lys Asp Gly Lys Phe Glu Glu Ser Leu Ser Asn Asn Val
    130                 135                 140

Glu Gly Leu Leu Ser Leu Tyr Glu Ala Ala His Val Gly Phe Arg Glu
145                 150                 155                 160

Glu Arg Ile Leu Gln Glu Ala Val Asn Phe Thr Arg His His Leu Glu
                165                 170                 175

Gly Ala Glu Leu Asp Gln Ser Pro Leu Leu Ile Arg Glu Lys Val Lys
            180                 185                 190

Arg Ala Leu Glu His Pro Leu His Arg Asp Phe Pro Ile Val Tyr Ala
        195                 200                 205
```

```
Arg Leu Phe Ile Ser Ile Tyr Glu Lys Asp Asp Ser Arg Asp Glu Leu
    210                 215                 220

Leu Leu Lys Leu Ser Lys Val Asn Phe Lys Phe Met Gln Asn Leu Tyr
225                 230                 235                 240

Lys Glu Glu Leu Ser Gln Leu Ser Arg Trp Trp Asn Thr Trp Asn Leu
                245                 250                 255

Lys Ser Lys Leu Pro Tyr Ala Arg Asp Arg Val Val Glu Ala Tyr Val
                260                 265                 270

Trp Gly Val Gly Tyr His Tyr Glu Pro Gln Tyr Ser Tyr Val Arg Met
                275                 280                 285

Gly Leu Ala Lys Gly Val Leu Ile Cys Gly Ile Met Asp Asp Thr Tyr
290                 295                 300

Asp Asn Tyr Ala Thr Leu Asn Glu Ala Gln Leu Phe Thr Gln Val Leu
305                 310                 315                 320

Asp Lys Trp Asp Arg Asp Glu Ala Glu Arg Leu Pro Glu Tyr Met Lys
                325                 330                 335

Ile Val Tyr Arg Phe Ile Leu Ser Ile Tyr Glu Asn Tyr Glu Arg Asp
                340                 345                 350

Ala Ala Lys Leu Gly Lys Ser Phe Ala Ala Pro Tyr Phe Lys Glu Thr
                355                 360                 365

Val Lys Gln Leu Ala Arg Ala Phe Asn Glu Glu Gln Lys Trp Val Met
370                 375                 380

Glu Arg Gln Leu Pro Ser Phe Gln Asp Tyr Val Lys Asn Ser Glu Lys
385                 390                 395                 400

Thr Ser Cys Ile Tyr Thr Met Phe Ala Ser Ile Ile Pro Gly Leu Lys
                405                 410                 415

Ser Val Thr Gln Glu Thr Ile Asp Trp Ile Lys Ser Glu Pro Thr Leu
                420                 425                 430

Ala Thr Ser Thr Ala Met Ile Gly Arg Tyr Trp Asn Asp Thr Ser Ser
                435                 440                 445

Gln Leu Arg Glu Ser Lys Gly Gly Glu Met Leu Thr Ala Leu Asp Phe
450                 455                 460

His Met Lys Glu Tyr Gly Leu Thr Lys Glu Glu Ala Ala Ser Lys Phe
465                 470                 475                 480

Glu Gly Leu Val Glu Glu Thr Trp Lys Asp Ile Asn Lys Glu Phe Ile
                485                 490                 495

Ala Thr Thr Asn Tyr Asn Val Gly Arg Glu Ile Ala Ile Thr Phe Leu
                500                 505                 510

Asn Tyr Ala Arg Ile Cys Glu Ala Ser Tyr Ser Lys Thr Asp Gly Asp
                515                 520                 525

Ala Tyr Ser Asp Pro Asn Val Ala Lys Ala Asn Val Val Ala Leu Phe
530                 535                 540

Val Asp Ala Ile Val Phe
545                 550

<210> SEQ ID NO 8
<211> LENGTH: 1650
<212> TYPE: DNA
<213> ORGANISM: Artificial Sequence
<220> FEATURE:
<223> OTHER INFORMATION: Description of Artificial Sequence: nucleic
      acid sequence encoding peppermint E-beta-farnesene
<220> FEATURE:
<221> NAME/KEY: CDS
<222> LOCATION: (1)..(1650)
<223> OTHER INFORMATION: Computer-generated nucleic acid sequence
      encoding peppermint E-beta-farnesene synthase protein
```

<400> SEQUENCE: 8

```
atg gct aca aac ggc gtc gta att agt tgc tta agg gaa gta agg cca      48
Met Ala Thr Asn Gly Val Val Ile Ser Cys Leu Arg Glu Val Arg Pro
  1               5                  10                  15 cct atg acg aag cat gcg cca agc atg tgg act gat acc ttt tct aac      96
Pro Met Thr Lys His Ala Pro Ser Met Trp Thr Asp Thr Phe Ser Asn
             20                  25                  30 ttt tct ctt gac gat aag gaa caa caa aag tgc tca gaa acc atc gaa     144
Phe Ser Leu Asp Asp Lys Glu Gln Gln Lys Cys Ser Glu Thr Ile Glu
         35                  40                  45 gca ctt aag caa gaa gca aga ggc atg ctt atg gct gca acc act cct     192
Ala Leu Lys Gln Glu Ala Arg Gly Met Leu Met Ala Ala Thr Thr Pro
     50                  55                  60 ctc caa caa atg aca cta atc gac act ctc gag cgt ttg gga ttg tct     240
Leu Gln Gln Met Thr Leu Ile Asp Thr Leu Glu Arg Leu Gly Leu Ser
 65                  70                  75                  80 ttc cat ttt gag acg gag atc gaa tac aaa atc gaa cta atc aac gct     288
Phe His Phe Glu Thr Glu Ile Glu Tyr Lys Ile Glu Leu Ile Asn Ala
                 85                  90                  95 gca gaa gac gac ggc ttt gat ttg ttc gct act gct ctt cgt ttc cgt     336
Ala Glu Asp Asp Gly Phe Asp Leu Phe Ala Thr Ala Leu Arg Phe Arg
            100                 105                 110 ttg ctc aga caa cat caa cgc cac gtt tct tgt gat gtt ttc gac aag     384
Leu Leu Arg Gln His Gln Arg His Val Ser Cys Asp Val Phe Asp Lys
        115                 120                 125 ttc atc gac aaa gat ggc aag ttc gaa gaa tcc ctt agc aat aat gtt     432
Phe Ile Asp Lys Asp Gly Lys Phe Glu Glu Ser Leu Ser Asn Asn Val
    130                 135                 140 gaa ggc cta tta agc ttg tat gaa gca gct cat gtt ggg ttt cgc gaa     480
Glu Gly Leu Leu Ser Leu Tyr Glu Ala Ala His Val Gly Phe Arg Glu
145                 150                 155                 160 gaa aga ata tta caa gag gct gta aat ttt acg agg cat cac ttg gaa     528
Glu Arg Ile Leu Gln Glu Ala Val Asn Phe Thr Arg His His Leu Glu
                165                 170                 175 gga gca gag tta gat cag tct cca tta ttg att aga gag aaa gtg aag     576
Gly Ala Glu Leu Asp Gln Ser Pro Leu Leu Ile Arg Glu Lys Val Lys
            180                 185                 190 cga gct ttg gag cac cct ctt cat agg gat ttc ccc att gtc tat gca     624
Arg Ala Leu Glu His Pro Leu His Arg Asp Phe Pro Ile Val Tyr Ala
        195                 200                 205 cgc ctt ttc atc tcc att tac gaa aag gat gac tct aga gat gaa tta     672
Arg Leu Phe Ile Ser Ile Tyr Glu Lys Asp Asp Ser Arg Asp Glu Leu
    210                 215                 220 ctt ctc aag cta tcc aaa gtc aac ttc aaa ttc atg cag aat ttg tat     720
Leu Leu Lys Leu Ser Lys Val Asn Phe Lys Phe Met Gln Asn Leu Tyr
225                 230                 235                 240 aag gaa gag ctc tcc caa ctc tcc agg tgg tgg aac aca tgg aat ctg     768
Lys Glu Glu Leu Ser Gln Leu Ser Arg Trp Trp Asn Thr Trp Asn Leu
                245                 250                 255 aaa tca aaa tta cca tat gca aga gat cga gtc gtg gag gct tat gtt     816
Lys Ser Lys Leu Pro Tyr Ala Arg Asp Arg Val Val Glu Ala Tyr Val
            260                 265                 270 tgg gga gta ggt tac cat tac gaa ccc caa tac tca tat gtt cga atg     864
Trp Gly Val Gly Tyr His Tyr Glu Pro Gln Tyr Ser Tyr Val Arg Met
        275                 280                 285 gga ctt gcc aaa ggc gta cta att tgt gga atc atg gac gat aca tat     912
Gly Leu Ala Lys Gly Val Leu Ile Cys Gly Ile Met Asp Asp Thr Tyr
    290                 295                 300 gat aat tat gct aca ctc aat gaa gct caa ctt ttt act caa gtc tta     960
Asp Asn Tyr Ala Thr Leu Asn Glu Ala Gln Leu Phe Thr Gln Val Leu
```

```
Asp Asn Tyr Ala Thr Leu Asn Glu Ala Gln Leu Phe Thr Gln Val Leu
305                 310                 315                 320 gac aag tgg gat aga gat gaa gct gaa cga ctc cca gaa tac atg aaa      1008
Asp Lys Trp Asp Arg Asp Glu Ala Glu Arg Leu Pro Glu Tyr Met Lys
                325                 330                 335 atc gtt tat cga ttt att ttg agt ata tat gaa aat tat gaa cgt gat      1056
Ile Val Tyr Arg Phe Ile Leu Ser Ile Tyr Glu Asn Tyr Glu Arg Asp
            340                 345                 350 gca gcg aaa ctt gga aaa agc ttt gca gct cct tat ttt aag gaa acc      1104
Ala Ala Lys Leu Gly Lys Ser Phe Ala Ala Pro Tyr Phe Lys Glu Thr
        355                 360                 365 gtg aaa caa ctg gca agg gca ttt aat gag gag cag aag tgg gtt atg      1152
Val Lys Gln Leu Ala Arg Ala Phe Asn Glu Glu Gln Lys Trp Val Met
    370                 375                 380 gaa agg cag cta ccg tca ttc caa gac tac gta aag aat tca gag aaa      1200
Glu Arg Gln Leu Pro Ser Phe Gln Asp Tyr Val Lys Asn Ser Glu Lys
385                 390                 395                 400 acc agc tgc att tat acc atg ttt gct tct atc atc cca ggc ttg aaa      1248
Thr Ser Cys Ile Tyr Thr Met Phe Ala Ser Ile Ile Pro Gly Leu Lys
                405                 410                 415 tct gtt acc caa gaa acc att gat tgg atc aag agt gaa ccc acg ctc      1296
Ser Val Thr Gln Glu Thr Ile Asp Trp Ile Lys Ser Glu Pro Thr Leu
            420                 425                 430 gca aca tcg acc gct atg atc ggt cgg tat tgg aat gac acc agc tct      1344
Ala Thr Ser Thr Ala Met Ile Gly Arg Tyr Trp Asn Asp Thr Ser Ser
        435                 440                 445 cag ctc cgt gaa agc aaa gga ggg gaa atg ctg act gcg ttg gat ttc      1392
Gln Leu Arg Glu Ser Lys Gly Gly Glu Met Leu Thr Ala Leu Asp Phe
    450                 455                 460 cac atg aaa gaa tat ggt ctg acg aag gaa gag gcg gca tct aag ttt      1440
His Met Lys Glu Tyr Gly Leu Thr Lys Glu Glu Ala Ala Ser Lys Phe
465                 470                 475                 480 gaa gga ttg gtt gag gaa aca tgg aag gat ata aac aag gaa ttc ata      1488
Glu Gly Leu Val Glu Glu Thr Trp Lys Asp Ile Asn Lys Glu Phe Ile
                485                 490                 495 gcc aca act caa tat aat gtg ggt aga gaa att gcc atc aca ttc ctc      1536
Ala Thr Thr Gln Tyr Asn Val Gly Arg Glu Ile Ala Ile Thr Phe Leu
            500                 505                 510 aac tac gct cgg ata tgt gaa gcc agt tac agc aaa act gac gga gac      1584
Asn Tyr Ala Arg Ile Cys Glu Ala Ser Tyr Ser Lys Thr Asp Gly Asp
        515                 520                 525 gct tat tca gat cct aat gtt gcc aag gca aat gtc gtt gct ctc ttt      1632
Ala Tyr Ser Asp Pro Asn Val Ala Lys Ala Asn Val Val Ala Leu Phe
    530                 535                 540 gtt gat gcc ata gtc ttt                                              1650
Val Asp Ala Ile Val Phe
545                 550

<210> SEQ ID NO 9
<211> LENGTH: 550
<212> TYPE: PRT
<213> ORGANISM: Artificial Sequence

<400> SEQUENCE: 9

Met Ala Thr Asn Gly Val Val Ile Ser Cys Leu Arg Glu Val Arg Pro
1               5                   10                  15

Pro Met Thr Lys His Ala Pro Ser Met Trp Thr Asp Thr Phe Ser Asn
            20                  25                  30

Phe Ser Leu Asp Asp Lys Glu Gln Lys Cys Ser Glu Thr Ile Glu
        35                  40                  45
```

-continued

```
Ala Leu Lys Gln Glu Ala Arg Gly Met Leu Met Ala Ala Thr Thr Pro
 50                  55                  60

Leu Gln Gln Met Thr Leu Ile Asp Thr Leu Glu Arg Leu Gly Leu Ser
 65                  70                  75                  80

Phe His Phe Glu Thr Glu Ile Glu Tyr Lys Ile Glu Leu Ile Asn Ala
                 85                  90                  95

Ala Glu Asp Asp Gly Phe Asp Leu Phe Ala Thr Ala Leu Arg Phe Arg
                100                 105                 110

Leu Leu Arg Gln His Gln Arg His Val Ser Cys Asp Val Phe Asp Lys
            115                 120                 125

Phe Ile Asp Lys Asp Gly Lys Phe Glu Glu Ser Leu Ser Asn Asn Val
130                 135                 140

Glu Gly Leu Leu Ser Leu Tyr Glu Ala Ala His Val Gly Phe Arg Glu
145                 150                 155                 160

Glu Arg Ile Leu Gln Glu Ala Val Asn Phe Thr Arg His His Leu Glu
                165                 170                 175

Gly Ala Glu Leu Asp Gln Ser Pro Leu Leu Ile Arg Glu Lys Val Lys
            180                 185                 190

Arg Ala Leu Glu His Pro Leu His Arg Asp Phe Pro Ile Val Tyr Ala
            195                 200                 205

Arg Leu Phe Ile Ser Ile Tyr Glu Lys Asp Asp Ser Arg Asp Glu Leu
210                 215                 220

Leu Leu Lys Leu Ser Lys Val Asn Phe Lys Phe Met Gln Asn Leu Tyr
225                 230                 235                 240

Lys Glu Glu Leu Ser Gln Leu Ser Arg Trp Trp Asn Thr Trp Asn Leu
                245                 250                 255

Lys Ser Lys Leu Pro Tyr Ala Arg Asp Arg Val Val Glu Ala Tyr Val
            260                 265                 270

Trp Gly Val Gly Tyr His Tyr Glu Pro Gln Tyr Ser Tyr Val Arg Met
            275                 280                 285

Gly Leu Ala Lys Gly Val Leu Ile Cys Gly Ile Met Asp Asp Thr Tyr
290                 295                 300

Asp Asn Tyr Ala Thr Leu Asn Glu Ala Gln Leu Phe Thr Gln Val Leu
305                 310                 315                 320

Asp Lys Trp Asp Arg Asp Glu Ala Glu Arg Leu Pro Glu Tyr Met Lys
                325                 330                 335

Ile Val Tyr Arg Phe Ile Leu Ser Ile Tyr Glu Asn Tyr Glu Arg Asp
            340                 345                 350

Ala Ala Lys Leu Gly Lys Ser Phe Ala Ala Pro Tyr Phe Lys Glu Thr
            355                 360                 365

Val Lys Gln Leu Ala Arg Ala Phe Asn Glu Glu Gln Lys Trp Val Met
370                 375                 380

Glu Arg Gln Leu Pro Ser Phe Gln Asp Tyr Val Lys Asn Ser Glu Lys
385                 390                 395                 400

Thr Ser Cys Ile Tyr Thr Met Phe Ala Ser Ile Ile Pro Gly Leu Lys
                405                 410                 415

Ser Val Thr Gln Glu Thr Ile Asp Trp Ile Lys Ser Glu Pro Thr Leu
            420                 425                 430

Ala Thr Ser Thr Ala Met Ile Gly Arg Tyr Trp Asn Asp Thr Ser Ser
            435                 440                 445

Gln Leu Arg Glu Ser Lys Gly Gly Glu Met Leu Thr Ala Leu Asp Phe
450                 455                 460

His Met Lys Glu Tyr Gly Leu Thr Lys Glu Glu Ala Ala Ser Lys Phe
465                 470                 475                 480
```

```
Glu Gly Leu Val Glu Thr Trp Lys Asp Ile Asn Lys Phe Ile
            485                 490                 495

Ala Thr Thr Gln Tyr Asn Val Gly Arg Glu Ile Ala Ile Thr Phe Leu
            500                 505                 510

Asn Tyr Ala Arg Ile Cys Glu Ala Ser Tyr Ser Lys Thr Asp Gly Asp
            515                 520                 525

Ala Tyr Ser Asp Pro Asn Val Ala Lys Ala Asn Val Val Ala Leu Phe
            530                 535                 540

Val Asp Ala Ile Val Phe
545             550

<210> SEQ ID NO 10
<211> LENGTH: 1650
<212> TYPE: DNA
<213> ORGANISM: Artificial Sequence
<220> FEATURE:
<223> OTHER INFORMATION: Description of Artificial Sequence: nucleic
      acid sequence encoding E-beta-farnesene synthase
      protein
<220> FEATURE:
<221> NAME/KEY: CDS
<222> LOCATION: (1)..(1650)
<223> OTHER INFORMATION: Computer-generated nucleic acid sequence
      encoding peppermint E-beta-farnesene synthase protein

<400> SEQUENCE: 10 atg gct aca aac ggc gtc gta att agt tgc tta agg gaa gta agg cca      48
Met Ala Thr Asn Gly Val Val Ile Ser Cys Leu Arg Glu Val Arg Pro
 1               5                  10                  15 cct atg acg aag cat gcg cca agc atg tgg act gat acc ttt tct aac      96
Pro Met Thr Lys His Ala Pro Ser Met Trp Thr Asp Thr Phe Ser Asn
             20                  25                  30 ttc tct ctt gac gat aag gaa caa caa aag tgc tca gaa acc atc gaa     144
Phe Ser Leu Asp Asp Lys Glu Gln Gln Lys Cys Ser Glu Thr Ile Glu
         35                  40                  45 gca ctt aag caa gaa gca aga ggc atg ctt atg gct gca acc act cct     192
Ala Leu Lys Gln Glu Ala Arg Gly Met Leu Met Ala Ala Thr Thr Pro
     50                  55                  60 ctc caa caa atg aca cta atc gac act ctc gag cgt ttg gga ttg tct     240
Leu Gln Gln Met Thr Leu Ile Asp Thr Leu Glu Arg Leu Gly Leu Ser
 65                  70                  75                  80 ttc cat ttt gag acg gag atc gaa tac aaa atc gaa cta atc aac gct     288
Phe His Phe Glu Thr Glu Ile Glu Tyr Lys Ile Glu Leu Ile Asn Ala
                 85                  90                  95 gca gaa gac gac ggc ttt gat ttg ttc gct act gct ctt cgt ttc cgt     336
Ala Glu Asp Asp Gly Phe Asp Leu Phe Ala Thr Ala Leu Arg Phe Arg
            100                 105                 110 ttg ctc aga caa cat caa cgc cac gtt tcg tgt gat gtt ttc gac aag     384
Leu Leu Arg Gln His Gln Arg His Val Ser Cys Asp Val Phe Asp Lys
        115                 120                 125 ttc atc gac aaa gat ggc aag ttc gaa gaa tcc ctt agc aat aat gtt     432
Phe Ile Asp Lys Asp Gly Lys Phe Glu Glu Ser Leu Ser Asn Asn Val
    130                 135                 140 gaa ggc cta tta agc ttg tat gaa gca gct cat gtt ggg ttt cgc gaa     480
Glu Gly Leu Leu Ser Leu Tyr Glu Ala Ala His Val Gly Phe Arg Glu
145                 150                 155                 160 gaa aga ata tta caa gag gct gta aat ttt acg agg cat cac ttg gaa     528
Glu Arg Ile Leu Gln Glu Ala Val Asn Phe Thr Arg His His Leu Glu
                165                 170                 175 gga gca gag tta gat cag tct cca tta ttg att aga gag aaa gtg aag     576
Gly Ala Glu Leu Asp Gln Ser Pro Leu Leu Ile Arg Glu Lys Val Lys
            180                 185                 190 cga gct ttg gag cac cct ctt cat agg gat ttc ccc att gtc tat gca     624
Arg Ala Leu Glu His Pro Leu His Arg Asp Phe Pro Ile Val Tyr Ala
        195                 200                 205
```

```
            195                 200                  205
cgc ctt ttc atc tcc att tac gaa aag gat gac tct aga gat gaa tta     672
Arg Leu Phe Ile Ser Ile Tyr Glu Lys Asp Asp Ser Arg Asp Glu Leu
    210                 215                  220 ctt ctc aag cta tcc aaa gtc aac ttc aaa ttc atg cag aat ttg tat     720
Leu Leu Lys Leu Ser Lys Val Asn Phe Lys Phe Met Gln Asn Leu Tyr
225                 230                  235                 240 aag gaa gag ctc tcc caa ctc tcc agg tgg tgg aac aca tgg aat ctg     768
Lys Glu Glu Leu Ser Gln Leu Ser Arg Trp Trp Asn Thr Trp Asn Leu
                245                 250                  255 aaa tca aaa tta cca tat gca aga gat cga gtc gtg gag gct tat gtt     816
Lys Ser Lys Leu Pro Tyr Ala Arg Asp Arg Val Val Glu Ala Tyr Val
            260                 265                  270 tgg gga gta ggt tac cat tac gaa ccc caa tac tca tat gtt cga atg     864
Trp Gly Val Gly Tyr His Tyr Glu Pro Gln Tyr Ser Tyr Val Arg Met
        275                 280                  285 gga ctt gcc aaa ggc gta cta att tgt gga atc atg gac gat aca tat     912
Gly Leu Ala Lys Gly Val Leu Ile Cys Gly Ile Met Asp Asp Thr Tyr
    290                 295                  300 gat aat tat gct aca ctc aat gaa gct caa ctt ttt act caa gtc tta     960
Asp Asn Tyr Ala Thr Leu Asn Glu Ala Gln Leu Phe Thr Gln Val Leu
305                 310                  315                 320 gac aag tgg gat aga gat gaa gct gaa cga ctc cca gaa tac atg aaa    1008
Asp Lys Trp Asp Arg Asp Glu Ala Glu Arg Leu Pro Glu Tyr Met Lys
                325                 330                  335 atc gtt tat cga ttt att ttg agt ata tat gaa aat tat gaa cgt gat    1056
Ile Val Tyr Arg Phe Ile Leu Ser Ile Tyr Glu Asn Tyr Glu Arg Asp
            340                 345                  350 gca gcg aaa ctt gga aaa agc ttt gca gct cct tat ttt aag gaa acc    1104
Ala Ala Lys Leu Gly Lys Ser Phe Ala Ala Pro Tyr Phe Lys Glu Thr
        355                 360                  365 gtg aaa caa ctg gca agg gca ttt aat gag gag cag aag tgg gtt atg    1152
Val Lys Gln Leu Ala Arg Ala Phe Asn Glu Glu Gln Lys Trp Val Met
    370                 375                  380 gaa agg cag cta ccg tca ttc caa gac tac gta aag aat tca gag aaa    1200
Glu Arg Gln Leu Pro Ser Phe Gln Asp Tyr Val Lys Asn Ser Glu Lys
385                 390                  395                 400 acc agc tgc att tat acc atg ttt gct tct atc atc cca ggc ttg aaa    1248
Thr Ser Cys Ile Tyr Thr Met Phe Ala Ser Ile Ile Pro Gly Leu Lys
                405                 410                  415 tct gtt acc caa gaa acc att gat tgg atc aag agt gaa ccc acg ctc    1296
Ser Val Thr Gln Glu Thr Ile Asp Trp Ile Lys Ser Glu Pro Thr Leu
            420                 425                  430 gca aca tcg acc gct atg atc ggt cgg tat tgg aat gac acc agc tct    1344
Ala Thr Ser Thr Ala Met Ile Gly Arg Tyr Trp Asn Asp Thr Ser Ser
        435                 440                  445 cag ctc cgt gaa agc aaa gga ggg gaa atg ctg act gcg ttg gat ttc    1392
Gln Leu Arg Glu Ser Lys Gly Gly Glu Met Leu Thr Ala Leu Asp Phe
    450                 455                  460 cac atg aaa gaa tat ggt ctg acg aag gaa gag gcg gca tct aag ttt    1440
His Met Lys Glu Tyr Gly Leu Thr Lys Glu Glu Ala Ala Ser Lys Phe
465                 470                  475                 480 gaa gga ttg gtt gag gaa aca tgg aag gat ata aac aag gaa ttc ata    1488
Glu Gly Leu Val Glu Glu Thr Trp Lys Asp Ile Asn Lys Glu Phe Ile
                485                 490                  495 gcc aca act aat tat aat gtg ggt aga gaa att gcc atc aca ttc ctc    1536
Ala Thr Thr Asn Tyr Asn Val Gly Arg Glu Ile Ala Ile Thr Phe Leu
            500                 505                  510 aac tac gct cgg ata tgt gaa gcc agt tac agc aaa act gac gga gac    1584
Asn Tyr Ala Arg Ile Cys Glu Ala Ser Tyr Ser Lys Thr Asp Gly Asp
```

```
                 515                 520                 525
gct tat tca gat cct aat gtt gcc aag gca aat gtc gtt gct ctc ttt     1632
Ala Tyr Ser Asp Pro Asn Val Ala Lys Ala Asn Val Val Ala Leu Phe
    530                 535                 540 gtt gat gcc ata gtc ttt                                             1650
Val Asp Ala Ile Val Phe
545             550

<210> SEQ ID NO 11
<211> LENGTH: 550
<212> TYPE: PRT
<213> ORGANISM: Artificial Sequence

<400> SEQUENCE: 11

Met Ala Thr Asn Gly Val Val Ile Ser Cys Leu Arg Glu Val Arg Pro
  1               5                  10                  15

Pro Met Thr Lys His Ala Pro Ser Met Trp Thr Asp Thr Phe Ser Asn
                 20                  25                  30

Phe Ser Leu Asp Asp Lys Glu Gln Gln Lys Cys Ser Glu Thr Ile Glu
             35                  40                  45

Ala Leu Lys Gln Glu Ala Arg Gly Met Leu Met Ala Thr Thr Pro
     50                  55                  60

Leu Gln Gln Met Thr Leu Ile Asp Thr Leu Glu Arg Leu Gly Leu Ser
 65                  70                  75                  80

Phe His Phe Glu Thr Glu Ile Glu Tyr Lys Ile Glu Leu Ile Asn Ala
                 85                  90                  95

Ala Glu Asp Asp Gly Phe Asp Leu Phe Ala Thr Ala Leu Arg Phe Arg
                100                 105                 110

Leu Leu Arg Gln His Gln Arg His Val Ser Cys Asp Val Phe Asp Lys
            115                 120                 125

Phe Ile Asp Lys Asp Gly Lys Phe Glu Glu Ser Leu Ser Asn Asn Val
        130                 135                 140

Glu Gly Leu Leu Ser Leu Tyr Glu Ala Ala His Val Gly Phe Arg Glu
145                 150                 155                 160

Glu Arg Ile Leu Gln Glu Ala Val Asn Phe Thr Arg His His Leu Glu
                165                 170                 175

Gly Ala Glu Leu Asp Gln Ser Pro Leu Leu Ile Arg Glu Lys Val Lys
            180                 185                 190

Arg Ala Leu Glu His Pro Leu His Arg Asp Phe Pro Ile Val Tyr Ala
        195                 200                 205

Arg Leu Phe Ile Ser Ile Tyr Glu Lys Asp Asp Ser Arg Asp Glu Leu
    210                 215                 220

Leu Leu Lys Leu Ser Lys Val Asn Phe Lys Phe Met Gln Asn Leu Tyr
225                 230                 235                 240

Lys Glu Glu Leu Ser Gln Leu Ser Arg Trp Trp Asn Thr Trp Asn Leu
                245                 250                 255

Lys Ser Lys Leu Pro Tyr Ala Arg Asp Arg Val Val Glu Ala Tyr Val
            260                 265                 270

Trp Gly Val Gly Tyr His Tyr Glu Pro Gln Tyr Ser Tyr Val Arg Met
        275                 280                 285

Gly Leu Ala Lys Gly Val Leu Ile Cys Gly Ile Met Asp Asp Thr Tyr
    290                 295                 300

Asp Asn Tyr Ala Thr Leu Asn Glu Ala Gln Leu Phe Thr Gln Val Leu
305                 310                 315                 320

Asp Lys Trp Asp Arg Asp Glu Ala Glu Arg Leu Pro Glu Tyr Met Lys
                325                 330                 335
```

```
Ile Val Tyr Arg Phe Ile Leu Ser Ile Tyr Glu Asn Tyr Glu Arg Asp
            340                 345                 350

Ala Ala Lys Leu Gly Lys Ser Phe Ala Ala Pro Tyr Phe Lys Glu Thr
        355                 360                 365

Val Lys Gln Leu Ala Arg Ala Phe Asn Glu Glu Gln Lys Trp Val Met
    370                 375                 380

Glu Arg Gln Leu Pro Ser Phe Gln Asp Tyr Val Lys Asn Ser Glu Lys
385                 390                 395                 400

Thr Ser Cys Ile Tyr Thr Met Phe Ala Ser Ile Ile Pro Gly Leu Lys
                405                 410                 415

Ser Val Thr Gln Glu Thr Ile Asp Trp Ile Lys Ser Glu Pro Thr Leu
            420                 425                 430

Ala Thr Ser Thr Ala Met Ile Gly Arg Tyr Trp Asn Asp Thr Ser Ser
        435                 440                 445

Gln Leu Arg Glu Ser Lys Gly Gly Glu Met Leu Thr Ala Leu Asp Phe
    450                 455                 460

His Met Lys Glu Tyr Gly Leu Thr Lys Glu Glu Ala Ala Ser Lys Phe
465                 470                 475                 480

Glu Gly Leu Val Glu Glu Thr Trp Lys Asp Ile Asn Lys Glu Phe Ile
                485                 490                 495

Ala Thr Thr Asn Tyr Asn Val Gly Arg Glu Ile Ala Ile Thr Phe Leu
            500                 505                 510

Asn Tyr Ala Arg Ile Cys Glu Ala Ser Tyr Ser Lys Thr Asp Gly Asp
        515                 520                 525

Ala Tyr Ser Asp Pro Asn Val Ala Lys Ala Asn Val Val Ala Leu Phe
    530                 535                 540

Val Asp Ala Ile Val Phe
545                 550
```

<210> SEQ ID NO 12
<211> LENGTH: 1650
<212> TYPE: DNA
<213> ORGANISM: Artificial Sequence
<220> FEATURE:
<223> OTHER INFORMATION: Description of Artificial Sequence: nucleic
      acid sequence encoding E-beta-farnesene synthase
<220> FEATURE:
<221> NAME/KEY: CDS
<222> LOCATION: (1)..(1650)
<223> OTHER INFORMATION: Computer-generated nucleic acid sequence
      encoding peppermint E-beta-farnesene synthase protein

<400> SEQUENCE: 12

```
atg gct ggg aac ggc gtc gta att agt tgc tta agg gaa gta agg cca      48
Met Ala Gly Asn Gly Val Val Ile Ser Cys Leu Arg Glu Val Arg Pro
  1               5                  10                  15 cct atg acg aag cat gcg cca agc atg tgg act gat acc ttt tct aac      96
Pro Met Thr Lys His Ala Pro Ser Met Trp Thr Asp Thr Phe Ser Asn
                 20                  25                  30 ttt tct ctt gac gat aag gaa caa caa aag tgc tca gaa acc atc gaa     144
Phe Ser Leu Asp Asp Lys Glu Gln Gln Lys Cys Ser Glu Thr Ile Glu
             35                  40                  45 gca ctt aag caa gaa gca aga ggc atg ctt atg gct gca acc act cct     192
Ala Leu Lys Gln Glu Ala Arg Gly Met Leu Met Ala Ala Thr Thr Pro
         50                  55                  60 ctc caa caa atg aca cta atc gac act ctc gag cgt ttg gga ttg tct     240
Leu Gln Gln Met Thr Leu Ile Asp Thr Leu Glu Arg Leu Gly Leu Ser
 65                  70                  75                  80 ttc cat ttt gag acg gag atc gaa tac aaa atc gaa cta atc aac gct     288
```

```
                Phe His Phe Glu Thr Glu Ile Glu Tyr Lys Ile Glu Leu Ile Asn Ala
                            85                  90                  95 gca gaa gac gac ggc ttt gat ttg ttc gct act gct ctt cgt ttc cgt           336
Ala Glu Asp Asp Gly Phe Asp Leu Phe Ala Thr Ala Leu Arg Phe Arg
            100                 105                 110 ttg ctc aga caa cat caa cgc cac gtt tct tgt gat gtt ttc gac aag           384
Leu Leu Arg Gln His Gln Arg His Val Ser Cys Asp Val Phe Asp Lys
            115                 120                 125 ttc atc gac aaa gat ggc aag ttc gaa gaa tcc ctt agc aat aat gtt           432
Phe Ile Asp Lys Asp Gly Lys Phe Glu Glu Ser Leu Ser Asn Asn Val
130                 135                 140 gaa ggc cta tta agc ttg tat gaa gca gct cat gtt ggg ttt cgc gaa           480
Glu Gly Leu Leu Ser Leu Tyr Glu Ala Ala His Val Gly Phe Arg Glu
145                 150                 155                 160 gaa aga ata tta caa gag gct gta aat ttt acg agg cat cac ttg gaa           528
Glu Arg Ile Leu Gln Glu Ala Val Asn Phe Thr Arg His His Leu Glu
                165                 170                 175 gga gca gag tta gat cag tct cca tta ttg att aga gag aaa gtg aag           576
Gly Ala Glu Leu Asp Gln Ser Pro Leu Leu Ile Arg Glu Lys Val Lys
            180                 185                 190 cga gct ttg gag cac cct ctt cat agg gat ttc ccc att gtc tat gca           624
Arg Ala Leu Glu His Pro Leu His Arg Asp Phe Pro Ile Val Tyr Ala
            195                 200                 205 cgc ctt ttc atc tcc att tac gaa aag gat gac tct aga gat gaa tta           672
Arg Leu Phe Ile Ser Ile Tyr Glu Lys Asp Asp Ser Arg Asp Glu Leu
210                 215                 220 ctt ctc aag cta tcc aaa gtc aac ttc aaa ttc atg cag aat ttg tat           720
Leu Leu Lys Leu Ser Lys Val Asn Phe Lys Phe Met Gln Asn Leu Tyr
225                 230                 235                 240 aag gaa gag ctc tcc caa ctc tcc agg tgg tgg aac aca tgg aat ctg           768
Lys Glu Glu Leu Ser Gln Leu Ser Arg Trp Trp Asn Thr Trp Asn Leu
                245                 250                 255 aaa tca aaa tta cca tat gca aga gat cga gtc gtg gag gct tat gtt           816
Lys Ser Lys Leu Pro Tyr Ala Arg Asp Arg Val Val Glu Ala Tyr Val
            260                 265                 270 tgg gga gta ggt tac cat tac gaa ccc caa tac tca tat gtt cga atg           864
Trp Gly Val Gly Tyr His Tyr Glu Pro Gln Tyr Ser Tyr Val Arg Met
            275                 280                 285 gga ctt gcc aaa ggc gta cta att tgt gga atc atg gac gat aca tat           912
Gly Leu Ala Lys Gly Val Leu Ile Cys Gly Ile Met Asp Asp Thr Tyr
            290                 295                 300 gat aat tat gct aca ctc aat gaa gct caa ctt ttt act caa gtc tta           960
Asp Asn Tyr Ala Thr Leu Asn Glu Ala Gln Leu Phe Thr Gln Val Leu
305                 310                 315                 320 gac aag tgg gat aga gat gaa gct gaa cga ctc cca gaa tac atg aaa          1008
Asp Lys Trp Asp Arg Asp Glu Ala Glu Arg Leu Pro Glu Tyr Met Lys
                325                 330                 335 atc gtt tat cga ttt att ttg agt ata tat gaa aat tat gaa cgt gat          1056
Ile Val Tyr Arg Phe Ile Leu Ser Ile Tyr Glu Asn Tyr Glu Arg Asp
            340                 345                 350 gca gcg aaa ctt gga aaa agc ttt gca gct cct tat ttt aag gaa acc          1104
Ala Ala Lys Leu Gly Lys Ser Phe Ala Ala Pro Tyr Phe Lys Glu Thr
            355                 360                 365 gtg aaa caa ctg gca agg gca ttt aat gag gag cag aag tgg gtt atg          1152
Val Lys Gln Leu Ala Arg Ala Phe Asn Glu Glu Gln Lys Trp Val Met
370                 375                 380 gaa agg cag cta ccg tca ttc caa gac tac gta aag aat tca gag aaa          1200
Glu Arg Gln Leu Pro Ser Phe Gln Asp Tyr Val Lys Asn Ser Glu Lys
385                 390                 395                 400 acc agc tgc att tat acc atg ttt gct tct atc atc cca ggc ttg aaa          1248
Thr Ser Cys Ile Tyr Thr Met Phe Ala Ser Ile Ile Pro Gly Leu Lys
```

```
Thr Ser Cys Ile Tyr Thr Met Phe Ala Ser Ile Ile Pro Gly Leu Lys
            405                 410                 415 tct gtt acc caa gaa acc att gat tgg atc aag agt gaa ccc acg ctc      1296
Ser Val Thr Gln Glu Thr Ile Asp Trp Ile Lys Ser Glu Pro Thr Leu
            420                 425                 430 gca aca tcg acc gct atg atc ggt cgg tat tgg aat gac acc agc tct      1344
Ala Thr Ser Thr Ala Met Ile Gly Arg Tyr Trp Asn Asp Thr Ser Ser
        435                 440                 445 cag ctc cgt gaa agc aaa gga ggg gaa atg ctg act gcg ttg gat ttc      1392
Gln Leu Arg Glu Ser Lys Gly Gly Glu Met Leu Thr Ala Leu Asp Phe
    450                 455                 460 cac atg aaa gaa tat ggt ctg acg aag gaa gag gcg gca tct aag ttt      1440
His Met Lys Glu Tyr Gly Leu Thr Lys Glu Glu Ala Ala Ser Lys Phe
465                 470                 475                 480 gaa gga ttg gtt gag gaa aca tgg aag gat ata aac aag gaa ttc ata      1488
Glu Gly Leu Val Glu Glu Thr Trp Lys Asp Ile Asn Lys Glu Phe Ile
                485                 490                 495 gcc aca act aat tat aat gtg ggt aga gaa att gcc atc aca ttc ctc      1536
Ala Thr Thr Asn Tyr Asn Val Gly Arg Glu Ile Ala Ile Thr Phe Leu
            500                 505                 510 aac tac gct cgg ata tgt gaa gcc agt tac agc aaa act gac gga gac      1584
Asn Tyr Ala Arg Ile Cys Glu Ala Ser Tyr Ser Lys Thr Asp Gly Asp
        515                 520                 525 gct tat tca gat cct aat gtt gcc aag gca aat gtc gtt gct ctc ttt      1632
Ala Tyr Ser Asp Pro Asn Val Ala Lys Ala Asn Val Val Ala Leu Phe
    530                 535                 540 gtt gat gcc ata gtc ttt                                              1650
Val Asp Ala Ile Val Phe
545                 550

<210> SEQ ID NO 13
<211> LENGTH: 550
<212> TYPE: PRT
<213> ORGANISM: Artificial Sequence

<400> SEQUENCE: 13

Met Ala Gly Asn Gly Val Val Ile Ser Cys Leu Arg Glu Val Arg Pro
  1               5                  10                  15

Pro Met Thr Lys His Ala Pro Ser Met Trp Thr Asp Thr Phe Ser Asn
                 20                  25                  30

Phe Ser Leu Asp Asp Lys Glu Gln Gln Lys Cys Ser Glu Thr Ile Glu
             35                  40                  45

Ala Leu Lys Gln Glu Ala Arg Gly Met Leu Met Ala Ala Thr Thr Pro
         50                  55                  60

Leu Gln Gln Met Thr Leu Ile Asp Thr Leu Glu Arg Leu Gly Leu Ser
 65                  70                  75                  80

Phe His Phe Glu Thr Glu Ile Glu Tyr Lys Ile Glu Leu Ile Asn Ala
                 85                  90                  95

Ala Glu Asp Asp Gly Phe Asp Leu Phe Ala Thr Ala Leu Arg Phe Arg
            100                 105                 110

Leu Leu Arg Gln His Gln Arg His Val Ser Cys Asp Val Phe Asp Lys
        115                 120                 125

Phe Ile Asp Lys Asp Gly Lys Phe Glu Glu Ser Leu Ser Asn Asn Val
    130                 135                 140

Glu Gly Leu Leu Ser Leu Tyr Glu Ala Ala His Val Gly Phe Arg Glu
145                 150                 155                 160

Glu Arg Ile Leu Gln Glu Ala Val Asn Phe Thr Arg His His Leu Glu
                165                 170                 175
```

Gly Ala Glu Leu Asp Gln Ser Pro Leu Leu Ile Arg Glu Lys Val Lys
            180                 185                 190

Arg Ala Leu Glu His Pro Leu His Arg Asp Phe Pro Ile Val Tyr Ala
        195                 200                 205

Arg Leu Phe Ile Ser Ile Tyr Glu Lys Asp Asp Ser Arg Asp Glu Leu
    210                 215                 220

Leu Leu Lys Leu Ser Lys Val Asn Phe Lys Phe Met Gln Asn Leu Tyr
225                 230                 235                 240

Lys Glu Glu Leu Ser Gln Leu Ser Arg Trp Trp Asn Thr Trp Asn Leu
                245                 250                 255

Lys Ser Lys Leu Pro Tyr Ala Arg Asp Arg Val Val Glu Ala Tyr Val
            260                 265                 270

Trp Gly Val Gly Tyr His Tyr Glu Pro Gln Tyr Ser Tyr Val Arg Met
        275                 280                 285

Gly Leu Ala Lys Gly Val Leu Ile Cys Gly Ile Met Asp Asp Thr Tyr
    290                 295                 300

Asp Asn Tyr Ala Thr Leu Asn Glu Ala Gln Leu Phe Thr Gln Val Leu
305                 310                 315                 320

Asp Lys Trp Asp Arg Asp Glu Ala Glu Arg Leu Pro Glu Tyr Met Lys
                325                 330                 335

Ile Val Tyr Arg Phe Ile Leu Ser Ile Tyr Glu Asn Tyr Glu Arg Asp
            340                 345                 350

Ala Ala Lys Leu Gly Lys Ser Phe Ala Ala Pro Tyr Phe Lys Glu Thr
        355                 360                 365

Val Lys Gln Leu Ala Arg Ala Phe Asn Glu Glu Gln Lys Trp Val Met
    370                 375                 380

Glu Arg Gln Leu Pro Ser Phe Gln Asp Tyr Val Lys Asn Ser Glu Lys
385                 390                 395                 400

Thr Ser Cys Ile Tyr Thr Met Phe Ala Ser Ile Ile Pro Gly Leu Lys
                405                 410                 415

Ser Val Thr Gln Glu Thr Ile Asp Trp Ile Lys Ser Glu Pro Thr Leu
            420                 425                 430

Ala Thr Ser Thr Ala Met Ile Gly Arg Tyr Trp Asn Asp Thr Ser Ser
        435                 440                 445

Gln Leu Arg Glu Ser Lys Gly Gly Glu Met Leu Thr Ala Leu Asp Phe
450                 455                 460

His Met Lys Glu Tyr Gly Leu Thr Lys Glu Glu Ala Ala Ser Lys Phe
465                 470                 475                 480

Glu Gly Leu Val Glu Glu Thr Trp Lys Asp Ile Asn Lys Glu Phe Ile
                485                 490                 495

Ala Thr Thr Asn Tyr Asn Val Gly Arg Glu Ile Ala Ile Thr Phe Leu
            500                 505                 510

Asn Tyr Ala Arg Ile Cys Glu Ala Ser Tyr Ser Lys Thr Asp Gly Asp
        515                 520                 525

Ala Tyr Ser Asp Pro Asn Val Ala Lys Ala Asn Val Val Ala Leu Phe
    530                 535                 540

Val Asp Ala Ile Val Phe
545                 550

<210> SEQ ID NO 14
<211> LENGTH: 1650
<212> TYPE: DNA
<213> ORGANISM: Artificial Sequence
<220> FEATURE:
<223> OTHER INFORMATION: Description of Artificial Sequence: nucleic
      acid sequence encoding E-beta-farnesene synthase

```
        protein
<220> FEATURE:
<221> NAME/KEY: CDS
<222> LOCATION: (1)..(1650)
<223> OTHER INFORMATION: Computer-generated nucleic acid sequence
      encoding peppermint E-beta-farnesene synthase protein

<400> SEQUENCE: 14 atg gct aca aac ggc gtc gta att agt tgc tta agg gaa gta agg cca        48
Met Ala Thr Asn Gly Val Val Ile Ser Cys Leu Arg Glu Val Arg Pro
 1               5                  10                  15 cct atg acg aag cat gcg cca agc atg tgg act gat acc ttt tct aac        96
Pro Met Thr Lys His Ala Pro Ser Met Trp Thr Asp Thr Phe Ser Asn
            20                  25                  30 ttt tct ctt gac gat aag gaa caa caa aag tgc tca gaa acc atc gaa       144
Phe Ser Leu Asp Asp Lys Glu Gln Gln Lys Cys Ser Glu Thr Ile Glu
        35                  40                  45 gca ctt aag caa gaa gca aga ggc atg ctt atg gct gca acc act cct       192
Ala Leu Lys Gln Glu Ala Arg Gly Met Leu Met Ala Ala Thr Thr Pro
    50                  55                  60 ctc caa caa atg aca cta atc gac act ctc gag cgt ttg gga ttg tct       240
Leu Gln Gln Met Thr Leu Ile Asp Thr Leu Glu Arg Leu Gly Leu Ser
65                  70                  75                  80 ttc cat ttt gag acg gag atc gaa tac aaa atc gaa cta atc aac gct       288
Phe His Phe Glu Thr Glu Ile Glu Tyr Lys Ile Glu Leu Ile Asn Ala
                85                  90                  95 gca gaa gac gac ggc ttt gat ttg ttc gct act gct ctt cgt ttc cgt       336
Ala Glu Asp Asp Gly Phe Asp Leu Phe Ala Thr Ala Leu Arg Phe Arg
           100                 105                 110 ttg ctc aga caa cat caa cgc cac gtt tct tgt gat gtt ttc gac aag       384
Leu Leu Arg Gln His Gln Arg His Val Ser Cys Asp Val Phe Asp Lys
       115                 120                 125 ttc atc gac aaa gat ggc aag ttc gaa gaa tcc ctt agc aat aat gtt       432
Phe Ile Asp Lys Asp Gly Lys Phe Glu Glu Ser Leu Ser Asn Asn Val
130                 135                 140 gaa ggc cta tta agc ttg tat gaa gca gct cat gtt ggg ttt cgc gaa       480
Glu Gly Leu Leu Ser Leu Tyr Glu Ala Ala His Val Gly Phe Arg Glu
145                 150                 155                 160 gaa aga ata tta caa gag gct gta aat ttt acg agg cat cac ttg gaa       528
Glu Arg Ile Leu Gln Glu Ala Val Asn Phe Thr Arg His His Leu Glu
                165                 170                 175 gga gca gag tta gat cag tct cca tta ttg att aga gag aaa gtg aag       576
Gly Ala Glu Leu Asp Gln Ser Pro Leu Leu Ile Arg Glu Lys Val Lys
            180                 185                 190 cga gct ttg gag cac cct ctt cat agg gat ttc ccc att gtc tat gca       624
Arg Ala Leu Glu His Pro Leu His Arg Asp Phe Pro Ile Val Tyr Ala
        195                 200                 205 cgc ctt ttc atc tcc att tac gaa aag gat gac tct aga gat gaa tta       672
Arg Leu Phe Ile Ser Ile Tyr Glu Lys Asp Asp Ser Arg Asp Glu Leu
    210                 215                 220 ctt ctc aag cta tcc aaa gtc aac ttc aaa ttc atg cag aat ttg tat       720
Leu Leu Lys Leu Ser Lys Val Asn Phe Lys Phe Met Gln Asn Leu Tyr
225                 230                 235                 240 aag gaa gag ctc tcc caa ctc tcc agg tgg tgg aac aca tgg aat ctg       768
Lys Glu Glu Leu Ser Gln Leu Ser Arg Trp Trp Asn Thr Trp Asn Leu
                245                 250                 255 aaa tca aaa tta ccc tat gca aga gat cga gtc gtg gag gct tat gtt       816
Lys Ser Lys Leu Pro Tyr Ala Arg Asp Arg Val Val Glu Ala Tyr Val
            260                 265                 270 tgg gga gta ggt tac cat tac gaa ccc caa tac tca tat gtt cga atg       864
Trp Gly Val Gly Tyr His Tyr Glu Pro Gln Tyr Ser Tyr Val Arg Met
        275                 280                 285
```

-continued

```
gga ctt gcc aaa ggc gta cta att tgt gga atc atg gac gat aca tat      912
Gly Leu Ala Lys Gly Val Leu Ile Cys Gly Ile Met Asp Asp Thr Tyr
        290                 295                 300 gat aat tat gct aca ctc aat gaa gct caa ctt ttt act caa gtc tta      960
Asp Asn Tyr Ala Thr Leu Asn Glu Ala Gln Leu Phe Thr Gln Val Leu
305                 310                 315                 320 gac aag tgg gat aga gat gaa gct gaa cga ctc cca gaa tac atg aaa     1008
Asp Lys Trp Asp Arg Asp Glu Ala Glu Arg Leu Pro Glu Tyr Met Lys
                325                 330                 335 atc gtt tat cga ttt att ttg agt ata tat gaa aat tat gaa cgt gat     1056
Ile Val Tyr Arg Phe Ile Leu Ser Ile Tyr Glu Asn Tyr Glu Arg Asp
            340                 345                 350 gca gcg aaa ctt gga aaa agc ttt gca gct cct tat ttt aag gaa acc     1104
Ala Ala Lys Leu Gly Lys Ser Phe Ala Ala Pro Tyr Phe Lys Glu Thr
        355                 360                 365 gtg aaa caa ctg gca agg gca ttt aat gag gag cag aag tgg gtt atg     1152
Val Lys Gln Leu Ala Arg Ala Phe Asn Glu Glu Gln Lys Trp Val Met
370                 375                 380 gaa agg cag cta ccg tca ttc caa gac tac gta aag aat tca gag aaa     1200
Glu Arg Gln Leu Pro Ser Phe Gln Asp Tyr Val Lys Asn Ser Glu Lys
385                 390                 395                 400 acc agc tgc att tat acc atg ttt gct tct atc atc cca ggc ttg aaa     1248
Thr Ser Cys Ile Tyr Thr Met Phe Ala Ser Ile Ile Pro Gly Leu Lys
                405                 410                 415 tct gtt acc caa gaa acc att gat tgg atc aag agt gaa ccc acg ctc     1296
Ser Val Thr Gln Glu Thr Ile Asp Trp Ile Lys Ser Glu Pro Thr Leu
            420                 425                 430 gca aca tcg acc gct atg atc ggt cgg tat tgg aat gac acc agc tct     1344
Ala Thr Ser Thr Ala Met Ile Gly Arg Tyr Trp Asn Asp Thr Ser Ser
        435                 440                 445 cag ctc cgt gaa agc aaa gga ggg gaa atg ctg act gcg ttg gat ttc     1392
Gln Leu Arg Glu Ser Lys Gly Gly Glu Met Leu Thr Ala Leu Asp Phe
450                 455                 460 cac atg aaa gaa tat ggt ctg acg aag gaa gag gcg gca tct aag ttt     1440
His Met Lys Glu Tyr Gly Leu Thr Lys Glu Glu Ala Ala Ser Lys Phe
465                 470                 475                 480 gaa gga ttg gtt gag gaa aca tgg aag gat ata aac aag gaa ttc ata     1488
Glu Gly Leu Val Glu Glu Thr Trp Lys Asp Ile Asn Lys Glu Phe Ile
                485                 490                 495 gcc aca act aat tat aat gtg ggt aga gaa att gcc atc aca ttc ctc     1536
Ala Thr Thr Asn Tyr Asn Val Gly Arg Glu Ile Ala Ile Thr Phe Leu
            500                 505                 510 aac tac gct cgg ata tgt gaa gcc agt tac agc aaa act gac gga gac     1584
Asn Tyr Ala Arg Ile Cys Glu Ala Ser Tyr Ser Lys Thr Asp Gly Asp
        515                 520                 525 gct tat tca gat cct aat gtt gcc aag gca aat gtc gtt gct ctc ttt     1632
Ala Tyr Ser Asp Pro Asn Val Ala Lys Ala Asn Val Val Ala Leu Phe
530                 535                 540 gtt gat gcc ata gtc ttt                                              1650
Val Asp Ala Ile Val Phe
545                 550

<210> SEQ ID NO 15
<211> LENGTH: 550
<212> TYPE: PRT
<213> ORGANISM: Artificial Sequence

<400> SEQUENCE: 15

Met Ala Thr Asn Gly Val Val Ile Ser Cys Leu Arg Glu Val Arg Pro
 1               5                  10                  15
```

-continued

```
Pro Met Thr Lys His Ala Pro Ser Met Trp Thr Asp Thr Phe Ser Asn
         20                  25                  30

Phe Ser Leu Asp Asp Lys Glu Gln Gln Lys Cys Ser Glu Thr Ile Glu
         35                  40                  45

Ala Leu Lys Gln Glu Ala Arg Gly Met Leu Met Ala Ala Thr Thr Pro
 50                      55                  60

Leu Gln Gln Met Thr Leu Ile Asp Thr Leu Glu Arg Leu Gly Leu Ser
 65                      70                  75                  80

Phe His Phe Glu Thr Glu Ile Glu Tyr Lys Ile Glu Leu Ile Asn Ala
                 85                  90                      95

Ala Glu Asp Asp Gly Phe Asp Leu Phe Ala Thr Ala Leu Arg Phe Arg
                100                 105                 110

Leu Leu Arg Gln His Gln Arg His Val Ser Cys Asp Val Phe Asp Lys
                115                 120                 125

Phe Ile Asp Lys Asp Gly Lys Phe Glu Glu Ser Leu Ser Asn Asn Val
130                 135                 140

Glu Gly Leu Leu Ser Leu Tyr Glu Ala Ala His Val Gly Phe Arg Glu
145                 150                 155                 160

Glu Arg Ile Leu Gln Glu Ala Val Asn Phe Thr Arg His His Leu Glu
                165                 170                 175

Gly Ala Glu Leu Asp Gln Ser Pro Leu Leu Ile Arg Glu Lys Val Lys
                180                 185                 190

Arg Ala Leu Glu His Pro Leu His Arg Asp Phe Pro Ile Val Tyr Ala
                195                 200                 205

Arg Leu Phe Ile Ser Ile Tyr Glu Lys Asp Asp Ser Arg Asp Glu Leu
210                 215                 220

Leu Leu Lys Leu Ser Lys Val Asn Phe Lys Phe Met Gln Asn Leu Tyr
225                 230                 235                 240

Lys Glu Glu Leu Ser Gln Leu Ser Arg Trp Trp Asn Thr Trp Asn Leu
                245                 250                 255

Lys Ser Lys Leu Pro Tyr Ala Arg Asp Arg Val Val Glu Ala Tyr Val
                260                 265                 270

Trp Gly Val Gly Tyr His Tyr Glu Pro Gln Tyr Ser Tyr Val Arg Met
                275                 280                 285

Gly Leu Ala Lys Gly Val Leu Ile Cys Gly Ile Met Asp Asp Thr Tyr
290                 295                 300

Asp Asn Tyr Ala Thr Leu Asn Glu Ala Gln Leu Phe Thr Gln Val Leu
305                 310                 315                 320

Asp Lys Trp Asp Arg Asp Glu Ala Glu Arg Leu Pro Glu Tyr Met Lys
                325                 330                 335

Ile Val Tyr Arg Phe Ile Leu Ser Ile Tyr Glu Asn Tyr Glu Arg Asp
                340                 345                 350

Ala Ala Lys Leu Gly Lys Ser Phe Ala Ala Pro Tyr Phe Lys Glu Thr
                355                 360                 365

Val Lys Gln Leu Ala Arg Ala Phe Asn Glu Glu Gln Lys Trp Val Met
 370                     375                 380

Glu Arg Gln Leu Pro Ser Phe Gln Asp Tyr Val Lys Asn Ser Glu Lys
385                 390                 395                 400

Thr Ser Cys Ile Tyr Thr Met Phe Ala Ser Ile Pro Gly Leu Lys
                405                 410                 415

Ser Val Thr Gln Glu Thr Ile Asp Trp Ile Lys Ser Glu Pro Thr Leu
                420                 425                 430

Ala Thr Ser Thr Ala Met Ile Gly Arg Tyr Trp Asn Asp Thr Ser Ser
                435                 440                 445
```

```
Gln Leu Arg Glu Ser Lys Gly Gly Glu Met Leu Thr Ala Leu Asp Phe
    450                 455                 460

His Met Lys Glu Tyr Gly Leu Thr Lys Glu Glu Ala Ala Ser Lys Phe
465                 470                 475                 480

Glu Gly Leu Val Glu Glu Thr Trp Lys Asp Ile Asn Lys Glu Phe Ile
                485                 490                 495

Ala Thr Thr Asn Tyr Asn Val Gly Arg Glu Ile Ala Ile Thr Phe Leu
            500                 505                 510

Asn Tyr Ala Arg Ile Cys Glu Ala Ser Tyr Ser Lys Thr Asp Gly Asp
        515                 520                 525

Ala Tyr Ser Asp Pro Asn Val Ala Lys Ala Asn Val Ala Leu Phe
    530                 535                 540

Val Asp Ala Ile Val Phe
545             550

<210> SEQ ID NO 16
<211> LENGTH: 1650
<212> TYPE: DNA
<213> ORGANISM: Artificial Sequence
<220> FEATURE:
<223> OTHER INFORMATION: Description of Artificial Sequence: nucleic
      acid sequence encoding E-beta-farnesene synthase
<220> FEATURE:
<221> NAME/KEY: CDS
<222> LOCATION: (1)..(1650)
<223> OTHER INFORMATION: Computer-generated nucleic acid sequence
      encoding peppermint E-beta-farnesene synthase protein

<400> SEQUENCE: 16 atg gct aca aac ggc gtc gta att agt tgc tta agg gaa gta agg cca      48
Met Ala Thr Asn Gly Val Val Ile Ser Cys Leu Arg Glu Val Arg Pro
1               5                   10                  15 cct atg acg aag cat gcg cca agc atg tgg act gat acc ttt tct aac      96
Pro Met Thr Lys His Ala Pro Ser Met Trp Thr Asp Thr Phe Ser Asn
            20                  25                  30 ttt tct ctt gac gat aag gaa caa caa aag tgc tca gaa acc atc gaa     144
Phe Ser Leu Asp Asp Lys Glu Gln Gln Lys Cys Ser Glu Thr Ile Glu
        35                  40                  45 gca ctt aag caa gaa gca aga ggc atg ctt atg gct gca acc act cct     192
Ala Leu Lys Gln Glu Ala Arg Gly Met Leu Met Ala Ala Thr Thr Pro
    50                  55                  60 ctc caa caa atg aca cta atc gac act ctc gag cgt ttg gga ttg tct     240
Leu Gln Gln Met Thr Leu Ile Asp Thr Leu Glu Arg Leu Gly Leu Ser
65                  70                  75                  80 ttc cat ttt gag acg gag atc gaa tac aaa atc gaa cta atc aac gct     288
Phe His Phe Glu Thr Glu Ile Glu Tyr Lys Ile Glu Leu Ile Asn Ala
                85                  90                  95 gca gaa gac gac ggc ttt gat ttg ttc gct act gct ctt cgt ttc cgt     336
Ala Glu Asp Asp Gly Phe Asp Leu Phe Ala Thr Ala Leu Arg Phe Arg
            100                 105                 110 ttg ctc aga caa cat caa cgc cac gtt tct tgt gat gtt ttc gac aag     384
Leu Leu Arg Gln His Gln Arg His Val Ser Cys Asp Val Phe Asp Lys
        115                 120                 125 ttc atc gac aaa gat ggc aag ttc gaa gaa tcc ctt agc aat aat gtt     432
Phe Ile Asp Lys Asp Gly Lys Phe Glu Glu Ser Leu Ser Asn Asn Val
    130                 135                 140 gaa ggc cta tta agc ttg tat gaa gca gct cat gtt ggg ttt cgc gaa     480
Glu Gly Leu Leu Ser Leu Tyr Glu Ala Ala His Val Gly Phe Arg Glu
145                 150                 155                 160 gaa aga ata tta caa gag gct gta aat ttt acg agg cat cac ttg gaa     528
Glu Arg Ile Leu Gln Glu Ala Val Asn Phe Thr Arg His His Leu Glu
```

```
                            165                 170                 175
gga gca gag tta gat cag tct cca tta ttg att aga gag aaa gtg aag       576
Gly Ala Glu Leu Asp Gln Ser Pro Leu Leu Ile Arg Glu Lys Val Lys
            180                 185                 190 cga gct ttg gag cac cct ctt cat agg gat ttc ccc att gtc tat gca       624
Arg Ala Leu Glu His Pro Leu His Arg Asp Phe Pro Ile Val Tyr Ala
            195                 200                 205 cgc ctt ttc atc tcc att tac gaa aag gat gac tct aga gat gaa tta       672
Arg Leu Phe Ile Ser Ile Tyr Glu Lys Asp Asp Ser Arg Asp Glu Leu
            210                 215                 220 ctt ctc aag cta tcc aaa gtc aac ttc aaa ttc atg cag aat ttg tat       720
Leu Leu Lys Leu Ser Lys Val Asn Phe Lys Phe Met Gln Asn Leu Tyr
225                 230                 235                 240 aag gaa gag ctc tcc caa ctc tcc agg tgg tgg aac aca tgg aat ctg       768
Lys Glu Glu Leu Ser Gln Leu Ser Arg Trp Trp Asn Thr Trp Asn Leu
                245                 250                 255 aaa tca aaa tta cca tat gca aga gat cga gtc gtg gag gct tat gtt       816
Lys Ser Lys Leu Pro Tyr Ala Arg Asp Arg Val Val Glu Ala Tyr Val
                260                 265                 270 tgg gga gta ggt tac cat tac gaa ccc caa tac tca tat gtt cga atg       864
Trp Gly Val Gly Tyr His Tyr Glu Pro Gln Tyr Ser Tyr Val Arg Met
            275                 280                 285 gga ctt gcc aaa ggc gta cta att tgt gga atc atg gac gat aca tat       912
Gly Leu Ala Lys Gly Val Leu Ile Cys Gly Ile Met Asp Asp Thr Tyr
            290                 295                 300 gat aat tat gct aca ctc aat gaa gct caa ctt ttt act caa gtc tta       960
Asp Asn Tyr Ala Thr Leu Asn Glu Ala Gln Leu Phe Thr Gln Val Leu
305                 310                 315                 320 gac aag tgg gat aga gat gaa gct gaa cga ctc cca gaa tac atg aaa      1008
Asp Lys Trp Asp Arg Asp Glu Ala Glu Arg Leu Pro Glu Tyr Met Lys
                325                 330                 335 att gtt tat cga ttt att ttg agt ata tat gaa aat tat gaa cgt gat      1056
Ile Val Tyr Arg Phe Ile Leu Ser Ile Tyr Glu Asn Tyr Glu Arg Asp
                340                 345                 350 gca gcg aaa ctt gga aaa agc ttt gca gct cct tat ttt aag gaa acc      1104
Ala Ala Lys Leu Gly Lys Ser Phe Ala Ala Pro Tyr Phe Lys Glu Thr
            355                 360                 365 gtg aaa caa ctg gca agg gca ttt aat gag gag cag aag tgg gtt atg      1152
Val Lys Gln Leu Ala Arg Ala Phe Asn Glu Glu Gln Lys Trp Val Met
370                 375                 380 gaa agg cag cta ccg tca ttc caa gac tac gta aag aat acg gag aaa      1200
Glu Arg Gln Leu Pro Ser Phe Gln Asp Tyr Val Lys Asn Thr Glu Lys
385                 390                 395                 400 acc agc tgc att tat acc atg ttt gct tct atc atc cca ggc ttg aaa      1248
Thr Ser Cys Ile Tyr Thr Met Phe Ala Ser Ile Ile Pro Gly Leu Lys
                405                 410                 415 tct gtt acc caa gaa acc att gat tgg atc aag agt gaa ccc acg ctc      1296
Ser Val Thr Gln Glu Thr Ile Asp Trp Ile Lys Ser Glu Pro Thr Leu
                420                 425                 430 gca aca tcg acc gct atg atc ggt cgg tat tgg aat gac acc agc tct      1344
Ala Thr Ser Thr Ala Met Ile Gly Arg Tyr Trp Asn Asp Thr Ser Ser
            435                 440                 445 cag ctc cgt gaa agc aaa gga ggg gaa atg ctg act gcg ttg gat ttc      1392
Gln Leu Arg Glu Ser Lys Gly Gly Glu Met Leu Thr Ala Leu Asp Phe
            450                 455                 460 cac atg aaa gaa tat ggt ctg acg aag gaa gag gcg gca tct aag ttt      1440
His Met Lys Glu Tyr Gly Leu Thr Lys Glu Glu Ala Ala Ser Lys Phe
465                 470                 475                 480 gaa gga ttg gtt gag gaa aca tgg aag gat ata aac aag gaa ttc ata      1488
```

```
                Glu Gly Leu Val Glu Glu Thr Trp Lys Asp Ile Asn Lys Glu Phe Ile
                                485                 490                 495 gcc aca act aat tat aat gtg ggt aga gaa att gcc atc aca ttc ctc          1536
Ala Thr Thr Asn Tyr Asn Val Gly Arg Glu Ile Ala Ile Thr Phe Leu
            500                 505                 510 aac tac gct cgg ata tgt gaa gcc agt tac agc aaa act gac gga gac          1584
Asn Tyr Ala Arg Ile Cys Glu Ala Ser Tyr Ser Lys Thr Asp Gly Asp
            515                 520                 525 gct tat tca gat cct aat gtt gcc aag gca aat gtc gtt gct ctc ttt          1632
Ala Tyr Ser Asp Pro Asn Val Ala Lys Ala Asn Val Val Ala Leu Phe
        530                 535                 540 gtt gat gcc ata gtc ttt                                                  1650
Val Asp Ala Ile Val Phe
545             550

<210> SEQ ID NO 17
<211> LENGTH: 550
<212> TYPE: PRT
<213> ORGANISM: Artificial Sequence

<400> SEQUENCE: 17

Met Ala Thr Asn Gly Val Val Ile Ser Cys Leu Arg Glu Val Arg Pro
 1               5                  10                  15

Pro Met Thr Lys His Ala Pro Ser Met Trp Thr Asp Thr Phe Ser Asn
                20                  25                  30

Phe Ser Leu Asp Asp Lys Glu Gln Lys Cys Ser Glu Thr Ile Glu
            35                  40                  45

Ala Leu Lys Gln Glu Ala Arg Gly Met Leu Met Ala Ala Thr Thr Pro
        50                  55                  60

Leu Gln Gln Met Thr Leu Ile Asp Thr Leu Glu Arg Leu Gly Leu Ser
65                  70                  75                  80

Phe His Phe Glu Thr Glu Ile Glu Tyr Lys Ile Glu Leu Ile Asn Ala
                85                  90                  95

Ala Glu Asp Asp Gly Phe Asp Leu Phe Ala Thr Ala Leu Arg Phe Arg
            100                 105                 110

Leu Leu Arg Gln His Gln Arg His Val Ser Cys Asp Val Phe Asp Lys
        115                 120                 125

Phe Ile Asp Lys Asp Gly Lys Phe Glu Glu Ser Leu Ser Asn Asn Val
    130                 135                 140

Glu Gly Leu Leu Ser Leu Tyr Glu Ala Ala His Val Gly Phe Arg Glu
145                 150                 155                 160

Glu Arg Ile Leu Gln Glu Ala Val Asn Phe Thr Arg His His Leu Glu
                165                 170                 175

Gly Ala Glu Leu Asp Gln Ser Pro Leu Leu Ile Arg Glu Lys Val Lys
            180                 185                 190

Arg Ala Leu Glu His Pro Leu His Arg Asp Phe Pro Ile Val Tyr Ala
        195                 200                 205

Arg Leu Phe Ile Ser Ile Tyr Glu Lys Asp Asp Ser Arg Asp Glu Leu
    210                 215                 220

Leu Leu Lys Leu Ser Lys Val Asn Phe Lys Phe Met Gln Asn Leu Tyr
225                 230                 235                 240

Lys Glu Glu Leu Ser Gln Leu Ser Arg Trp Trp Asn Thr Trp Asn Leu
                245                 250                 255

Lys Ser Lys Leu Pro Tyr Ala Arg Asp Arg Val Val Glu Ala Tyr Val
            260                 265                 270

Trp Gly Val Gly Tyr His Tyr Glu Pro Gln Tyr Ser Tyr Val Arg Met
        275                 280                 285
```

```
Gly Leu Ala Lys Gly Val Leu Ile Cys Gly Ile Met Asp Asp Thr Tyr
            290                 295                 300

Asp Asn Tyr Ala Thr Leu Asn Glu Ala Gln Leu Phe Thr Gln Val Leu
305                 310                 315                 320

Asp Lys Trp Asp Arg Asp Glu Ala Glu Arg Leu Pro Glu Tyr Met Lys
                325                 330                 335

Ile Val Tyr Arg Phe Ile Leu Ser Ile Tyr Glu Asn Tyr Glu Arg Asp
                340                 345                 350

Ala Ala Lys Leu Gly Lys Ser Phe Ala Ala Pro Tyr Phe Lys Glu Thr
            355                 360                 365

Val Lys Gln Leu Ala Arg Ala Phe Asn Glu Glu Gln Lys Trp Val Met
370                 375                 380

Glu Arg Gln Leu Pro Ser Phe Gln Asp Tyr Val Lys Asn Thr Glu Lys
385                 390                 395                 400

Thr Ser Cys Ile Tyr Thr Met Phe Ala Ser Ile Ile Pro Gly Leu Lys
                405                 410                 415

Ser Val Thr Gln Glu Thr Ile Asp Trp Ile Lys Ser Glu Pro Thr Leu
                420                 425                 430

Ala Thr Ser Thr Ala Met Ile Gly Arg Tyr Trp Asn Asp Thr Ser Ser
            435                 440                 445

Gln Leu Arg Glu Ser Lys Gly Gly Glu Met Leu Thr Ala Leu Asp Phe
450                 455                 460

His Met Lys Glu Tyr Gly Leu Thr Lys Glu Glu Ala Ala Ser Lys Phe
465                 470                 475                 480

Glu Gly Leu Val Glu Glu Thr Trp Lys Asp Ile Asn Lys Glu Phe Ile
                485                 490                 495

Ala Thr Thr Asn Tyr Asn Val Gly Arg Glu Ile Ala Ile Thr Phe Leu
            500                 505                 510

Asn Tyr Ala Arg Ile Cys Glu Ala Ser Tyr Ser Lys Thr Asp Gly Asp
            515                 520                 525

Ala Tyr Ser Asp Pro Asn Val Ala Lys Ala Asn Val Val Ala Leu Phe
530                 535                 540

Val Asp Ala Ile Val Phe
545                 550

<210> SEQ ID NO 18
<211> LENGTH: 1650
<212> TYPE: DNA
<213> ORGANISM: Artificial Sequence
<220> FEATURE:
<223> OTHER INFORMATION: Description of Artificial Sequence: nucleic
      acid sequence encoding E-beta-farnesene synthase
<220> FEATURE:
<221> NAME/KEY: CDS
<222> LOCATION: (1)..(1650)
<223> OTHER INFORMATION: Computer-generated nucleic acid sequence
      encoding peppermint E-beta-farnesene synthase protein

<400> SEQUENCE: 18 atg gct aca aac ggc gtc gta att agt tgc tta agg gaa gta agg cca      48
Met Ala Thr Asn Gly Val Val Ile Ser Cys Leu Arg Glu Val Arg Pro
  1               5                  10                  15 cct atg acg aag cat gcg cca agc atg tgg act gat acc ttt tct aac      96
Pro Met Thr Lys His Ala Pro Ser Met Trp Thr Asp Thr Phe Ser Asn
             20                  25                  30 ttt tct ctt gac gat aag gaa caa caa aag tgc tca gaa acc atc gaa     144
Phe Ser Leu Asp Asp Lys Glu Gln Gln Lys Cys Ser Glu Thr Ile Glu
         35                  40                  45
```

-continued

| | | |
|---|---|---|
| gca ctt aag caa gaa gca aga ggc atg ctt atg gct gca acc act cct<br>Ala Leu Lys Gln Glu Ala Arg Gly Met Leu Met Ala Ala Thr Thr Pro<br>50                         55                        60 | | 192 |
| ctc caa caa atg aca cta atc gac act ctc gag cgt ttg gga ttg tct<br>Leu Gln Gln Met Thr Leu Ile Asp Thr Leu Glu Arg Leu Gly Leu Ser<br>65                      70                       75                     80 | | 240 |
| ttc cat ttt gag acg gag atc gaa tac aaa atc gaa cta atc aac gct<br>Phe His Phe Glu Thr Glu Ile Glu Tyr Lys Ile Glu Leu Ile Asn Ala<br>                      85                      90                     95 | | 288 |
| gca gaa gac gac ggc ttt gat ttg ttc gct act gct ctt cgt ttc cgt<br>Ala Glu Asp Asp Gly Phe Asp Leu Phe Ala Thr Ala Leu Arg Phe Arg<br>                        100                    105                    110 | | 336 |
| ttg ctc aga caa cat caa cgc cac gtt tct tgt gat gtt ttc gac aag<br>Leu Leu Arg Gln His Gln Arg His Val Ser Cys Asp Val Phe Asp Lys<br>115                      120                    125 | | 384 |
| ttc atc gac aaa gat ggc aag ttc gaa gaa tcc ctt agc aat aat gtt<br>Phe Ile Asp Lys Asp Gly Lys Phe Glu Glu Ser Leu Ser Asn Asn Val<br>130                      135                    140 | | 432 |
| gaa ggc cta tta agc ttg tat gaa gca gct cat gtt ggg ttt cgc gaa<br>Glu Gly Leu Leu Ser Leu Tyr Glu Ala Ala His Val Gly Phe Arg Glu<br>145                      150                    155                    160 | | 480 |
| gaa aga ata tta caa gag gct gta aat ttt acg agg cat cac ttg gaa<br>Glu Arg Ile Leu Gln Glu Ala Val Asn Phe Thr Arg His His Leu Glu<br>                      165                    170                    175 | | 528 |
| gga gca gag tta gat cag tct cca tta ttg att aga gag aaa gtg aag<br>Gly Ala Glu Leu Asp Gln Ser Pro Leu Leu Ile Arg Glu Lys Val Lys<br>180                      185                    190 | | 576 |
| cga gct ttg gag cac cct ctt cat agg gat ttc ccc att gtc tat gca<br>Arg Ala Leu Glu His Pro Leu His Arg Asp Phe Pro Ile Val Tyr Ala<br>                      195                    200                    205 | | 624 |
| cgc ctt ttc atc tcc att tac gaa aag gat gac tct aga gat gaa tta<br>Arg Leu Phe Ile Ser Ile Tyr Glu Lys Asp Asp Ser Arg Asp Glu Leu<br>210                      215                    220 | | 672 |
| ctt ctc aag cta tcc aaa gtc aac ttc aaa ttc atg cag aat ttg tat<br>Leu Leu Lys Leu Ser Lys Val Asn Phe Lys Phe Met Gln Asn Leu Tyr<br>225                      230                    235                    240 | | 720 |
| aag gaa gag ctc tcc caa ctc tcc agg tgg tgg aac aca tgg aat ctg<br>Lys Glu Glu Leu Ser Gln Leu Ser Arg Trp Trp Asn Thr Trp Asn Leu<br>                      245                    250                    255 | | 768 |
| aaa tca aaa tta cca tat gca aga gat cga gtc gtg gag gct tat gtt<br>Lys Ser Lys Leu Pro Tyr Ala Arg Asp Arg Val Val Glu Ala Tyr Val<br>260                      265                    270 | | 816 |
| tgg gga gta ggt tac cat tac gaa ccc caa tac tca tat gtt cga atg<br>Trp Gly Val Gly Tyr His Tyr Glu Pro Gln Tyr Ser Tyr Val Arg Met<br>                      275                    280                    285 | | 864 |
| gga ctt gcc aaa ggc gta cta att tgt gga atc atg gac gat aca tat<br>Gly Leu Ala Lys Gly Val Leu Ile Cys Gly Ile Met Asp Asp Thr Tyr<br>290                      295                    300 | | 912 |
| gat aat tat gct aca ctc aat gaa gct caa ctt ttt act caa gtc tta<br>Asp Asn Tyr Ala Thr Leu Asn Glu Ala Gln Leu Phe Thr Gln Val Leu<br>305                      310                    315                    320 | | 960 |
| gac aag tgg gat aga gat gaa gct gaa cga ctc cca gaa tac atg aaa<br>Asp Lys Trp Asp Arg Asp Glu Ala Glu Arg Leu Pro Glu Tyr Met Lys<br>                      325                    330                    335 | | 1008 |
| atc gtt tat cga ttt att ttg agt ata tat gaa aat tat gaa cgt gat<br>Ile Val Tyr Arg Phe Ile Leu Ser Ile Tyr Glu Asn Tyr Glu Arg Asp<br>                      340                    345                    350 | | 1056 |
| gca gcg aaa ctt gga aaa agc ttt gca gct cct tat ttt aag gaa acc<br>Ala Ala Lys Leu Gly Lys Ser Phe Ala Ala Pro Tyr Phe Lys Glu Thr<br>355                      360                    365 | | 1104 |

```
gtg aaa caa ctg gca agg gca ttt aat gag gag cag aag tgg gtt atg      1152
Val Lys Gln Leu Ala Arg Ala Phe Asn Glu Glu Gln Lys Trp Val Met
370                 375                 380 gaa agg cag cta ccg tca ttc caa gac tac gta aag aat tca gag aaa      1200
Glu Arg Gln Leu Pro Ser Phe Gln Asp Tyr Val Lys Asn Ser Glu Lys
385                 390                 395                 400 acc agc tgc att tat acc atg ttt gct tct atc atc cca ggc ttg aaa      1248
Thr Ser Cys Ile Tyr Thr Met Phe Ala Ser Ile Ile Pro Gly Leu Lys
                405                 410                 415 tct gtt acc caa gaa acc att gat tgg atc aag agt gaa ccc acg ctc      1296
Ser Val Thr Gln Glu Thr Ile Asp Trp Ile Lys Ser Glu Pro Thr Leu
            420                 425                 430 gca aca tcg acc gct atg atc ggt cgg tat tgg aat gac acc agc tct      1344
Ala Thr Ser Thr Ala Met Ile Gly Arg Tyr Trp Asn Asp Thr Ser Ser
        435                 440                 445 cag ctc cgt gaa agc aaa gga ggg gaa atg ctg act gcg ttg gat ttc      1392
Gln Leu Arg Glu Ser Lys Gly Gly Glu Met Leu Thr Ala Leu Asp Phe
450                 455                 460 cac atg aaa gaa tat ggt ctg acg aag gaa gag gcg gca tct aag ttt      1440
His Met Lys Glu Tyr Gly Leu Thr Lys Glu Glu Ala Ala Ser Lys Phe
465                 470                 475                 480 gaa gga ttg gtt gag gaa aca tgg aag gat ata aac aag gaa ttc ata      1488
Glu Gly Leu Val Glu Glu Thr Trp Lys Asp Ile Asn Lys Glu Phe Ile
                485                 490                 495 gcc aca act aat tat aat gtg ggt aga gaa att gcc atc aca ttc ctc      1536
Ala Thr Thr Asn Tyr Asn Val Gly Arg Glu Ile Ala Ile Thr Phe Leu
            500                 505                 510 aac tac gct cgg ata tgt gaa gcc agt tac agc aaa act gac gga gac      1584
Asn Tyr Ala Arg Ile Cys Glu Ala Ser Tyr Ser Lys Thr Asp Gly Asp
        515                 520                 525 gct tat tca gat cct aat gtt gcc aag gca aat gtc gtt gct ctc ttt      1632
Ala Tyr Ser Asp Pro Asn Val Ala Lys Ala Asn Val Val Ala Leu Phe
530                 535                 540 gtt gat gcc gtc ata ttt                                              1650
Val Asp Ala Val Ile Phe
545                 550

<210> SEQ ID NO 19
<211> LENGTH: 550
<212> TYPE: PRT
<213> ORGANISM: Artificial Sequence

<400> SEQUENCE: 19

Met Ala Thr Asn Gly Val Val Ile Ser Cys Leu Arg Glu Val Arg Pro
1               5                   10                  15

Pro Met Thr Lys His Ala Pro Ser Met Trp Thr Asp Thr Phe Ser Asn
            20                  25                  30

Phe Ser Leu Asp Asp Lys Glu Gln Gln Lys Cys Ser Glu Thr Ile Glu
        35                  40                  45

Ala Leu Lys Gln Glu Ala Arg Gly Met Leu Met Ala Ala Thr Thr Pro
    50                  55                  60

Leu Gln Gln Met Thr Leu Ile Asp Thr Leu Glu Arg Leu Gly Leu Ser
65                  70                  75                  80

Phe His Phe Glu Thr Glu Ile Glu Tyr Lys Ile Glu Leu Ile Asn Ala
                85                  90                  95

Ala Glu Asp Asp Gly Phe Asp Leu Phe Ala Thr Ala Leu Arg Phe Arg
            100                 105                 110

Leu Leu Arg Gln His Gln Arg His Val Ser Cys Asp Val Phe Asp Lys
        115                 120                 125
```

-continued

```
Phe Ile Asp Lys Asp Gly Lys Phe Glu Glu Ser Leu Ser Asn Asn Val
    130                 135                 140
Glu Gly Leu Leu Ser Leu Tyr Glu Ala Ala His Val Gly Phe Arg Glu
145                 150                 155                 160
Glu Arg Ile Leu Gln Glu Ala Val Asn Phe Thr Arg His His Leu Glu
                165                 170                 175
Gly Ala Glu Leu Asp Gln Ser Pro Leu Leu Ile Arg Glu Lys Val Lys
                180                 185                 190
Arg Ala Leu Glu His Pro Leu His Arg Asp Phe Pro Ile Val Tyr Ala
            195                 200                 205
Arg Leu Phe Ile Ser Ile Tyr Glu Lys Asp Asp Ser Arg Asp Glu Leu
            210                 215                 220
Leu Leu Lys Leu Ser Lys Val Asn Phe Lys Phe Met Gln Asn Leu Tyr
225                 230                 235                 240
Lys Glu Glu Leu Ser Gln Leu Ser Arg Trp Trp Asn Thr Trp Asn Leu
                245                 250                 255
Lys Ser Lys Leu Pro Tyr Ala Arg Asp Arg Val Val Glu Ala Tyr Val
                260                 265                 270
Trp Gly Val Gly Tyr His Tyr Glu Pro Gln Tyr Ser Tyr Val Arg Met
            275                 280                 285
Gly Leu Ala Lys Gly Val Leu Ile Cys Gly Ile Met Asp Asp Thr Tyr
            290                 295                 300
Asp Asn Tyr Ala Thr Leu Asn Glu Ala Gln Leu Phe Thr Gln Val Leu
305                 310                 315                 320
Asp Lys Trp Asp Arg Asp Glu Ala Glu Arg Leu Pro Glu Tyr Met Lys
                325                 330                 335
Ile Val Tyr Arg Phe Ile Leu Ser Ile Tyr Glu Asn Tyr Glu Arg Asp
                340                 345                 350
Ala Ala Lys Leu Gly Lys Ser Phe Ala Ala Pro Tyr Phe Lys Glu Thr
            355                 360                 365
Val Lys Gln Leu Ala Arg Ala Phe Asn Glu Glu Gln Lys Trp Val Met
            370                 375                 380
Glu Arg Gln Leu Pro Ser Phe Gln Asp Tyr Val Lys Asn Ser Glu Lys
385                 390                 395                 400
Thr Ser Cys Ile Tyr Thr Met Phe Ala Ser Ile Ile Pro Gly Leu Lys
                405                 410                 415
Ser Val Thr Gln Glu Thr Ile Asp Trp Ile Lys Ser Glu Pro Thr Leu
                420                 425                 430
Ala Thr Ser Thr Ala Met Ile Gly Arg Tyr Trp Asn Asp Thr Ser Ser
            435                 440                 445
Gln Leu Arg Glu Ser Lys Gly Gly Glu Met Leu Thr Ala Leu Asp Phe
            450                 455                 460
His Met Lys Glu Tyr Gly Leu Thr Lys Glu Glu Ala Ala Ser Lys Phe
465                 470                 475                 480
Glu Gly Leu Val Glu Glu Thr Trp Lys Asp Ile Asn Lys Glu Phe Ile
                485                 490                 495
Ala Thr Thr Asn Tyr Asn Val Gly Arg Glu Ile Ala Ile Thr Phe Leu
                500                 505                 510
Asn Tyr Ala Arg Ile Cys Glu Ala Ser Tyr Ser Lys Thr Asp Gly Asp
            515                 520                 525
Ala Tyr Ser Asp Pro Asn Val Ala Lys Ala Asn Val Val Ala Leu Phe
            530                 535                 540
Val Asp Ala Val Ile Phe
545                 550
```

```
<210> SEQ ID NO 20
<211> LENGTH: 550
<212> TYPE: PRT
<213> ORGANISM: Artificial Sequence
<220> FEATURE:
<223> OTHER INFORMATION: Description of Artificial Sequence:
      E-beta-farnesene synthase protein
<220> FEATURE:
<221> NAME/KEY: VARIANT
<222> LOCATION: (1)..(550)
<223> OTHER INFORMATION: Computer-generated E-beta-farnesene synthase
      protein variant

<400> SEQUENCE: 20

Met Ala Thr Asn Gly Val Leu Ile Ser Cys Leu Arg Glu Val Arg Pro
  1               5                  10                  15

Pro Met Thr Lys His Ala Pro Ser Met Trp Thr Asp Thr Phe Ser Asn
                 20                  25                  30

Phe Ser Leu Asp Asp Lys Glu Gln Gln Lys Cys Ser Glu Thr Ile Glu
             35                  40                  45

Ala Leu Lys Gln Glu Ala Arg Gly Met Leu Met Ala Ala Thr Thr Pro
         50                  55                  60

Leu Gln Gln Met Thr Leu Ile Asp Thr Leu Glu Arg Leu Gly Leu Ser
 65                  70                  75                  80

Phe His Phe Glu Thr Glu Ile Glu Tyr Lys Ile Glu Leu Ile Asn Ala
                 85                  90                  95

Ala Glu Asp Asp Gly Phe Asp Leu Phe Ala Thr Ala Leu Arg Phe Arg
            100                 105                 110

Leu Leu Arg Gln His Gln Arg His Val Ser Cys Asp Val Phe Asp Lys
        115                 120                 125

Phe Ile Asp Lys Asp Gly Lys Phe Glu Glu Ser Leu Ser Asn Asn Val
130                 135                 140

Glu Gly Leu Leu Ser Leu Tyr Glu Ala Ala His Val Gly Phe Arg Glu
145                 150                 155                 160

Glu Arg Ile Leu Gln Glu Ala Val Asn Phe Thr Arg His His Leu Glu
                165                 170                 175

Gly Ala Glu Leu Asp Gln Ser Pro Leu Leu Ile Arg Glu Lys Val Lys
            180                 185                 190

Arg Ala Leu Glu His Pro Leu His Arg Asp Phe Pro Ile Val Tyr Ala
        195                 200                 205

Arg Leu Phe Ile Ser Ile Tyr Glu Lys Asp Asp Ser Arg Asp Glu Leu
210                 215                 220

Leu Leu Lys Leu Ser Lys Val Asn Phe Lys Phe Met Gln Asn Leu Tyr
225                 230                 235                 240

Lys Glu Glu Leu Ser Gln Leu Ser Arg Trp Trp Asn Thr Trp Asn Leu
                245                 250                 255

Lys Ser Lys Leu Pro Tyr Ala Arg Asp Arg Val Val Glu Ala Tyr Val
            260                 265                 270

Trp Gly Val Gly Tyr His Tyr Glu Pro Gln Tyr Ser Tyr Val Arg Met
        275                 280                 285

Gly Leu Ala Lys Gly Val Leu Ile Cys Gly Ile Met Asp Asp Thr Tyr
290                 295                 300

Asp Asn Tyr Ala Thr Leu Asn Glu Ala Gln Leu Phe Thr Gln Val Leu
305                 310                 315                 320

Asp Lys Trp Asp Arg Asp Glu Ala Glu Arg Leu Pro Glu Tyr Met Lys
                325                 330                 335
```

```
Ile Val Tyr Arg Phe Ile Leu Ser Ile Tyr Glu Asn Tyr Glu Arg Asp
            340                 345                 350

Ala Ala Lys Leu Gly Lys Ser Phe Ala Ala Pro Tyr Phe Lys Glu Thr
            355                 360                 365

Val Lys Gln Leu Ala Arg Ala Phe Asn Glu Glu Gln Lys Trp Val Met
370                 375                 380

Glu Arg Gln Leu Pro Ser Phe Gln Asp Tyr Val Lys Asn Ser Glu Lys
385                 390                 395                 400

Thr Ser Cys Ile Tyr Thr Met Phe Ala Ser Ile Ile Pro Gly Leu Lys
                405                 410                 415

Ser Val Thr Gln Glu Thr Ile Asp Trp Ile Lys Ser Glu Pro Thr Leu
                420                 425                 430

Ala Thr Ser Thr Ala Met Ile Gly Arg Tyr Trp Asn Asp Thr Ser Ser
            435                 440                 445

Gln Leu Arg Glu Ser Lys Gly Gly Glu Met Leu Thr Ala Leu Asp Phe
450                 455                 460

His Met Lys Glu Tyr Gly Leu Thr Lys Glu Glu Ala Ala Ser Lys Phe
465                 470                 475                 480

Glu Gly Leu Val Glu Glu Thr Trp Lys Asp Ile Asn Lys Glu Phe Ile
                485                 490                 495

Ala Thr Thr Asn Tyr Asn Val Gly Arg Glu Ile Ala Ile Thr Phe Leu
                500                 505                 510

Asn Tyr Ala Arg Ile Cys Glu Ala Ser Tyr Ser Lys Thr Asp Gly Asp
            515                 520                 525

Ala Tyr Ser Asp Pro Asn Val Ala Lys Ala Asn Val Val Ala Leu Tyr
530                 535                 540

Val Asp Ala Ile Val Phe
545                 550

<210> SEQ ID NO 21
<211> LENGTH: 550
<212> TYPE: PRT
<213> ORGANISM: Artificial Sequence
<220> FEATURE:
<223> OTHER INFORMATION: Description of Artificial Sequence:
      E-beta-farnesene synthase protein
<220> FEATURE:
<221> NAME/KEY: VARIANT
<222> LOCATION: (1)..(550)
<223> OTHER INFORMATION: Computer-generated E-beta-farnesene synthase
      protein variant

<400> SEQUENCE: 21

Met Ala Thr Asn Gly Val Val Ile Ser Cys Leu Arg Glu Val Arg Pro
1               5                   10                  15

Pro Met Thr Lys His Gly Pro Ser Met Trp Thr Asp Thr Phe Ser Asn
            20                  25                  30

Phe Ser Leu Asp Asp Lys Glu Gln Gln Lys Cys Ser Glu Thr Ile Glu
        35                  40                  45

Ala Leu Lys Gln Glu Ala Arg Gly Met Leu Met Ala Ala Thr Thr Pro
    50                  55                  60

Leu Gln Gln Met Thr Leu Ile Asp Thr Leu Glu Arg Leu Gly Leu Ser
65                  70                  75                  80

Phe His Phe Glu Thr Glu Ile Glu Tyr Lys Ile Glu Leu Ile Asn Ala
                85                  90                  95

Ala Glu Asp Asp Gly Phe Asp Leu Phe Ala Thr Ala Leu Arg Phe Arg
            100                 105                 110

Leu Leu Arg Gln His Gln Arg His Val Ser Cys Asp Val Phe Asp Lys
```

-continued

```
                115                 120                 125
Phe Ile Asp Lys Asp Gly Lys Phe Glu Glu Ser Leu Ser Asn Asn Val
    130                 135                 140
Glu Gly Leu Leu Ser Leu Tyr Glu Ala Ala His Val Gly Phe Arg Glu
145                 150                 155                 160
Glu Arg Ile Leu Gln Glu Ala Val Asn Phe Thr Arg His His Leu Glu
                165                 170                 175
Gly Ala Glu Leu Asp Gln Ser Pro Leu Leu Ile Arg Glu Lys Val Lys
                180                 185                 190
Arg Ala Leu Glu His Pro Leu His Arg Asp Phe Pro Ile Val Tyr Ala
            195                 200                 205
Arg Leu Phe Ile Ser Ile Tyr Glu Lys Asp Asp Ser Arg Asp Glu Leu
210                 215                 220
Leu Leu Lys Leu Ser Lys Val Asn Phe Lys Phe Met Gln Asn Leu Tyr
225                 230                 235                 240
Lys Glu Glu Leu Ser Gln Leu Ser Arg Trp Trp Asn Thr Trp Asn Leu
                245                 250                 255
Lys Ser Lys Leu Pro Tyr Ala Arg Asp Arg Val Val Glu Ala Tyr Val
                260                 265                 270
Trp Gly Val Gly Tyr His Tyr Glu Pro Gln Tyr Ser Tyr Val Arg Met
            275                 280                 285
Gly Leu Ala Lys Gly Val Leu Ile Cys Gly Ile Met Asp Asp Thr Tyr
290                 295                 300
Asp Asn Tyr Ala Thr Leu Asn Glu Ala Gln Leu Phe Thr Gln Val Leu
305                 310                 315                 320
Asp Lys Trp Asp Arg Asp Glu Ala Glu Arg Leu Pro Glu Tyr Met Lys
                325                 330                 335
Ile Val Tyr Arg Phe Ile Leu Ser Ile Tyr Glu Asn Tyr Glu Arg Asp
                340                 345                 350
Ala Ala Lys Leu Gly Lys Ser Phe Ala Ala Pro Tyr Phe Lys Glu Thr
            355                 360                 365
Val Lys Gln Leu Ala Arg Ala Phe Asn Glu Glu Gln Lys Trp Val Met
370                 375                 380
Glu Arg Gln Leu Pro Ser Phe Gln Asp Tyr Val Lys Asn Ser Glu Lys
385                 390                 395                 400
Thr Ser Cys Ile Tyr Thr Met Phe Ala Ser Ile Ile Pro Gly Leu Lys
                405                 410                 415
Ser Val Thr Gln Glu Thr Ile Asp Trp Ile Lys Ser Glu Pro Thr Leu
                420                 425                 430
Ala Thr Ser Thr Ala Met Ile Gly Arg Tyr Trp Asn Asp Thr Ser Ser
            435                 440                 445
Gln Leu Arg Glu Ser Lys Gly Gly Glu Met Leu Thr Ala Leu Asp Phe
450                 455                 460
His Met Lys Glu Tyr Gly Leu Thr Lys Glu Glu Ala Ala Ser Lys Phe
465                 470                 475                 480
Glu Gly Leu Val Glu Glu Thr Trp Lys Asp Ile Asn Lys Glu Phe Ile
                485                 490                 495
Ala Thr Thr Asn Tyr Asn Val Gly Arg Glu Ile Ala Ile Thr Phe Leu
                500                 505                 510
Asn Tyr Ala Arg Ile Cys Glu Ala Ser Tyr Ser Lys Thr Asp Gly Asp
            515                 520                 525
Ala Tyr Ser Asp Pro Asn Val Ala Lys Ala Asn Val Val Ala Leu Phe
530                 535                 540
```

```
Val Asp Ala Ile Val Phe
545                 550

<210> SEQ ID NO 22
<211> LENGTH: 550
<212> TYPE: PRT
<213> ORGANISM: Artificial Sequence
<220> FEATURE:
<223> OTHER INFORMATION: Description of Artificial Sequence:
      E-beta-farnesene synthase protein
<220> FEATURE:
<221> NAME/KEY: VARIANT
<222> LOCATION: (1)..(550)
<223> OTHER INFORMATION: Computer-generated E-beta-farnesene synthase
      protein variant

<400> SEQUENCE: 22

Met Ala Thr Asn Gly Val Val Ile Ser Cys Leu Arg Glu Val Arg Pro
1               5                   10                  15

Pro Met Thr Lys His Ala Pro Ser Met Trp Thr Asp Thr Phe Ser Asn
            20                  25                  30

Phe Ser Leu Asp Asp Lys Glu Gln Gln Lys Cys Ser Glu Thr Ile Glu
        35                  40                  45

Ala Leu Lys Gln Glu Ala Arg Gly Met Leu Met Ala Ala Thr Thr Pro
    50                  55                  60

Leu Gln Gln Met Thr Leu Ile Asp Thr Leu Glu Arg Leu Gly Leu Ser
65                  70                  75                  80

Phe His Phe Glu Thr Glu Ile Glu Tyr Lys Ile Glu Leu Ile Asn Ala
                85                  90                  95

Ala Glu Asp Asp Gly Phe Asp Leu Phe Ala Thr Ala Leu Arg Phe Arg
            100                 105                 110

Leu Leu Arg Gln His Gln Arg His Val Ser Cys Asp Val Phe Glu Lys
        115                 120                 125

Phe Ile Asp Lys Asp Gly Lys Phe Glu Glu Ser Leu Ser Asn Asn Val
    130                 135                 140

Glu Gly Leu Leu Ser Leu Tyr Glu Ala Ala His Val Gly Phe Arg Glu
145                 150                 155                 160

Glu Arg Ile Leu Gln Glu Ala Val Asn Phe Thr Arg His His Leu Glu
                165                 170                 175

Gly Ala Glu Leu Asp Gln Ser Pro Leu Leu Ile Arg Glu Lys Val Lys
            180                 185                 190

Arg Ala Leu Glu His Pro Leu His Arg Asp Phe Pro Ile Val Tyr Ala
        195                 200                 205

Arg Leu Phe Ile Ser Ile Tyr Glu Lys Asp Asp Ser Arg Asp Glu Leu
    210                 215                 220

Leu Leu Lys Leu Ser Lys Val Asn Phe Lys Phe Met Gln Asn Leu Tyr
225                 230                 235                 240

Lys Glu Glu Leu Ser Gln Leu Ser Arg Trp Trp Asn Thr Trp Asn Leu
                245                 250                 255

Lys Ser Lys Leu Pro Tyr Ala Arg Asp Arg Val Val Glu Ala Tyr Val
            260                 265                 270

Trp Gly Val Gly Tyr His Tyr Glu Pro Gln Tyr Ser Tyr Val Arg Met
        275                 280                 285

Gly Leu Ala Lys Gly Val Leu Ile Cys Gly Ile Met Asp Asp Thr Tyr
    290                 295                 300

Asp Asn Tyr Ala Thr Leu Asn Glu Ala Gln Leu Phe Thr Gln Val Leu
305                 310                 315                 320

Asp Lys Trp Asp Arg Asp Glu Ala Glu Arg Leu Pro Glu Tyr Met Lys
```

```
                    325                 330                 335
Ile Val Tyr Arg Phe Ile Leu Ser Ile Tyr Glu Asn Tyr Glu Arg Asp
                340                 345                 350

Ala Ala Lys Leu Gly Lys Ser Phe Ala Pro Tyr Phe Lys Glu Thr
            355                 360                 365

Val Lys Gln Leu Ala Arg Ala Phe Asn Glu Glu Gln Lys Trp Val Met
        370                 375                 380

Glu Arg Gln Leu Pro Ser Phe Gln Asp Tyr Val Lys Asn Ser Glu Lys
385                 390                 395                 400

Thr Ser Cys Ile Tyr Thr Met Phe Ala Ser Ile Pro Gly Leu Lys
            405                 410                 415

Ser Val Thr Gln Glu Thr Ile Asp Trp Ile Lys Ser Glu Pro Thr Leu
            420                 425                 430

Ala Thr Ser Thr Ala Met Ile Gly Arg Tyr Trp Asn Asp Thr Ser Ser
            435                 440                 445

Gln Leu Arg Glu Ser Lys Gly Gly Glu Met Leu Thr Ala Leu Asp Phe
            450                 455                 460

His Met Lys Glu Tyr Gly Leu Thr Lys Glu Glu Ala Ala Ser Lys Phe
465                 470                 475                 480

Glu Gly Leu Val Glu Glu Thr Trp Lys Asp Ile Asn Lys Glu Phe Ile
                485                 490                 495

Ala Thr Thr Asn Tyr Asn Val Gly Arg Glu Ile Ala Ile Thr Phe Leu
                500                 505                 510

Asn Tyr Ala Arg Ile Cys Glu Ala Ser Tyr Ser Lys Thr Asp Gly Asp
            515                 520                 525

Ala Tyr Ser Asp Pro Asn Val Ala Lys Ala Asn Val Val Ala Leu Phe
            530                 535                 540

Val Asp Ala Ile Val Phe
545                 550

<210> SEQ ID NO 23
<211> LENGTH: 550
<212> TYPE: PRT
<213> ORGANISM: Artificial Sequence
<220> FEATURE:
<223> OTHER INFORMATION: Description of Artificial Sequence:
      E-beta-farnesene synthase protein
<220> FEATURE:
<221> NAME/KEY: VARIANT
<222> LOCATION: (1)..(550)
<223> OTHER INFORMATION: Computer-generated E-beta-farnesene synthase
      protein variant

<400> SEQUENCE: 23

Met Ala Thr Asn Gly Val Val Ile Ser Cys Leu Arg Glu Val Arg Pro
1               5                   10                  15

Pro Met Thr Lys His Ala Pro Ser Met Trp Thr Asp Thr Phe Ser Asn
                20                  25                  30

Phe Ser Leu Asp Asp Lys Glu Gln Gln Lys Cys Ser Glu Thr Ile Glu
            35                  40                  45

Ala Leu Lys Gln Glu Ala Arg Gly Met Leu Met Ala Ala Thr Thr Pro
        50                  55                  60

Leu Gln Gln Met Thr Leu Ile Asp Thr Leu Glu Arg Leu Gly Leu Ser
65                  70                  75                  80

Phe His Phe Glu Thr Glu Ile Glu Tyr Lys Ile Glu Leu Ile Asn Ala
                85                  90                  95

Ala Glu Asp Asp Gly Phe Asp Leu Phe Ala Thr Ala Leu Arg Phe Arg
            100                 105                 110
```

Leu Leu Arg Gln His Gln Arg His Val Ser Cys Asp Val Phe Asp Lys
            115                 120                 125

Phe Ile Asp Lys Asp Gly Lys Phe Glu Glu Ser Leu Ser Asn Asn Val
        130                 135                 140

Glu Gly Leu Leu Ser Leu Tyr Glu Ala Gly His Val Gly Phe Arg Glu
145                 150                 155                 160

Glu Arg Ile Leu Gln Glu Ala Val Asn Phe Thr Arg His His Leu Glu
                165                 170                 175

Gly Ala Glu Leu Asp Gln Ser Pro Leu Leu Ile Arg Glu Lys Val Lys
            180                 185                 190

Arg Ala Leu Glu His Pro Leu His Arg Asp Phe Pro Ile Val Tyr Ala
            195                 200                 205

Arg Leu Phe Ile Ser Ile Tyr Glu Lys Asp Asp Ser Arg Asp Glu Leu
        210                 215                 220

Leu Leu Lys Leu Ser Lys Val Asn Phe Lys Phe Met Gln Asn Leu Tyr
225                 230                 235                 240

Lys Glu Glu Leu Ser Gln Leu Ser Arg Trp Trp Asn Thr Trp Asn Leu
                245                 250                 255

Lys Ser Lys Leu Pro Tyr Ala Arg Asp Arg Val Val Glu Ala Tyr Val
            260                 265                 270

Trp Gly Val Gly Tyr His Tyr Glu Pro Gln Tyr Ser Tyr Val Arg Met
            275                 280                 285

Gly Leu Ala Lys Gly Val Leu Ile Cys Gly Ile Met Asp Asp Thr Tyr
        290                 295                 300

Asp Asn Tyr Ala Thr Leu Asn Glu Ala Gln Leu Phe Thr Gln Val Leu
305                 310                 315                 320

Asp Lys Trp Asp Arg Asp Glu Ala Glu Arg Leu Pro Glu Tyr Met Lys
                325                 330                 335

Ile Val Tyr Arg Phe Ile Leu Ser Ile Tyr Glu Asn Tyr Glu Arg Asp
            340                 345                 350

Ala Ala Lys Leu Gly Lys Ser Phe Ala Ala Pro Tyr Phe Lys Glu Thr
            355                 360                 365

Val Lys Gln Leu Ala Arg Ala Phe Asn Glu Glu Gln Lys Trp Val Met
        370                 375                 380

Glu Arg Gln Leu Pro Ser Phe Gln Asp Tyr Val Lys Asn Ser Glu Lys
385                 390                 395                 400

Thr Ser Cys Ile Tyr Thr Met Phe Ala Ser Ile Ile Pro Gly Leu Lys
                405                 410                 415

Ser Val Thr Gln Glu Thr Ile Asp Trp Ile Lys Ser Glu Pro Thr Leu
            420                 425                 430

Ala Thr Ser Thr Ala Met Ile Gly Arg Tyr Trp Asn Asp Thr Ser Ser
            435                 440                 445

Gln Leu Arg Glu Ser Lys Gly Gly Glu Met Leu Thr Ala Leu Asp Phe
        450                 455                 460

His Met Lys Glu Tyr Gly Leu Thr Lys Glu Glu Ala Ala Ser Lys Phe
465                 470                 475                 480

Glu Gly Leu Val Glu Glu Thr Trp Lys Asp Ile Asn Lys Glu Phe Ile
                485                 490                 495

Ala Thr Thr Asn Tyr Asn Val Gly Arg Glu Ile Ala Ile Thr Phe Leu
            500                 505                 510

Asn Tyr Ala Arg Ile Cys Glu Ala Ser Tyr Ser Lys Thr Asp Gly Asp
            515                 520                 525

Ala Tyr Ser Asp Pro Asn Val Ala Lys Ala Asn Val Val Ala Leu Phe

```
                                530                  535                  540
Val Asp Ala Ile Val Phe
545                 550

<210> SEQ ID NO 24
<211> LENGTH: 550
<212> TYPE: PRT
<213> ORGANISM: Artificial Sequence
<220> FEATURE:
<223> OTHER INFORMATION: Description of Artificial Sequence:
      E-beta-farnesene synthase protein
<220> FEATURE:
<221> NAME/KEY: VARIANT
<222> LOCATION: (1)..(550)
<223> OTHER INFORMATION: Computer-generated E-beta-farnesene synthase
      protein variant

<400> SEQUENCE: 24

Met Ala Thr Asn Gly Val Val Ile Ser Cys Leu Arg Glu Val Arg Pro
 1               5                  10                  15

Pro Met Thr Lys His Ala Pro Ser Met Trp Thr Asp Thr Phe Ser Asn
             20                  25                  30

Phe Ser Leu Asp Asp Lys Glu Gln Gln Lys Cys Ser Glu Thr Ile Glu
         35                  40                  45

Ala Leu Lys Gln Glu Ala Arg Gly Met Leu Met Ala Ala Thr Thr Pro
     50                  55                  60

Leu Gln Gln Met Thr Leu Ile Asp Thr Leu Glu Arg Leu Gly Leu Ser
 65                  70                  75                  80

Phe His Phe Glu Thr Glu Ile Glu Tyr Lys Ile Glu Leu Ile Asn Ala
                 85                  90                  95

Ala Glu Asp Asp Gly Phe Asp Leu Phe Ala Thr Ala Leu Arg Phe Arg
            100                 105                 110

Leu Leu Arg Gln His Gln Arg His Val Ser Cys Asp Val Phe Asp Lys
        115                 120                 125

Phe Ile Asp Lys Asp Gly Lys Phe Glu Glu Ser Leu Ser Asn Asn Val
    130                 135                 140

Glu Gly Leu Leu Ser Leu Tyr Glu Ala Ala His Val Gly Phe Arg Glu
145                 150                 155                 160

Glu Arg Ile Leu Gln Glu Ala Val Asn Phe Ser Arg His His Leu Glu
                165                 170                 175

Gly Ala Glu Leu Asp Gln Ser Pro Leu Leu Ile Arg Glu Lys Val Lys
            180                 185                 190

Arg Ala Leu Glu His Pro Leu His Arg Asp Phe Pro Ile Val Tyr Ala
        195                 200                 205

Arg Leu Phe Ile Ser Ile Tyr Glu Lys Asp Asp Ser Arg Asp Glu Leu
    210                 215                 220

Leu Leu Lys Leu Ser Lys Val Asn Phe Lys Phe Met Gln Asn Leu Tyr
225                 230                 235                 240

Lys Glu Glu Leu Ser Gln Leu Ser Arg Trp Trp Asn Thr Trp Asn Leu
                245                 250                 255

Lys Ser Lys Leu Pro Tyr Ala Arg Asp Arg Val Val Glu Ala Tyr Val
            260                 265                 270

Trp Gly Val Gly Tyr His Tyr Glu Pro Gln Tyr Ser Tyr Val Arg Met
        275                 280                 285

Gly Leu Ala Lys Gly Val Leu Ile Cys Gly Ile Met Asp Asp Thr Tyr
    290                 295                 300

Asp Asn Tyr Ala Thr Leu Asn Glu Ala Gln Leu Phe Thr Gln Val Leu
305                 310                 315                 320
```

Asp Lys Trp Asp Arg Asp Glu Ala Glu Arg Leu Pro Glu Tyr Met Lys
            325                 330                 335

Ile Val Tyr Arg Phe Ile Leu Ser Ile Tyr Glu Asn Tyr Glu Arg Asp
            340                 345                 350

Ala Ala Lys Leu Gly Lys Ser Phe Ala Ala Pro Tyr Phe Lys Glu Thr
            355                 360                 365

Val Lys Gln Leu Ala Arg Ala Phe Asn Glu Glu Gln Lys Trp Val Met
            370                 375                 380

Glu Arg Gln Leu Pro Ser Phe Gln Asp Tyr Val Lys Asn Ser Glu Lys
385                 390                 395                 400

Thr Ser Cys Ile Tyr Thr Met Phe Ala Ser Ile Ile Pro Gly Leu Lys
            405                 410                 415

Ser Val Thr Gln Glu Thr Ile Asp Trp Ile Lys Ser Glu Pro Thr Leu
            420                 425                 430

Ala Thr Ser Thr Ala Met Ile Gly Arg Tyr Trp Asn Asp Thr Ser Ser
            435                 440                 445

Gln Leu Arg Glu Ser Lys Gly Gly Met Leu Thr Ala Leu Asp Phe
450                 455                 460

His Met Lys Glu Tyr Gly Leu Thr Lys Glu Glu Ala Ala Ser Lys Phe
465                 470                 475                 480

Glu Gly Leu Val Glu Glu Thr Trp Lys Asp Ile Asn Lys Glu Phe Ile
            485                 490                 495

Ala Thr Thr Asn Tyr Asn Val Gly Arg Glu Ile Ala Ile Thr Phe Leu
            500                 505                 510

Asn Tyr Ala Arg Ile Cys Glu Ala Ser Tyr Ser Lys Thr Asp Gly Asp
            515                 520                 525

Ala Tyr Ser Asp Pro Asn Val Ala Lys Ala Asn Val Val Ala Leu Phe
            530                 535                 540

Val Asp Ala Ile Val Phe
545                 550

<210> SEQ ID NO 25
<211> LENGTH: 550
<212> TYPE: PRT
<213> ORGANISM: Artificial Sequence
<220> FEATURE:
<223> OTHER INFORMATION: Description of Artificial Sequence:
      E-beta-farnesene synthase protein
<220> FEATURE:
<221> NAME/KEY: VARIANT
<222> LOCATION: (1)..(550)
<223> OTHER INFORMATION: Computer-generated E-beta-farnesene synthase
      protein variant

<400> SEQUENCE: 25

Met Ala Thr Asn Gly Val Val Ile Ser Cys Leu Arg Glu Val Arg Pro
1               5                   10                  15

Pro Met Thr Lys His Ala Pro Ser Met Trp Thr Asp Thr Phe Ser Asn
            20                  25                  30

Phe Ser Leu Asp Asp Lys Glu Gln Gln Lys Cys Ser Glu Thr Ile Glu
            35                  40                  45

Ala Leu Lys Gln Glu Ala Arg Gly Met Leu Met Ala Ala Thr Thr Pro
        50                  55                  60

Leu Gln Gln Met Thr Leu Ile Asp Thr Leu Glu Arg Leu Gly Leu Ser
65                  70                  75                  80

Phe His Phe Glu Thr Glu Ile Glu Tyr Lys Ile Glu Leu Ile Asn Ala
                85                  90                  95

-continued

```
Ala Glu Asp Asp Gly Phe Asp Leu Phe Ala Thr Ala Leu Arg Phe Arg
            100                 105                 110

Leu Leu Arg Gln His Gln Arg His Val Ser Cys Asp Val Phe Asp Lys
        115                 120                 125

Phe Ile Asp Lys Asp Gly Lys Phe Glu Glu Ser Leu Ser Asn Asn Val
130                 135                 140

Glu Gly Leu Leu Ser Leu Tyr Glu Ala Ala His Val Gly Phe Arg Glu
145                 150                 155                 160

Glu Arg Ile Leu Gln Glu Ala Val Asn Phe Thr Arg His His Leu Glu
                165                 170                 175

Gly Ala Glu Leu Asp Gln Ser Pro Leu Leu Ile Arg Glu Lys Val Lys
            180                 185                 190

Arg Ala Leu Glu His Pro Leu His Arg Asp Phe Pro Ile Val Tyr Ala
        195                 200                 205

Arg Leu Phe Ile Thr Ile Tyr Glu Lys Asp Asp Ser Arg Asp Glu Leu
210                 215                 220

Leu Leu Lys Leu Ser Lys Val Asn Phe Lys Phe Met Gln Asn Leu Tyr
225                 230                 235                 240

Lys Glu Glu Leu Ser Gln Leu Ser Arg Trp Trp Asn Thr Trp Asn Leu
                245                 250                 255

Lys Ser Lys Leu Pro Tyr Ala Arg Asp Arg Val Val Glu Ala Tyr Val
            260                 265                 270

Trp Gly Val Gly Tyr His Tyr Glu Pro Gln Tyr Ser Tyr Val Arg Met
        275                 280                 285

Gly Leu Ala Lys Gly Val Leu Ile Cys Gly Ile Met Asp Asp Thr Tyr
290                 295                 300

Asp Asn Tyr Ala Thr Leu Asn Glu Ala Gln Leu Phe Thr Gln Val Leu
305                 310                 315                 320

Asp Lys Trp Asp Arg Asp Glu Ala Glu Arg Leu Pro Glu Tyr Met Lys
                325                 330                 335

Ile Val Tyr Arg Phe Ile Leu Ser Ile Tyr Glu Asn Tyr Glu Arg Asp
            340                 345                 350

Ala Ala Lys Leu Gly Lys Ser Phe Ala Ala Pro Tyr Phe Lys Glu Thr
        355                 360                 365

Val Lys Gln Leu Ala Arg Ala Phe Asn Glu Glu Gln Lys Trp Val Met
370                 375                 380

Glu Arg Gln Leu Pro Ser Phe Gln Asp Tyr Val Lys Asn Ser Glu Lys
385                 390                 395                 400

Thr Ser Cys Ile Tyr Ser Met Phe Ala Ser Ile Ile Pro Gly Leu Lys
                405                 410                 415

Ser Val Thr Gln Glu Thr Ile Asp Trp Ile Lys Ser Glu Pro Thr Leu
            420                 425                 430

Ala Thr Ser Thr Ala Met Ile Gly Arg Tyr Trp Asn Asp Thr Ser Ser
        435                 440                 445

Gln Leu Arg Glu Ser Lys Gly Gly Glu Met Leu Thr Ala Leu Asp Phe
450                 455                 460

His Met Lys Glu Tyr Gly Leu Thr Lys Glu Glu Ala Ala Ser Lys Phe
465                 470                 475                 480

Glu Gly Leu Val Glu Glu Thr Trp Lys Asp Ile Asn Lys Glu Phe Ile
                485                 490                 495

Ala Thr Thr Asn Tyr Asn Val Gly Arg Glu Ile Ala Ile Thr Phe Leu
            500                 505                 510

Asn Tyr Ala Arg Val Cys Glu Ala Ser Tyr Thr Lys Thr Asp Gly Asp
        515                 520                 525
```

```
Ala Tyr Ser Asp Pro Asn Val Ala Lys Ala Asn Val Val Ala Leu Phe
        530                 535                 540

Val Asp Ala Ile Val Phe
545                 550

<210> SEQ ID NO 26
<211> LENGTH: 550
<212> TYPE: PRT
<213> ORGANISM: Artificial Sequence
<220> FEATURE:
<223> OTHER INFORMATION: Description of Artificial Sequence:
      E-beta-farnesene synthase protein
<220> FEATURE:
<221> NAME/KEY: VARIANT
<222> LOCATION: (1)..(550)
<223> OTHER INFORMATION: Computer-generated E-beta-farnesene synthase
      protein variant

<400> SEQUENCE: 26

Met Ala Thr Asn Gly Val Val Ile Ser Cys Leu Arg Glu Val Arg Pro
  1               5                  10                  15

Pro Met Thr Lys His Ala Pro Ser Met Trp Thr Asp Thr Phe Ser Asn
             20                  25                  30

Phe Ser Leu Asp Asp Lys Glu Gln Gln Lys Cys Ser Glu Thr Ile Glu
         35                  40                  45

Ala Leu Lys Gln Glu Ala Arg Gly Met Leu Met Ala Thr Thr Pro
     50                  55                  60

Leu Gln Gln Met Thr Leu Ile Asp Thr Leu Glu Arg Leu Gly Leu Ser
 65                  70                  75                  80

Phe His Phe Glu Thr Glu Ile Glu Tyr Lys Ile Glu Leu Ile Asn Ala
                 85                  90                  95

Ala Glu Asp Asp Ala Phe Asp Leu Phe Ala Thr Ala Leu Arg Phe Arg
            100                 105                 110

Leu Leu Arg Gln His Gln Arg His Val Ser Cys Asp Val Phe Asp Lys
        115                 120                 125

Phe Ile Asp Lys Asp Gly Lys Phe Glu Glu Ser Leu Ser Asn Asn Val
    130                 135                 140

Glu Gly Leu Leu Ser Leu Tyr Glu Ala Ala His Val Gly Phe Arg Glu
145                 150                 155                 160

Glu Arg Ile Leu Gln Glu Ala Val Asn Phe Thr Arg His His Leu Glu
                165                 170                 175

Gly Ala Glu Leu Asp Gln Ser Pro Leu Leu Ile Arg Lys Val Lys
            180                 185                 190

Arg Ala Leu Glu His Pro Leu His Arg Asp Phe Pro Ile Val Tyr Ala
        195                 200                 205

Arg Leu Phe Ile Ser Ile Tyr Glu Lys Asp Asp Ser Arg Asp Glu Leu
    210                 215                 220

Leu Leu Lys Leu Ser Lys Val Asn Phe Lys Phe Met Gln Asn Leu Tyr
225                 230                 235                 240

Lys Glu Asp Leu Ser Gln Leu Ser Arg Trp Trp Asn Thr Trp Asn Leu
                245                 250                 255

Lys Ser Lys Leu Pro Tyr Ala Arg Asp Arg Val Val Glu Ala Tyr Val
            260                 265                 270

Trp Gly Val Gly Tyr His Tyr Glu Pro Gln Tyr Ser Tyr Val Arg Met
        275                 280                 285

Gly Leu Ala Lys Gly Val Leu Ile Cys Gly Ile Met Asp Asp Thr Tyr
    290                 295                 300
```

```
Asp Asn Tyr Ala Thr Leu Asn Glu Ala Gln Leu Phe Thr Gln Val Leu
305                 310                 315                 320

Asp Lys Trp Asp Arg Asp Glu Ala Glu Arg Leu Pro Glu Tyr Met Lys
            325                 330                 335

Ile Val Tyr Arg Phe Ile Leu Ser Ile Tyr Glu Asn Tyr Asp Arg Asp
                340                 345                 350

Ala Ala Lys Leu Gly Lys Ser Phe Ala Ala Pro Tyr Phe Lys Glu Thr
            355                 360                 365

Val Lys Gln Leu Ala Arg Ala Phe Asn Glu Glu Gln Lys Trp Val Met
370                 375                 380

Glu Arg Gln Leu Pro Ser Phe Gln Asp Tyr Val Lys Asn Ser Glu Lys
385                 390                 395                 400

Thr Ser Cys Ile Tyr Thr Met Phe Ala Ser Ile Ile Pro Gly Leu Lys
                405                 410                 415

Ser Val Thr Gln Glu Thr Ile Asp Trp Ile Lys Ser Glu Pro Thr Leu
            420                 425                 430

Ala Thr Ser Thr Ala Met Ile Gly Arg Tyr Trp Asn Asp Thr Ser Ser
            435                 440                 445

Gln Leu Arg Glu Ser Lys Gly Gly Glu Met Leu Thr Ala Leu Asp Phe
            450                 455                 460

His Met Lys Glu Tyr Gly Leu Thr Lys Glu Glu Ala Ala Ser Lys Phe
465                 470                 475                 480

Glu Gly Leu Val Glu Glu Thr Trp Lys Asp Ile Asn Lys Glu Phe Ile
                485                 490                 495

Ala Thr Thr Asn Tyr Asn Val Gly Arg Glu Ile Ala Ile Thr Phe Leu
                500                 505                 510

Asn Tyr Ala Arg Ile Cys Glu Ala Ser Tyr Ser Lys Thr Asp Gly Asp
            515                 520                 525

Ala Tyr Ser Asp Pro Asn Val Ala Lys Ala Asn Val Val Ala Leu Phe
530                 535                 540

Val Asp Ala Ile Val Phe
545                 550

<210> SEQ ID NO 27
<211> LENGTH: 550
<212> TYPE: PRT
<213> ORGANISM: Artificial Sequence
<220> FEATURE:
<223> OTHER INFORMATION: Description of Artificial Sequence:
      E-beta-farnesene synthase protein variant
<220> FEATURE:
<221> NAME/KEY: VARIANT
<222> LOCATION: (1)..(550)
<223> OTHER INFORMATION: Computer-generated E-beta-farnesene synthase
      protein variant

<400> SEQUENCE: 27

Met Ala Thr Asn Gly Val Val Ile Ser Cys Leu Arg Glu Val Arg Pro
1               5                   10                  15

Pro Met Thr Lys His Ala Pro Ser Met Trp Thr Asp Thr Phe Ser Asn
                20                  25                  30

Phe Ser Leu Asp Asp Lys Glu Gln Gln Lys Cys Ser Glu Thr Ile Glu
            35                  40                  45

Ala Leu Lys Gln Glu Ala Arg Gly Met Leu Met Ala Ala Thr Ser Pro
        50                  55                  60

Leu Gln Gln Met Thr Leu Ile Asp Thr Leu Glu Arg Leu Gly Leu Ser
65                  70                  75                  80

Phe His Phe Glu Thr Glu Ile Glu Tyr Lys Ile Glu Leu Ile Asn Ala
```

-continued

```
                      85                  90                  95
Ala Glu Asp Asp Gly Phe Asp Leu Phe Ala Thr Ala Leu Arg Phe Arg
                100                 105                 110
Leu Leu Arg Gln His Gln Arg His Val Ser Cys Asp Val Phe Asp Lys
            115                 120                 125
Phe Ile Asp Lys Asp Gly Lys Phe Glu Glu Ser Leu Ser Asn Asn Val
        130                 135                 140
Glu Gly Leu Leu Ser Leu Tyr Glu Ala Ala His Val Gly Phe Arg Glu
145                 150                 155                 160
Glu Arg Ile Leu Gln Glu Ala Val Asn Phe Thr Arg His His Leu Glu
                165                 170                 175
Gly Ala Glu Leu Asp Gln Ser Pro Leu Leu Ile Arg Glu Lys Val Lys
            180                 185                 190
Arg Ala Leu Glu His Pro Leu His Arg Asp Phe Pro Ile Val Tyr Ala
        195                 200                 205
Arg Leu Phe Ile Ser Ile Tyr Glu Lys Asp Asp Ser Arg Asp Glu Leu
    210                 215                 220
Leu Leu Lys Leu Ser Lys Val Asn Phe Lys Phe Met Gln Asn Leu Tyr
225                 230                 235                 240
Lys Glu Glu Leu Ser Gln Leu Ser Arg Trp Trp Asn Thr Trp Asn Leu
                245                 250                 255
Lys Ser Lys Leu Pro Tyr Ala Arg Asp Arg Val Val Glu Ala Tyr Val
            260                 265                 270
Trp Gly Val Gly Tyr His Tyr Glu Pro Gln Tyr Ser Tyr Val Arg Met
        275                 280                 285
Gly Leu Ala Lys Gly Val Leu Ile Cys Gly Ile Met Asp Asp Thr Tyr
    290                 295                 300
Asp Asn Tyr Ala Thr Leu Asn Glu Ala Gln Leu Phe Thr Gln Val Leu
305                 310                 315                 320
Asp Lys Trp Asp Arg Asp Glu Ala Glu Arg Leu Pro Glu Tyr Met Lys
                325                 330                 335
Ile Val Tyr Arg Phe Ile Leu Ser Ile Tyr Glu Asn Tyr Glu Arg Asp
            340                 345                 350
Ala Ala Lys Leu Gly Lys Ser Phe Ala Ala Pro Tyr Phe Lys Glu Thr
        355                 360                 365
Val Lys Gln Leu Ala Arg Ala Phe Asn Asp Glu Gln Lys Trp Val Met
    370                 375                 380
Glu Arg Gln Leu Pro Ser Phe Gln Asp Tyr Val Lys Asn Ser Glu Lys
385                 390                 395                 400
Thr Ser Cys Ile Tyr Thr Met Phe Ala Ser Ile Ile Pro Gly Leu Lys
                405                 410                 415
Ser Val Thr Gln Glu Thr Ile Asp Trp Ile Lys Ser Glu Pro Thr Leu
            420                 425                 430
Ala Thr Ser Thr Ala Met Ile Gly Arg Tyr Trp Asn Asp Thr Ser Ser
        435                 440                 445
Gln Leu Arg Glu Ser Lys Gly Gly Glu Met Leu Thr Ala Leu Asp Phe
    450                 455                 460
His Met Lys Glu Tyr Gly Leu Thr Lys Glu Glu Ala Ala Ser Lys Phe
465                 470                 475                 480
Glu Gly Leu Val Glu Glu Thr Trp Lys Asp Ile Asn Lys Glu Phe Ile
                485                 490                 495
Ala Thr Thr Asn Tyr Asn Val Gly Arg Gly Ile Ala Ile Thr Phe Leu
            500                 505                 510
```

```
Asn Tyr Ala Arg Ile Cys Glu Ala Ser Tyr Ser Lys Thr Asp Gly Asp
            515                 520                 525

Ala Tyr Ser Asp Pro Asn Val Ala Lys Ala Asn Val Ala Leu Phe
530                 535                 540

Val Asp Ala Ile Val Phe
545                 550

<210> SEQ ID NO 28
<211> LENGTH: 550
<212> TYPE: PRT
<213> ORGANISM: Artificial Sequence
<220> FEATURE:
<223> OTHER INFORMATION: Description of Artificial Sequence:
      E-beta-farnesene synthase protein
<220> FEATURE:
<221> NAME/KEY: VARIANT
<222> LOCATION: (1)..(550)
<223> OTHER INFORMATION: Computer-generated E-beta-farnesene synthase
      protein variant

<400> SEQUENCE: 28

Met Ala Thr Asn Gly Val Val Ile Ser Cys Leu Arg Glu Val Arg Pro
 1               5                  10                  15

Pro Met Thr Lys His Ala Pro Ser Met Trp Thr Asp Thr Phe Ser Asn
            20                  25                  30

Phe Ser Leu Asp Asp Lys Glu Gln Lys Cys Ser Glu Thr Ile Glu
         35                  40                  45

Ala Leu Lys Gln Glu Ala Arg Gly Met Leu Met Ala Ala Thr Thr Pro
     50                  55                  60

Leu Gln Gln Met Thr Leu Ile Asp Thr Leu Glu Arg Leu Gly Leu Ser
 65                  70                  75                  80

Phe His Phe Glu Thr Glu Ile Glu Tyr Lys Ile Glu Leu Ile Asn Ala
                 85                  90                  95

Ala Glu Asp Asp Gly Phe Asp Leu Phe Ala Thr Ala Leu Arg Phe Arg
            100                 105                 110

Leu Leu Arg Gln His Gln Arg His Val Ser Cys Asp Val Phe Asp Lys
        115                 120                 125

Phe Ile Asp Lys Asp Gly Lys Phe Glu Glu Ser Leu Ser Asn Asn Val
130                 135                 140

Glu Gly Leu Leu Ser Leu Tyr Glu Ala Ala His Val Gly Phe Arg Glu
145                 150                 155                 160

Glu Arg Ile Leu Gln Glu Ala Val Asn Phe Thr Arg His His Leu Glu
                165                 170                 175

Gly Ala Glu Leu Asp Gln Ser Pro Leu Leu Ile Arg Glu Lys Val Lys
            180                 185                 190

Arg Ala Leu Glu His Pro Leu His Arg Asp Phe Pro Ile Val Tyr Ala
        195                 200                 205

Arg Leu Phe Ile Ser Ile Tyr Glu Lys Asp Asp Ser Arg Asp Glu Leu
    210                 215                 220

Leu Leu Lys Leu Ser Lys Val Asn Phe Lys Phe Met Gln Asn Leu Tyr
225                 230                 235                 240

Lys Glu Glu Leu Ser Gln Leu Ser Arg Trp Trp Asn Thr Trp Asn Leu
                245                 250                 255

Lys Ser Lys Leu Pro Tyr Ala Arg Asp Arg Val Val Glu Ala Tyr Val
            260                 265                 270

Trp Gly Val Gly Tyr His Tyr Glu Pro Gln Tyr Ser Tyr Val Arg Met
        275                 280                 285

Gly Leu Ala Lys Gly Val Leu Ile Cys Gly Ile Met Asp Asp Thr Tyr
```

-continued

```
            290                 295                 300
Asp Asn Tyr Ala Thr Leu Asn Glu Ala Gln Leu Phe Thr Gln Val Leu
305                 310                 315                 320

Asp Lys Trp Asp Arg Asp Glu Ala Glu Arg Leu Pro Glu Tyr Met Lys
                325                 330                 335

Ile Val Tyr Arg Phe Ile Leu Ser Ile Tyr Glu Asn Tyr Glu Arg Asp
                340                 345                 350

Ala Ala Lys Leu Gly Lys Ser Phe Ala Ala Pro Tyr Phe Lys Glu Thr
                355                 360                 365

Val Lys Gln Leu Ala Arg Ala Phe Asn Glu Glu Gln Lys Trp Val Met
    370                 375                 380

Glu Arg Gln Leu Pro Ser Phe Gln Asp Tyr Val Lys Asn Ser Glu Lys
385                 390                 395                 400

Thr Ser Cys Ile Tyr Thr Met Phe Ala Ser Ile Ile Pro Gly Leu Lys
                405                 410                 415

Ser Val Thr Gln Glu Thr Ile Asp Trp Ile Lys Ser Glu Pro Thr Leu
                420                 425                 430

Ala Thr Ser Thr Ala Met Ile Gly Arg Tyr Trp Asn Asp Thr Ser Ser
            435                 440                 445

Gln Leu Arg Glu Ser Lys Gly Gly Glu Met Leu Thr Ala Leu Asp Phe
        450                 455                 460

His Met Lys Glu Tyr Gly Leu Thr Lys Asp Glu Ala Ala Ser Lys Phe
465                 470                 475                 480

Glu Gly Leu Val Glu Glu Thr Trp Lys Asp Ile Asn Lys Glu Phe Ile
                485                 490                 495

Ala Thr Thr Asn Tyr Asn Val Gly Arg Glu Ile Ala Ile Thr Phe Leu
                500                 505                 510

Asn Tyr Ala Arg Ile Cys Glu Ala Ser Tyr Ser Lys Thr Asp Gly Asp
            515                 520                 525

Ala Tyr Ser Asp Pro Asn Val Ala Lys Ala Asn Ile Val Ala Leu Phe
        530                 535                 540

Val Asp Ala Ile Val Phe
545                 550
```